(12) United States Patent
Scheller et al.

(10) Patent No.: US 9,757,277 B2
(45) Date of Patent: *Sep. 12, 2017

(54) STEERABLE LASER PROBE

(71) Applicant: Katalyst Surgical, LLC, Chesterfield, MO (US)

(72) Inventors: Gregg D Scheller, Wildwood, MO (US); Matthew N Zeid, Ballwin, MO (US)

(73) Assignee: Katalyst Surgical, LLC, Chesterfield, MO (US)

( * ) Notice: Subject to any disclaimer, the term of this patent is extended or adjusted under 35 U.S.C. 154(b) by 389 days.

This patent is subject to a terminal disclaimer.

(21) Appl. No.: 14/461,483

(22) Filed: Aug. 18, 2014

(65) Prior Publication Data

US 2014/0358131 A1    Dec. 4, 2014

Related U.S. Application Data

(63) Continuation of application No. 13/586,811, filed on Aug. 15, 2012, now Pat. No. 8,840,605.

(51) Int. Cl.
*A61F 9/008*    (2006.01)
*A61B 18/22*    (2006.01)

(52) U.S. Cl.
CPC .......... *A61F 9/00821* (2013.01); *A61B 18/22* (2013.01); *A61B 2018/225* (2013.01);
(Continued)

(58) Field of Classification Search
CPC ... A61F 9/00821; A61B 18/22; A61B 18/225; A61B 18/2238; A61B 18/2288
See application file for complete search history.

(56) References Cited

U.S. PATENT DOCUMENTS 4,122,853 A * 10/1978 Smith ................. A61F 9/00821
604/37
5,190,050 A    3/1993 Nitzsche
(Continued)

FOREIGN PATENT DOCUMENTS

EP            0900547 B1    3/1999
WO    WO 2006/091597 A1    8/2006

OTHER PUBLICATIONS

H. Fischer, B. Vogel, W. Pfleging, H. Besser, Flexible distal tip made of nitinol (NiTi) for a steerable endoscopic camera system, Materials Science and Engineering A273-275 (1999) 780-783.

*Primary Examiner* — Nathan J Jenness
(74) *Attorney, Agent, or Firm* — Kevin P. Rollins

(57) ABSTRACT

A steerable laser probe may include a handle having a handle proximal end and a handle distal end, an actuation structure of the handle, a housing sleeve, a shape memory sleeve at least partially disposed within the housing sleeve, and an optic fiber disposed within the shape memory sleeve and within an inner bore of the handle. A compression of the actuation structure may be configured to gradually curve the optic fiber. A compression of the actuation structure may be configured to gradually straighten the optic fiber. A decompression of the actuation structure may be configured to gradually curve the optic fiber. A decompression of the actuation structure may be configured to gradually straighten the optic fiber.

17 Claims, 41 Drawing Sheets

(52) U.S. Cl.
CPC .......... *A61B 2018/2238* (2013.01); *A61B 2018/2288* (2013.01); *A61F 2009/00863* (2013.01)

(56) References Cited

U.S. PATENT DOCUMENTS

| | | | |
|---|---|---|---|
| 5,355,871 A | 10/1994 | Hurley et al. | |
| 5,381,782 A | 1/1995 | DeLaRama et al. | |
| 5,439,000 A | 8/1995 | Gunderson et al. | |
| 5,454,794 A | 10/1995 | Narciso et al. | |
| 5,520,222 A | 5/1996 | Chikama | |
| 6,123,699 A | 9/2000 | Webster, Jr. | |
| 6,126,654 A | 10/2000 | Giba et al. | |
| 6,198,974 B1 | 3/2001 | Webster, Jr. | |
| 6,488,695 B1 | 12/2002 | Hickingbotham | |
| 6,505,530 B2 | 1/2003 | Adler et al. | |
| 6,530,913 B1 | 3/2003 | Giba et al. | |
| 6,551,302 B1 | 4/2003 | Rosinko et al. | |
| 6,572,608 B1 | 6/2003 | Lee et al. | |
| 6,620,153 B2 | 9/2003 | Mueller et al. | |
| 6,730,076 B2 | 5/2004 | Hickingbotham | |
| 6,863,668 B2 | 3/2005 | Gillespie et al. | |
| 6,984,230 B2 | 1/2006 | Scheller et al. | |
| 7,004,957 B1 | 2/2006 | Dampney et al. | |
| 7,303,533 B2 | 12/2007 | Johansen et al. | |
| 7,402,158 B2 | 7/2008 | Scheller et al. | |
| 7,632,242 B2 | 12/2009 | Griffin et al. | |
| 7,766,904 B2 | 8/2010 | Mc Gowan, Sr. et al. | |
| 8,038,692 B2 | 10/2011 | Valencia et al. | |
| 8,075,553 B2 | 12/2011 | Scheller et al. | |
| 8,197,468 B2 | 6/2012 | Scheller et al. | |
| 2003/0171762 A1 | 9/2003 | Forchette et al. | |
| 2004/0181138 A1 | 9/2004 | Hindricks et al. | |
| 2005/0054900 A1 | 3/2005 | Mawn et al. | |
| 2005/0157985 A1 | 7/2005 | McGowan, Sr. et al. | |
| 2005/0272975 A1 | 12/2005 | McWeeney et al. | |
| 2006/0004348 A1* | 1/2006 | Scheller | A61B 18/22 606/4 |
| 2006/0293270 A1* | 12/2006 | Adamis | C12N 15/115 514/44 R |
| 2007/0185514 A1 | 8/2007 | Kirchhevel | |
| 2009/0018393 A1 | 1/2009 | Dick et al. | |
| 2009/0187170 A1 | 7/2009 | Auld et al. | |
| 2009/0312750 A1 | 12/2009 | Spaide | |
| 2010/0004642 A1 | 1/2010 | Lumpkin | |
| 2010/0268234 A1 | 10/2010 | Aho et al. | |
| 2011/0028947 A1 | 2/2011 | Scheller et al. | |
| 2012/0116361 A1 | 5/2012 | Hanlon et al. | |
| 2013/0035551 A1 | 2/2013 | Yu et al. | |
| 2013/0060240 A1 | 3/2013 | Scheller et al. | |
| 2013/0071507 A1 | 3/2013 | Scheller et al. | |
| 2013/0096541 A1 | 4/2013 | Scheller et al. | |
| 2013/0116671 A1 | 5/2013 | Scheller et al. | |
| 2013/0144278 A1* | 6/2013 | Papac | A61F 9/00821 606/4 |
| 2013/0150838 A1 | 6/2013 | Scheller et al. | |
| 2013/0165910 A1 | 6/2013 | Scheller et al. | |

* cited by examiner

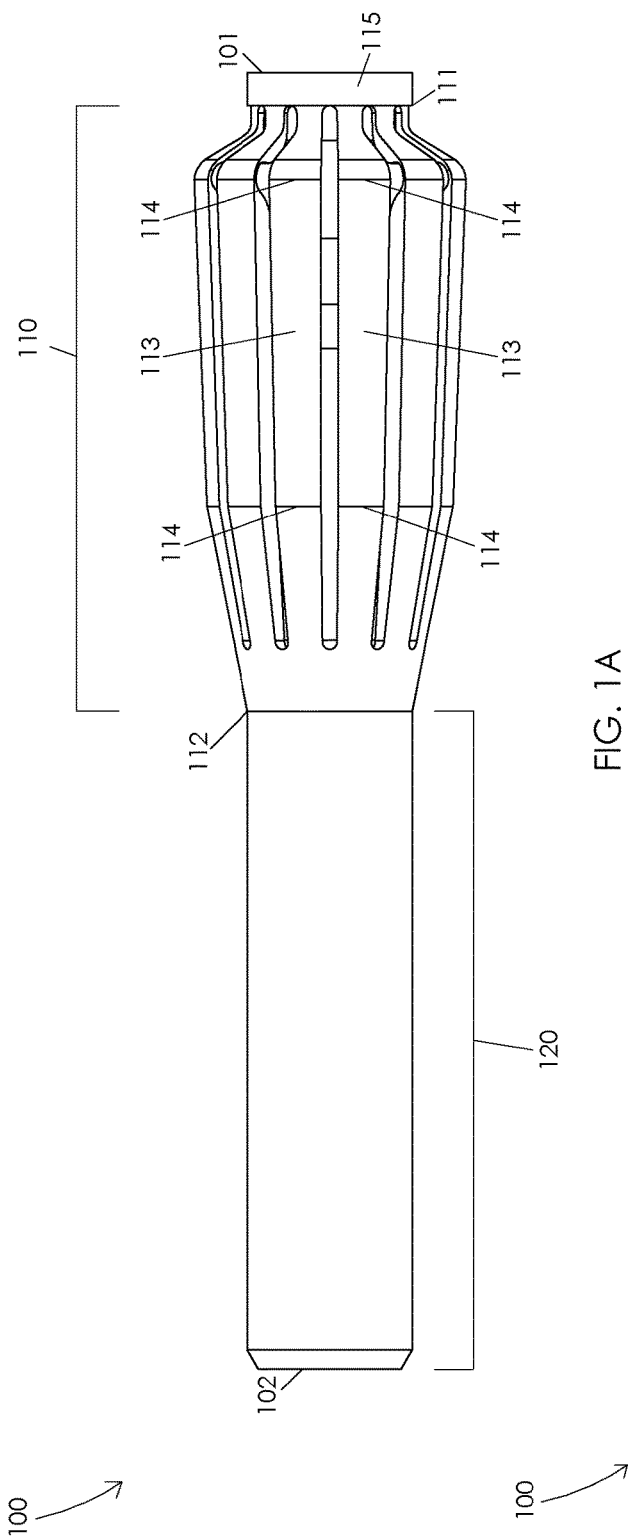
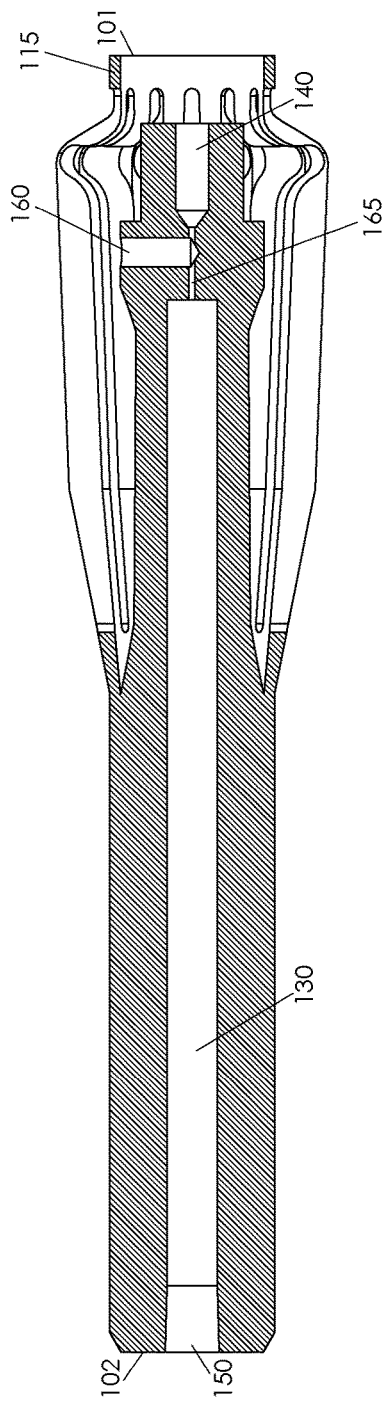
FIG. 1A
FIG. 1B

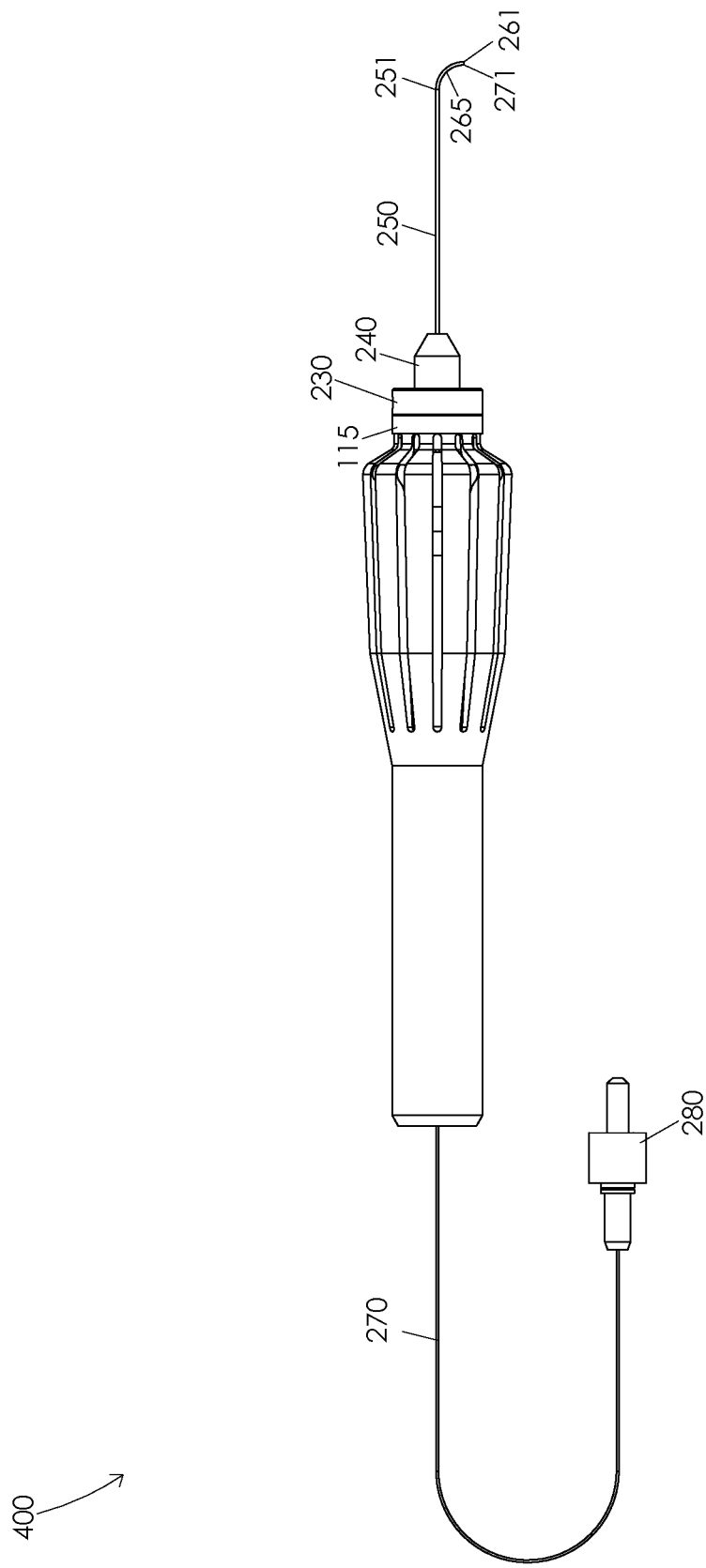

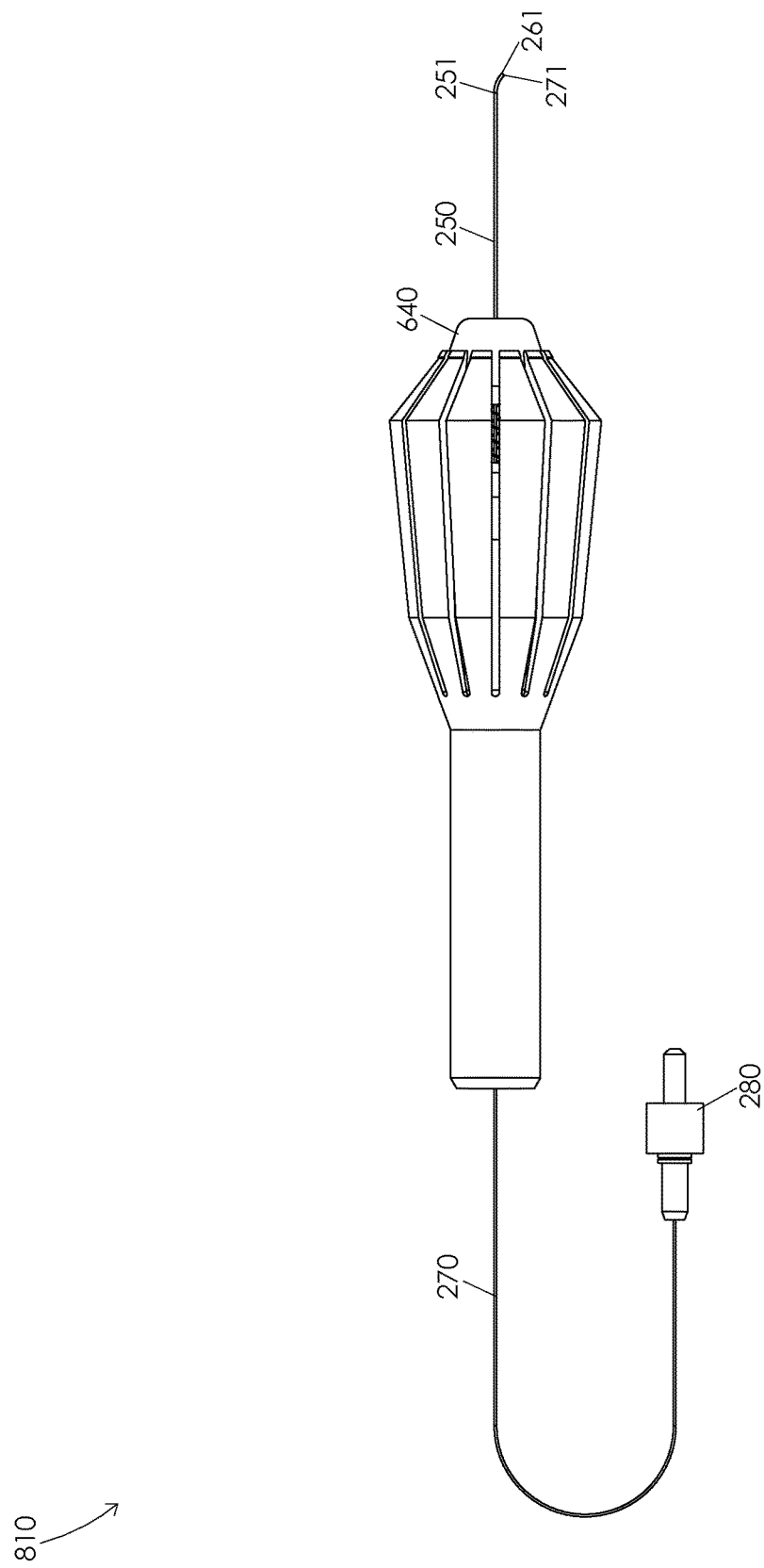

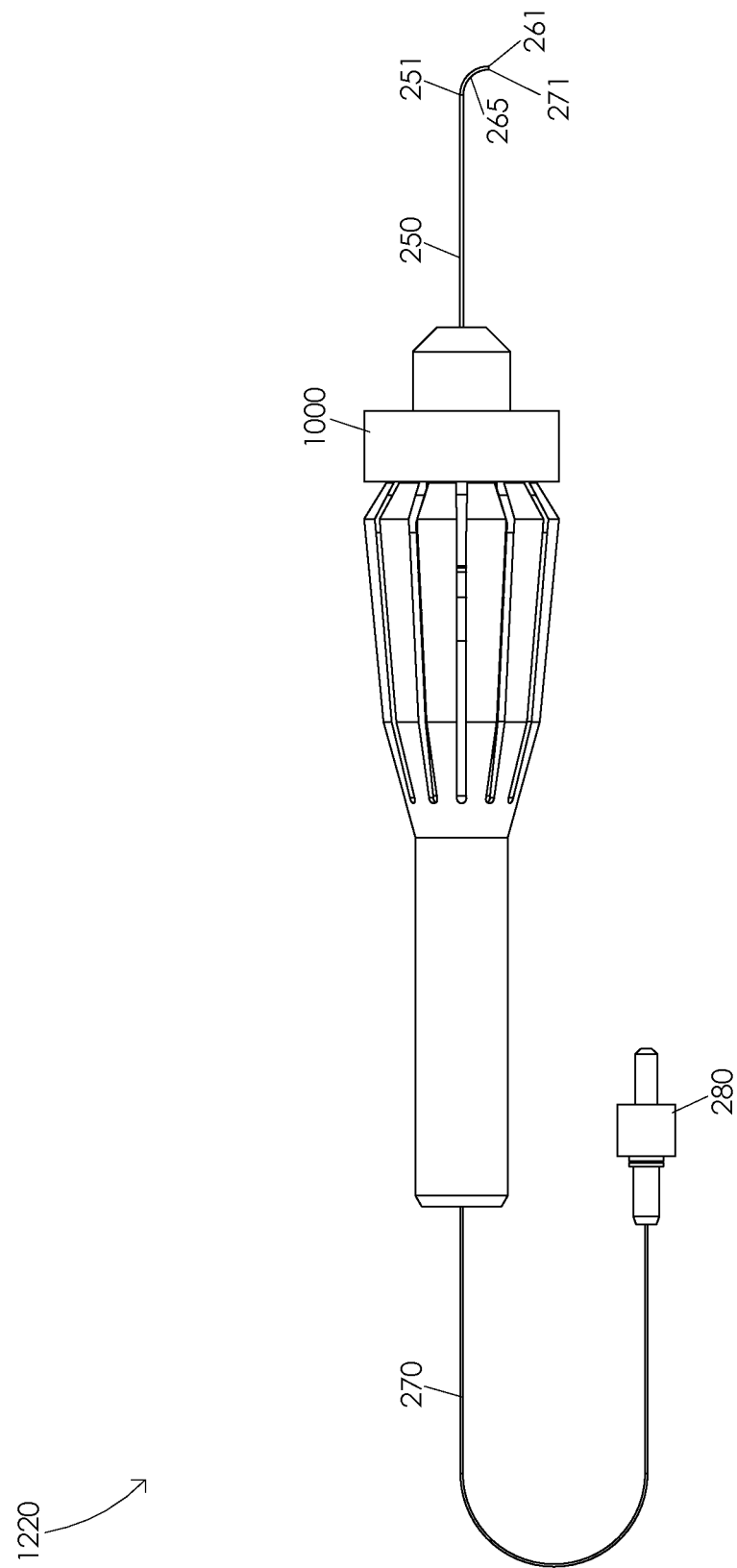

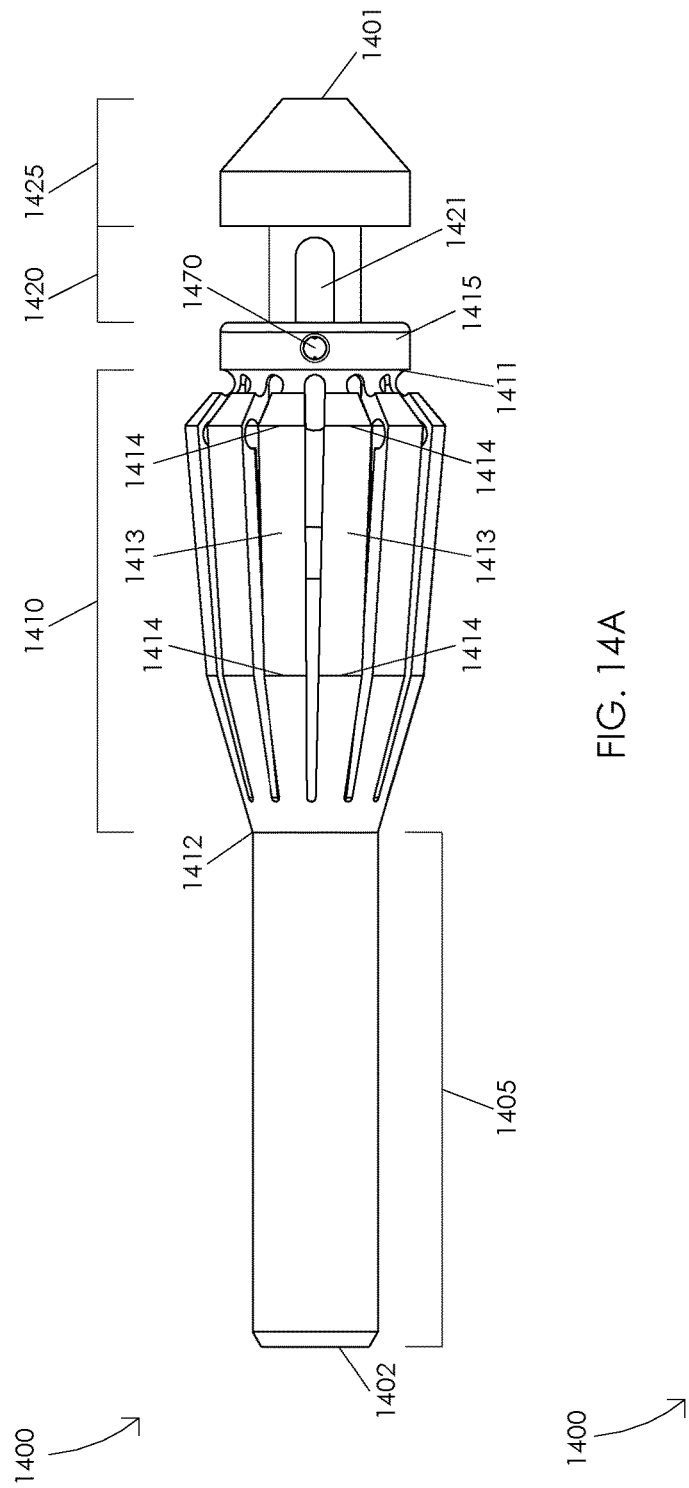
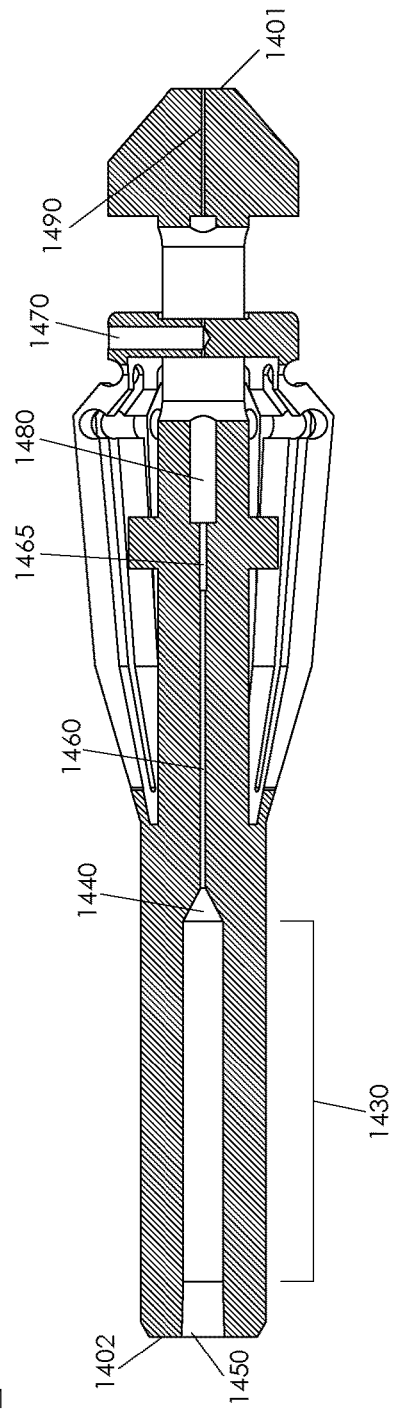
FIG. 14A
FIG. 14B

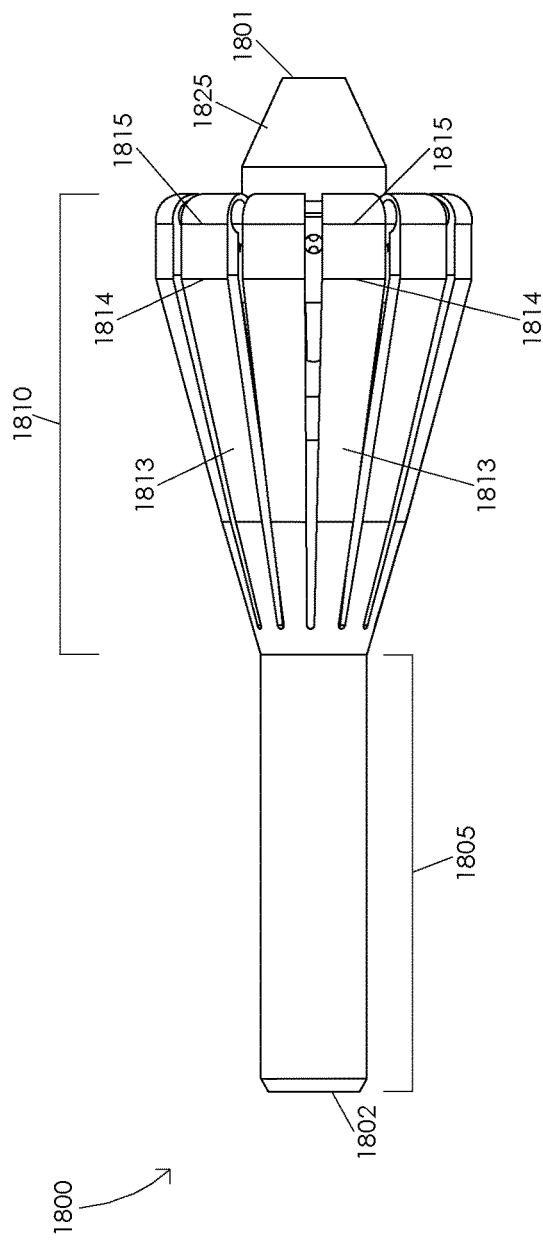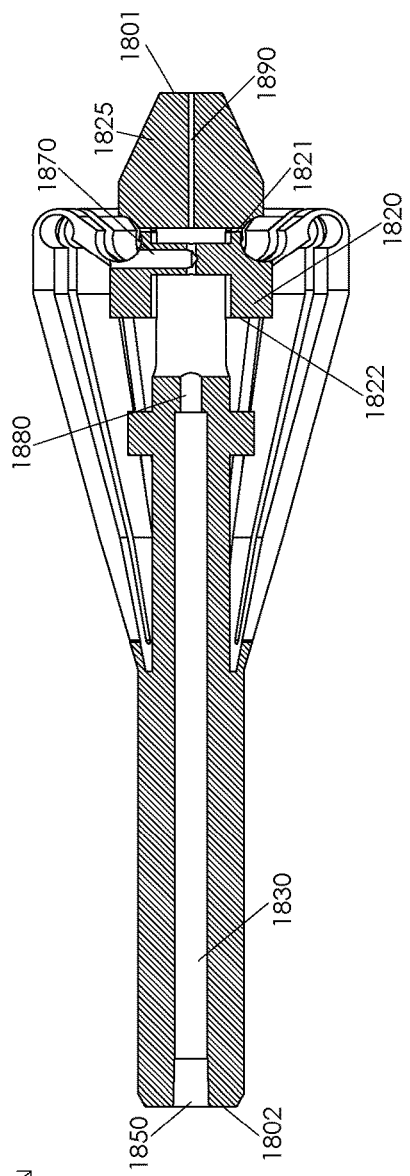
FIG. 18A
FIG. 18B

STEERABLE LASER PROBE

CROSS-REFERENCE TO RELATED APPLICATIONS

This application is a continuation of prior application Ser. No. 13/586,811, filed Aug. 15, 2012.

FIELD OF THE INVENTION

The present disclosure relates to a surgical instrument, and, more particularly, to a steerable laser probe.

BACKGROUND OF THE INVENTION

A wide variety of ophthalmic procedures require a laser energy source. For example, ophthalmic surgeons may use laser photocoagulation to treat proliferative retinopathy. Proliferative retinopathy is a condition characterized by the development of abnormal blood vessels in the retina that grow into the vitreous humor. Ophthalmic surgeons may treat this condition by energizing a laser to cauterize portions of the retina to prevent the abnormal blood vessels from growing and hemorrhaging.

In order to increase the chances of a successful laser photocoagulation procedure, it is important that a surgeon is able aim the laser at a plurality of targets within the eye, e.g., by guiding or moving the laser from a first target to a second target within the eye. It is also important that the surgeon is able to easily control a movement of the laser. For example, the surgeon must be able to easily direct a laser beam by steering the beam to a first position aimed at a first target, guide the laser beam from the first position to a second position aimed at a second target, and hold the laser beam in the second position. Accordingly, there is a need for a surgical laser probe that can be easily guided to a plurality of targets within the eye.

BRIEF SUMMARY OF THE INVENTION

The present disclosure provides a steerable laser probe. In one or more embodiments, a steerable laser probe may comprise a handle having a handle proximal end and a handle distal end, an actuation structure of the handle, a housing sleeve, a shape memory sleeve at least partially disposed within the housing sleeve, and an optic fiber disposed within the shape memory sleeve and within an inner bore of the handle. Illustratively, a compression of the actuation structure may be configured to gradually curve the optic fiber. In one or more embodiments, a compression of the actuation structure may be configured to gradually straighten the optic fiber. Illustratively, a decompression of the actuation structure may be configured to gradually curve the optic fiber. In one or more embodiments, a decompression of the actuation structure may be configured to gradually straighten the optic fiber.

BRIEF DESCRIPTION OF THE DRAWINGS

The above and further advantages of the present invention may be better understood by referring to the following description in conjunction with the accompanying drawings in which like reference numerals indicate identical or functionally similar elements:

FIGS. 1A and 1B are schematic diagrams illustrating a handle;

FIGS. 4A, 4B, and 4C illustrate a gradual straightening of an optic fiber;

FIGS. 8A, 8B, and 8C illustrate a gradual straightening of an optic fiber;

FIGS. 12A, 12B, and 12C illustrate a gradual curving of an optic fiber;

FIGS. 14A and 14B are schematic diagrams illustrating a handle;

FIGS. 18A and 18B are schematic diagrams illustrating a handle;

DETAILED DESCRIPTION OF AN ILLUSTRATIVE EMBODIMENT

Figure 2:
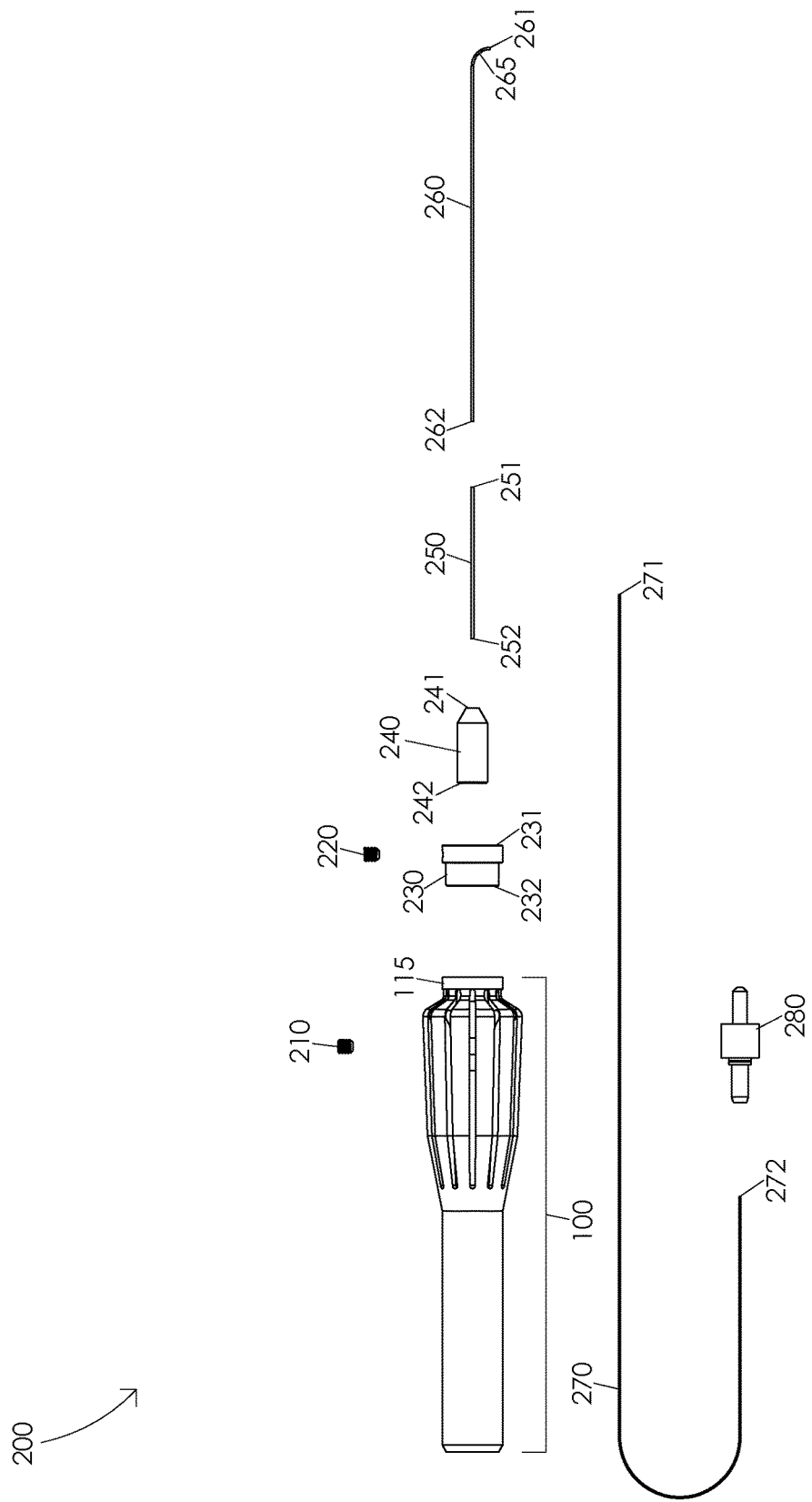
FIG. 2 illustrates an exploded view of a steerable laser probe assembly.

FIGS. 1A and 1B are schematic diagrams illustrating a handle 100. FIG. 1A illustrates a top view of handle 100. In one or more embodiments, handle 100 may comprise a handle distal end 101, a handle proximal end 102, an actuation structure 110, and a handle base 120. Illustratively, actuation structure 110 comprises an actuation structure distal end 111 and an actuation structure proximal end 112. In one or more embodiments, actuation structure 110 may comprise a plurality of actuation arms 113. Illustratively, each actuation arm 113 may comprise at least one extension mechanism 114. In one or more embodiments, actuation structure 110 may comprise a shape memory material configured to project actuation structure distal end 111 a first distance from actuation structure proximal end 112 when actuation structure 110 is fully decompressed. Actuation structure 110 may comprise a shape memory material configured to project actuation structure distal end 111 a second distance from actuation structure proximal end 112 when actuation structure 110 is fully compressed. Illustratively, the second distance may be greater than the first distance. Actuation structure 110 may be manufactured from any suitable material, e.g., polymers, metals, metal alloys, etc., or from any combination of suitable materials.

Illustratively, actuation structure 110 may be compressed by an application of a compressive force to actuation structure 110. In one or more embodiments, actuation structure 110 may be compressed by an application of one or more compressive forces located at one or more locations around an outer perimeter of actuation structure 110. Illustratively, the one or more locations may comprise any of a plurality of locations around the outer perimeter of actuation structure 110. For example, a surgeon may compress actuation structure 110 by squeezing actuation structure 110. Illustratively, the surgeon may compress actuation structure 110 by squeezing actuation structure 110 at any particular location of a plurality of locations around an outer perimeter of actuation structure 110. For example, a surgeon may rotate handle 100 and compress actuation structure 110 from any rotational position of a plurality of rotational positions of handle 100.

In one or more embodiments, actuation structure 110 may be compressed by an application of a compressive force to any one or more of the plurality of actuation arms 113. Illustratively, each actuation arm 113 may be configured to actuate independently. In one or more embodiments, each actuation arm 113 may be connected to one or more of the plurality of actuation arms 113 wherein an actuation of a particular actuation arm 113 may be configured to actuate every actuation arm 113 of the plurality of actuation arms 113. In one or more embodiments, a compression of actuation structure 110, e.g., due to an application of a compressive force to a particular actuation arm 113, may be configured to actuate the particular actuation arm 113. Illustratively, an actuation of the particular actuation arm 113 may be configured to actuate every actuation arm 113 of the plurality of actuation arms 113. In one or more embodiments, an application of a compressive force to a particular actuation arm 113 may be configured to extend at least one extension mechanism 114 of the particular actuation arm 113. Illustratively, a particular actuation arm 113 may extend a first length from handle base 120. An extension of an extension mechanism 114 of the particular actuation arm 113, e.g., due to an application of a compressive force to the particular actuation arm 113, may be configured to extend the particular actuation arm a second length from handle base 120. Illustratively, the second length from handle base 120 may be greater than the first length from handle base 120.

FIG. 1B illustrates a cross-sectional view of handle 100. In one or more embodiments, handle 100 may comprise an inner bore 130, a distal bore 140, an inner bore proximal taper 150, a fixation mechanism chamber 160, and a shape memory sleeve guide 165. Illustratively, handle 100 may comprise a fixation lip 115 connected to actuation structure distal end 111. Handle 100 may be manufactured from any suitable material, e.g., polymers, metals, metal alloys, etc., or from any combination of suitable materials.

FIG. 2 illustrates an exploded view of a steerable laser probe assembly 200. In one or more embodiments, steerable laser probe assembly 200 may comprise a handle 100, a proximal fixation mechanism 210, a distal fixation mechanism 220, an outer nosecone 230 having an outer nosecone distal end 231 and an outer nosecone proximal end 232, an inner nosecone 240 having an inner nosecone distal end 241 and an inner nosecone proximal end 242, a housing sleeve 250 having a housing sleeve distal end 251 and a housing sleeve proximal end 252, a shape memory sleeve 260 having a shape memory sleeve distal end 261 and a shape memory sleeve proximal end 262, an optic fiber 270 having an optic fiber distal end 271 and an optic fiber proximal end 272, and a light source interface 280. Illustratively, light source interface 280 may be configured to interface with optic fiber proximal end 272. In one or more embodiments, light source interface 280 may comprise a standard light source connector, e.g., an SMA connector.

Illustratively, outer nosecone proximal end 232 may be fixed actuation structure 110, e.g., outer nosecone 230 may be fixed to fixation lip 115. In one or more embodiments, housing tube proximal end 252 may be fixed to inner nosecone distal end 241. Illustratively, distal fixation mechanism 220 may be configured to attach outer nosecone 230 and inner nosecone 240, e.g., outer nosecone distal end 231 may be fixed to inner nosecone proximal end 242. For example, distal fixation mechanism 220 may comprise a set screw configured to firmly attach outer nosecone 230 to inner nosecone 240. In one or more embodiments, distal fixation mechanism 220 may comprise an adhesive material configured to attach outer nosecone 230 to inner nosecone 240, or distal fixation mechanism 220 may comprise one or more magnets configured to attach outer nosecone 230 to inner nosecone.

Illustratively, optic fiber 270 may be disposed within shape memory sleeve 260, e.g., optic fiber distal end 271 may be adjacent to shape memory sleeve distal end 261. Optic fiber 270 may be fixed in a position within shape memory sleeve 260, e.g., with a biocompatible adhesive or any suitable fixation means. In one or more embodiments, shape memory sleeve 260 may comprise a pre-bent angle 265 configured to curve optic fiber 270 towards pre-bent angle 265. Illustratively, shape memory sleeve 260 may comprise a shape memory material, e.g., Nitinol, configured to curve optic fiber 270 towards one or more surgical targets within an eye. Shape memory sleeve 260 may be manufactured from any suitable material, e.g., polymers, metals, metal alloys, etc., or from any combination of suitable materials.

Illustratively, optic fiber 270 and shape memory sleeve 260 may be disposed within inner bore 130, shape memory sleeve guide 165, fixation mechanism chamber 160, distal bore 140, outer nosecone 230, inner nosecone 240, and housing sleeve 250. In one or more embodiments, optic fiber 270 and shape memory sleeve 260 may be fixed in a position relative to handle 100, e.g., by proximal fixation mechanism 210, wherein a compression of actuation structure 110 may actuate housing sleeve 250 relative to optic fiber 270 and shape memory sleeve 260. Illustratively, proximal fixation mechanism 210 may be configured to fix optic fiber 270 and shape memory sleeve 260, e.g., at fixation mechanism chamber 160, in a position relative to handle 100, e.g., such that when actuation structure 110 is fully decompressed, optic fiber distal end 271 extends from housing sleeve distal end 251 and shape memory sleeve 260 curves optic fiber 270 at pre-bent angle 265. In one or more embodiments, proximal fixation mechanism 210 may be configured to fix optic fiber 270 and shape memory sleeve 260, e.g., at fixation mechanism chamber 160, in a position relative to handle 100, e.g., such that when actuation structure 110 is fully compressed, optic fiber distal end 271 is contained within housing sleeve 250, e.g., optic fiber distal end 271 does not extend from housing sleeve distal end 251, and shape memory sleeve 260 and optic fiber 270 are temporarily straightened by housing sleeve 250.

Figure 3A:
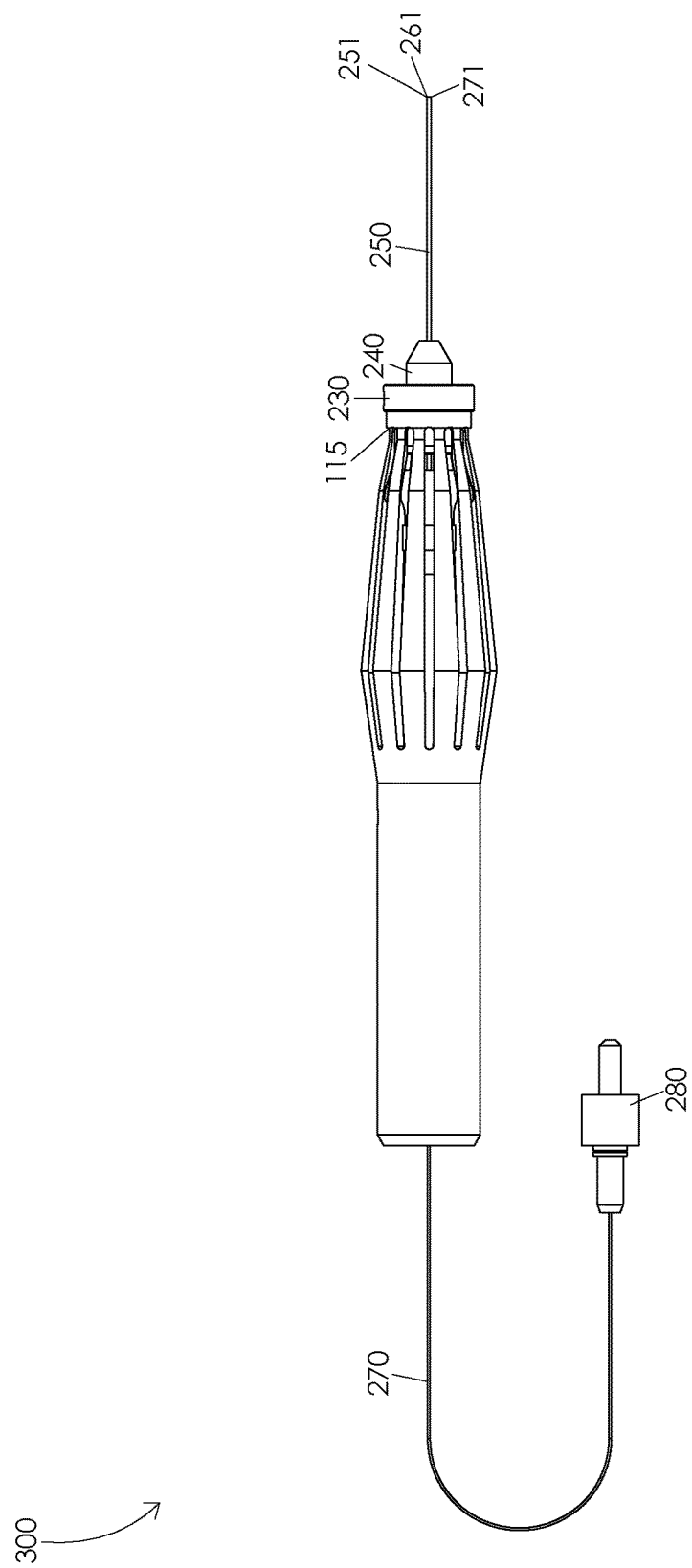
FIGS. 3A, 3B, and 3C illustrate a gradual curving of an optic fiber.
Figure 3B:
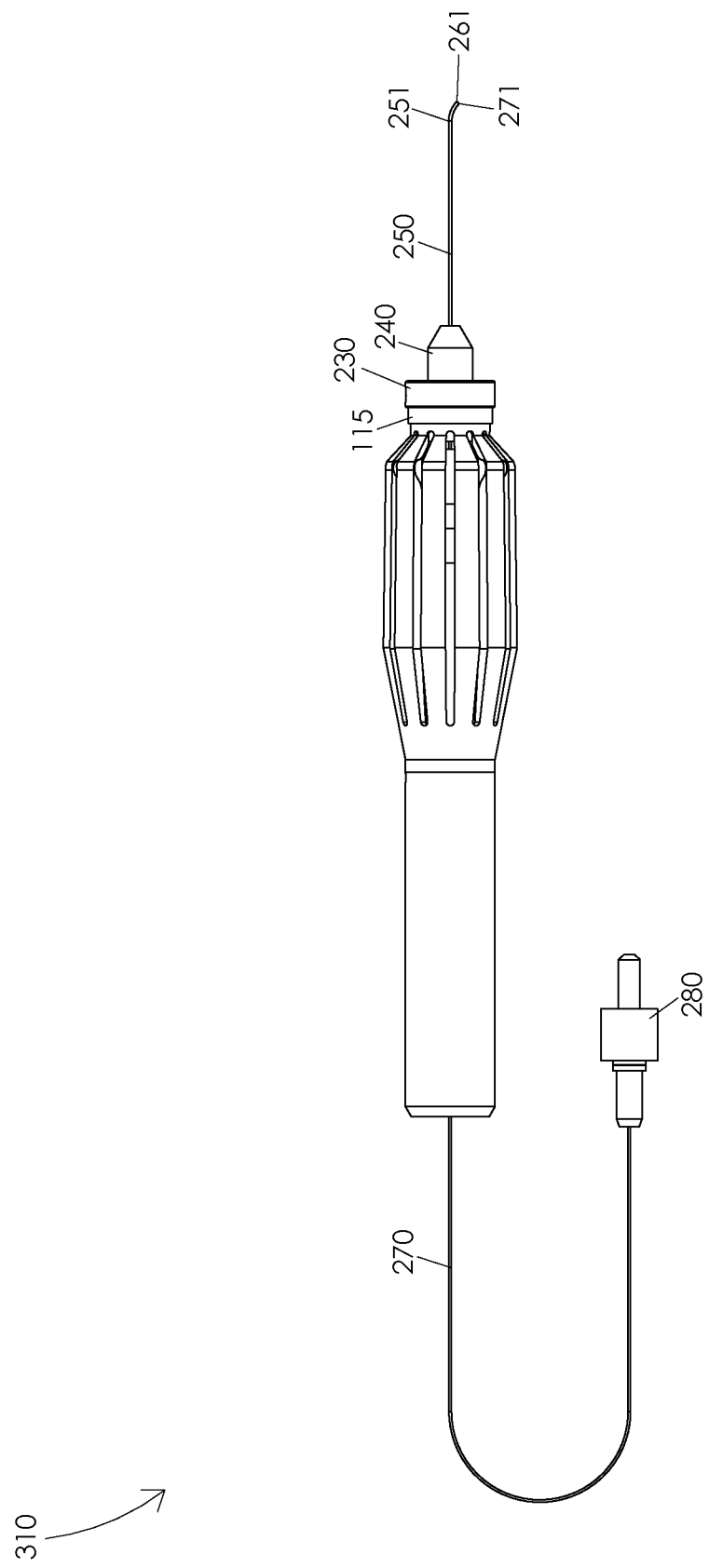
Figure 3C:
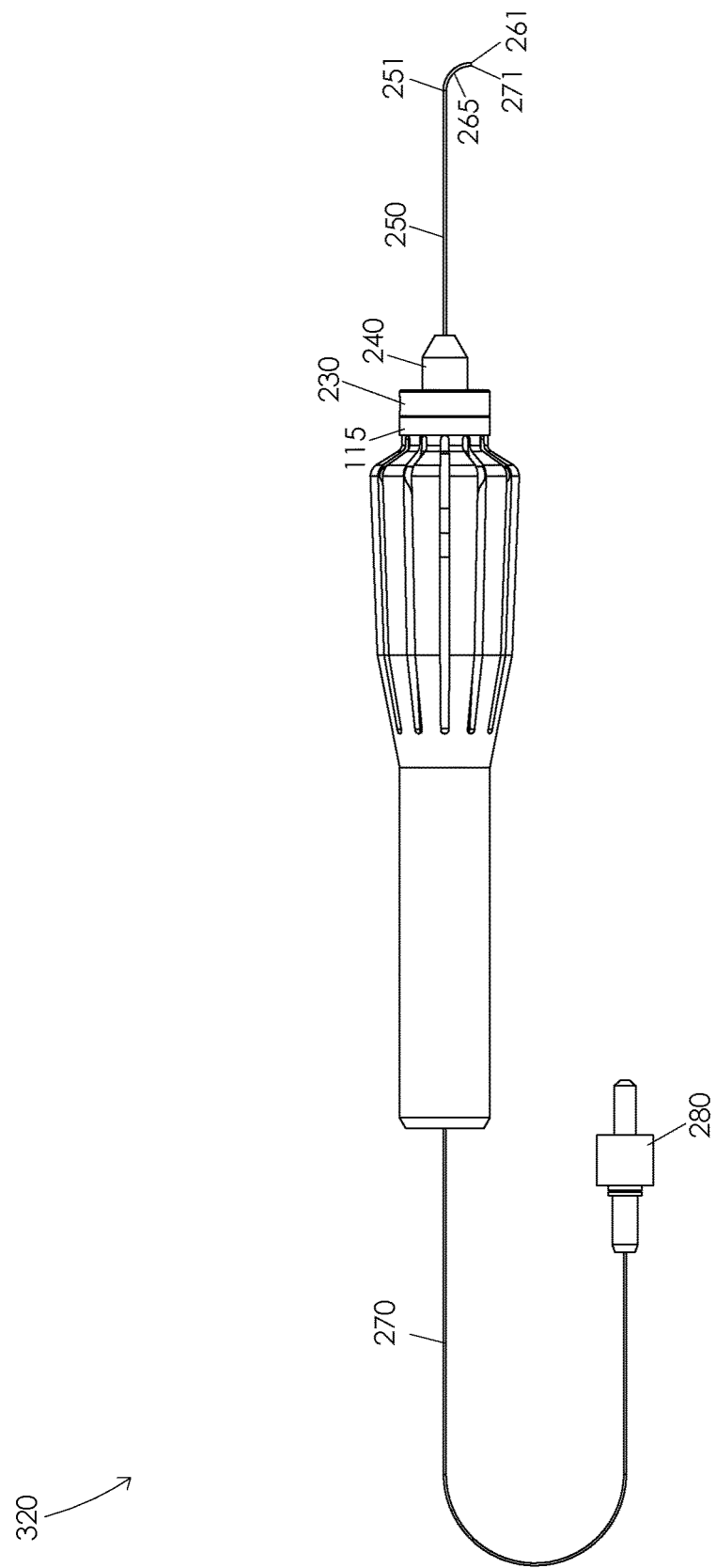

FIGS. 3A, 3B, and 3C illustrate a gradual curving of an optic fiber 270. FIG. 3A illustrates a straightened optic fiber 300. Illustratively, straightened optic fiber 300 may be fully contained within housing sleeve 250. In one or more embodiments, optic fiber 270 and shape memory sleeve 260 may be fully contained within housing sleeve 250, e.g., when actuation structure 110 is fully compressed. Illustratively, when optic fiber 270 and shape memory sleeve 260 are fully contained within housing sleeve 250, pre-bent angle 265 of shape memory sleeve 260 may be straightened by housing sleeve 250. For example, an angle between housing sleeve 250 and a line tangent to optic fiber distal end 271 may be 180 degrees, e.g., when housing sleeve 250 contains a straightened optic fiber 300.

FIG. 3B illustrates a partially curved optic fiber 310. In one or more embodiments, a decompression of actuation structure 110 may be configured to gradually retract housing sleeve 250 to expose optic fiber 270 and shape memory sleeve 260. Illustratively, as optic fiber 270 and shape memory sleeve 260 are gradually exposed by a retraction of housing sleeve 250, shape memory sleeve 260 may cause optic fiber 270 to curve towards pre-bent angle 265. In one or more embodiments, a decompression of actuation structure 110 may cause a straightened optic fiber 300 to gradually curve to a partially curved optic fiber 310. Illustratively, a decompression of actuation structure 110 may gradually expose optic fiber 270 and shape memory sleeve 260 causing optic fiber 270 to gradually curve towards pre-bent angle 265. For example, as an exposed length of optic fiber 270 and shape memory sleeve 260 is increased, e.g., by a retraction of housing sleeve 250, an angle between housing sleeve 250 and a line tangent to optic fiber distal end 271 may be decreased. Illustratively, optic fiber 270 and shape memory sleeve 260 may be exposed from housing sleeve distal end 251 at a first length with a first angle between housing sleeve 250 and a line tangent to optic fiber distal end 271. A retraction of housing sleeve 250, e.g., due to a decompression of actuation structure 110, may expose optic fiber 270 and shape memory sleeve 260 from housing sleeve distal end 251 at a second length with a second angle between housing sleeve 250 and a line tangent to optic fiber distal end 271. Illustratively, the second length may be greater than the first length and the second angle may be less than the first angle.

FIG. 3C illustrates a fully curved optic fiber 320. Illustratively, when housing sleeve 250 is fully retracted, e.g., by a full decompression of actuation structure 110, housing sleeve 250 may expose a fully curved optic fiber 320. In one or more embodiments, a decompression of actuation structure 110 may cause a partially curved optic fiber 310 to gradually curve to a fully curved optic fiber 320. Illustratively, when housing sleeve 250 is retracted to expose a partially curved optic fiber 310, optic fiber 270 and shape memory sleeve 260 may be exposed from housing sleeve distal end 251 at a partially extended length with a partially extended angle between housing sleeve 250 and a line tangent to optic fiber distal end 271. A retraction of housing sleeve 250, e.g., due to a full decompression of actuation structure 110, may expose optic fiber 270 and shape memory sleeve 260 from housing sleeve distal end 251 at fully extended length with a fully extended angle between housing sleeve 250 and a line tangent to optic fiber distal end 271, e.g., when housing sleeve 250 is retracted to expose a fully curved optic fiber 320. Illustratively, the fully extended length may be greater than the partially extended length and the fully extended angle may be less than the partially extended angle.

In one or more embodiments, one or more properties of a steerable laser probe may be adjusted to attain one or more desired steerable laser probe features. For example, a length that housing sleeve 250 extends from inner nosecone distal end 241 may be adjusted to vary an amount of decompression of actuation structure 110 configured to expose a particular length of optic fiber 270 and shape memory sleeve 260 from housing sleeve distal end 251. Illustratively, a position of fixation mechanism chamber 160 and proximal fixation mechanism 210 or a length of optic fiber 270 and shape memory sleeve 260 extending distally from a position of proximal fixation mechanism 210 may be adjusted to vary an amount of decompression of actuation structure 110 configured to expose a particular length of optic fiber 270 and shape memory sleeve 260 from housing sleeve distal end 251. For example, a distance that inner nosecone 240 extends from outer nosecone distal end 231 may be adjusted to vary an amount of decompression of actuation structure 110 configured to expose a particular length of optic fiber 270 and shape memory sleeve 260 from housing sleeve distal end 251. In one or more embodiments, a geometry of actuation structure 110 may be adjusted to vary an amount of decompression of actuation structure 110 configured to expose a particular length of optic fiber 270 and shape memory sleeve 260 from housing sleeve distal end 251. Illustratively, a magnitude of pre-bent angle 265 may be adjusted to vary a magnitude of an angle between housing sleeve 250 and a line tangent to optic fiber distal end 271 when a particular length of optic fiber 270 and shape memory sleeve 260 is exposed from housing sleeve distal end 251.

Figure 4B:
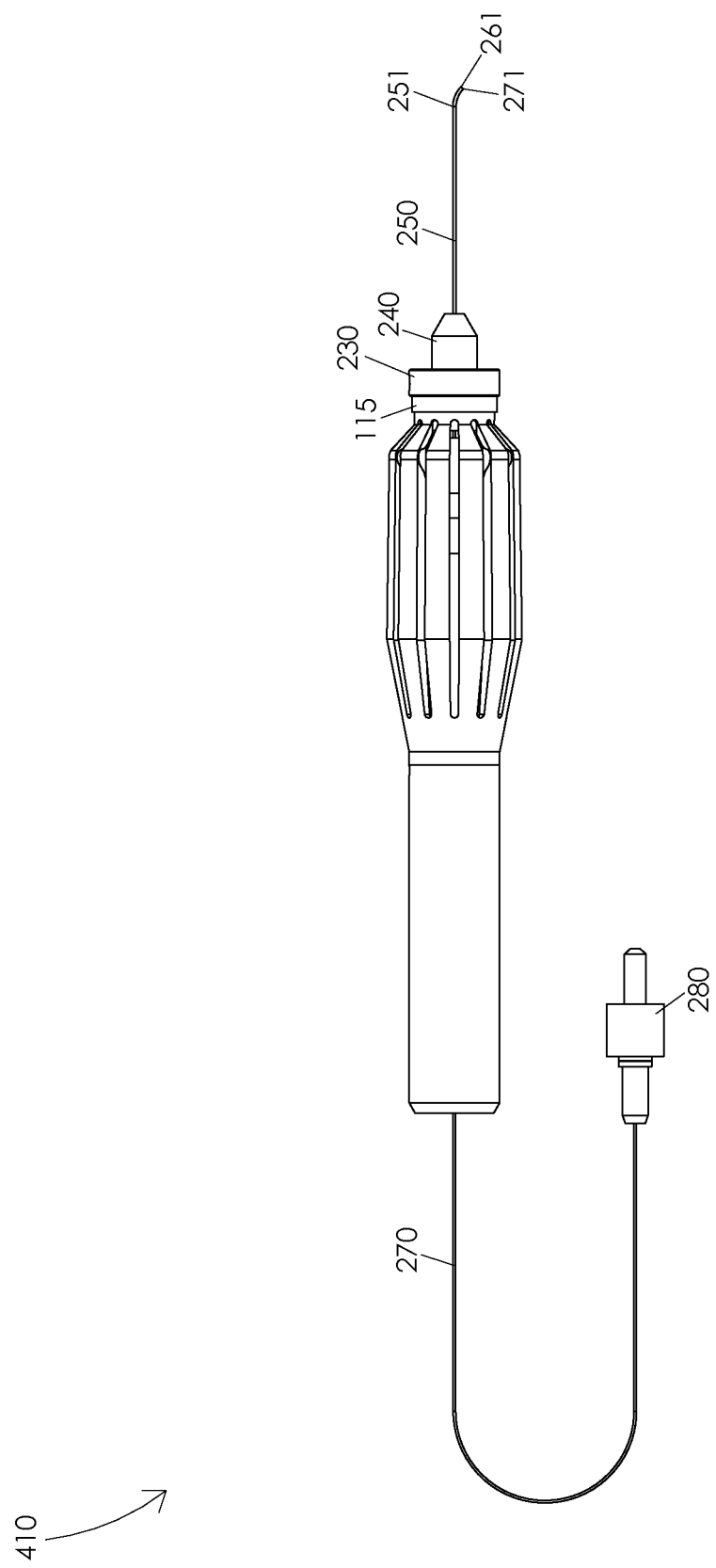
Figure 4C:
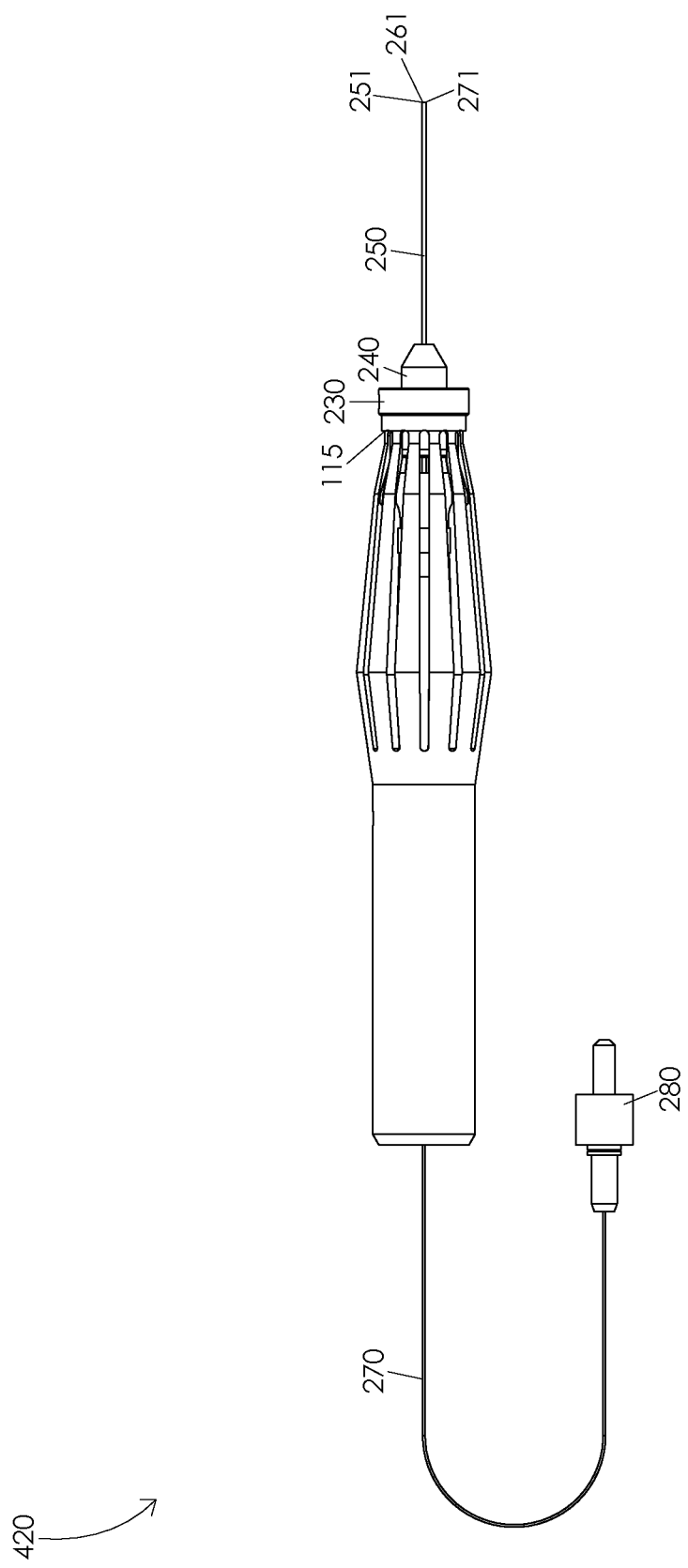

FIGS. 4A, 4B, and 4C illustrate a gradual straightening of an optic fiber 270. FIG. 4A illustrates a refracted housing sleeve 400. Illustratively, a refracted housing sleeve 400 may expose at least a portion of optic fiber 270 and shape memory sleeve 260 from housing sleeve distal end 251. In one or more embodiments, a full decompression of actuation structure 110 may be configured to cause housing sleeve 250 to be retracted relative to optic fiber 270 and shape memory sleeve 260 such that a fully curved optic fiber 320 is exposed from housing sleeve distal end 251. Illustratively, housing sleeve 250 may comprise a refracted housing sleeve 400, e.g., due to a full decompression of actuation structure 110.

FIG. 4B illustrates a partially extended housing sleeve 410. Illustratively, a partially extended housing sleeve 410 may hold a portion of pre-bent angle 265 in a straightened position within housing sleeve 250. In one or more embodiments, a compression of actuation structure 110 may extend housing sleeve 250 over optic fiber 270 and shape memory sleeve 260 causing shape memory sleeve 260 to gradually straighten optic fiber 270 from a fully curved optic fiber 320 to a partially curved optic fiber 310.

FIG. 4C illustrates a fully extended housing sleeve 420. Illustratively, a fully extended housing sleeve 420 may hold pre-bent angle 265 in a straightened position within housing sleeve 250. In one or more embodiments, a full compression of actuation structure 110 may extend housing sleeve 250 over optic fiber 270 and shape memory sleeve 260 causing shape memory sleeve 260 to gradually straighten optic fiber 270 from a partially curved optic fiber 310 to a straightened optic fiber 300.

Illustratively, a surgeon may aim optic fiber distal end 271 at any of a plurality of targets within an eye, e.g., to perform a photocoagulation procedure. In one or more embodiments, a surgeon may aim optic fiber distal end 271 at any target within a particular transverse plane of the inner eye by, e.g., rotating handle 100 to orient shape memory sleeve 260 in an orientation configured to cause a curvature of optic fiber 270 within the particular transverse plane of the inner eye and varying an amount of compression of actuation structure 110. Illustratively, a surgeon may aim optic fiber distal end 271 at any target within a particular sagittal plane of the inner eye by, e.g., rotating handle 100 to orient shape memory sleeve 260 in an orientation configured to cause a curvature of optic fiber 270 within the particular sagittal plane of the inner eye and varying an amount of compression of actuation structure 110. In one or more embodiments, a surgeon may aim optic fiber distal end 271 at any target within a particular frontal plane of the inner eye by, e.g., varying an amount of compression of actuation structure 110 to orient a line tangent to optic fiber distal end 271 wherein the line tangent to optic fiber distal end 271 is within the particular frontal plane of the inner eye and rotating handle 100. Illustratively, a surgeon may aim optic fiber distal end 271 at any target located outside of the particular transverse plane, the particular sagittal plane, and the particular frontal plane of the inner eye, e.g., by varying a rotational orientation of handle 100 and varying an amount of compression of actuation structure 110.

Figure 5A:
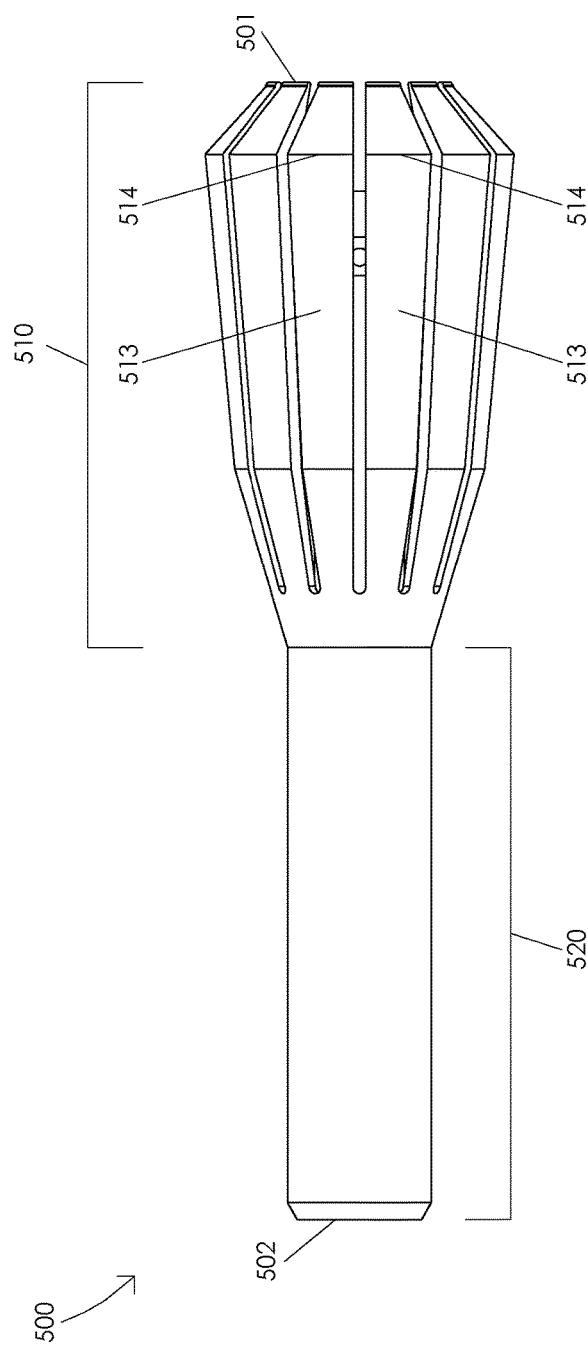
FIGS. 5A and 5B are schematic diagrams illustrating a handle.
Figure 5B:
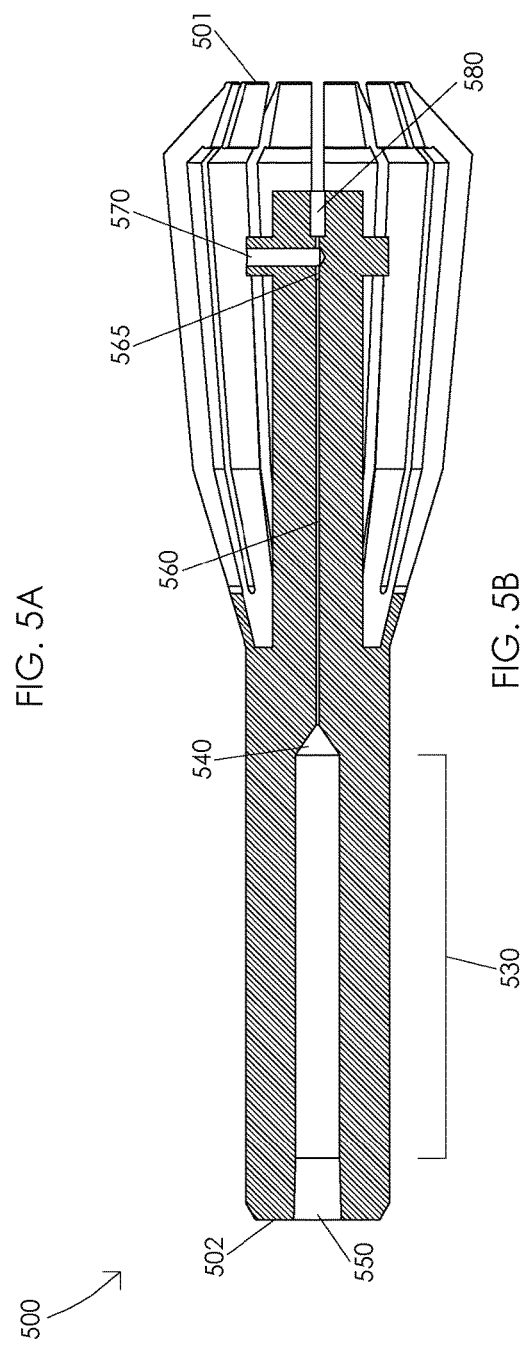

FIGS. 5A and 5B are schematic diagrams illustrating a handle 500. FIG. 5A illustrates a top view of handle 500. In one or more embodiments, handle 500 may comprise a handle distal end 501, a handle proximal end 502, an actuation structure 510, and a handle base 520. Illustratively, actuation structure 510 may comprise a plurality of actuation arms 513. In one or more embodiments, each actuation arm 513 may comprise at least one extension mechanism 514.

Illustratively, actuation structure 510 may be compressed by an application of a compressive force to actuation structure 510. In one or more embodiments, actuation structure 510 may be compressed by an application of one or more compressive forces located at one or more locations around an outer perimeter of actuation structure 510. Illustratively, the one or more locations may comprise any of a plurality of locations around the outer perimeter of actuation structure 510. For example, a surgeon may compress actuation structure 510 by squeezing actuation structure 510. Illustratively, the surgeon may compress actuation structure 510 by squeezing actuation structure 510 at any particular location of a plurality of locations around an outer perimeter of actuation structure 510. For example, a surgeon may rotate handle 500 and compress actuation structure 510 from any rotational position of a plurality of rotational positions of handle 500.

In one or more embodiments, actuation structure 510 may be compressed by an application of a compressive force to any one or more of the plurality of actuation arms 513. Illustratively, each actuation arm 513 may be configured to actuate independently. In one or more embodiments, each actuation arm 513 may be connected to one or more of the plurality of actuation arms 513 wherein an actuation of a particular actuation arm 513 may be configured to actuate every actuation arm 513 of the plurality of actuation arms 513. In one or more embodiments, a compression of actuation structure 510, e.g., due to an application of a compressive force to a particular actuation arm 513, may be configured to actuate the particular actuation arm 513. Illustratively, an actuation of the particular actuation arm 513 may be configured to actuate every actuation arm 513 of the plurality of actuation arms 513. In one or more embodiments, an application of a compressive force to a particular actuation arm 513 may be configured to extend at least one extension mechanism 514 of the particular actuation arm 513, e.g., relative to housing sleeve 250. Illustratively, a compression of a particular actuation arm 513 may be configured to extend at least one extension mechanism 514 relative to housing sleeve 250 by retracting housing sleeve 250 relative to handle 500.

FIG. 5B illustrates a cross-sectional view of handle 500. In one or more embodiments, handle 500 may comprise an inner bore 530, an inner bore distal cone 540, an inner bore proximal taper 550, an optic fiber guide 560, a shape memory sleeve guide 565, a fixation mechanism chamber 570, and a pressure mechanism housing 580. Handle 500 may be manufactured from any suitable material, e.g., polymers, metals, metal alloys, etc., or from any combination of suitable materials.

Figure 6:
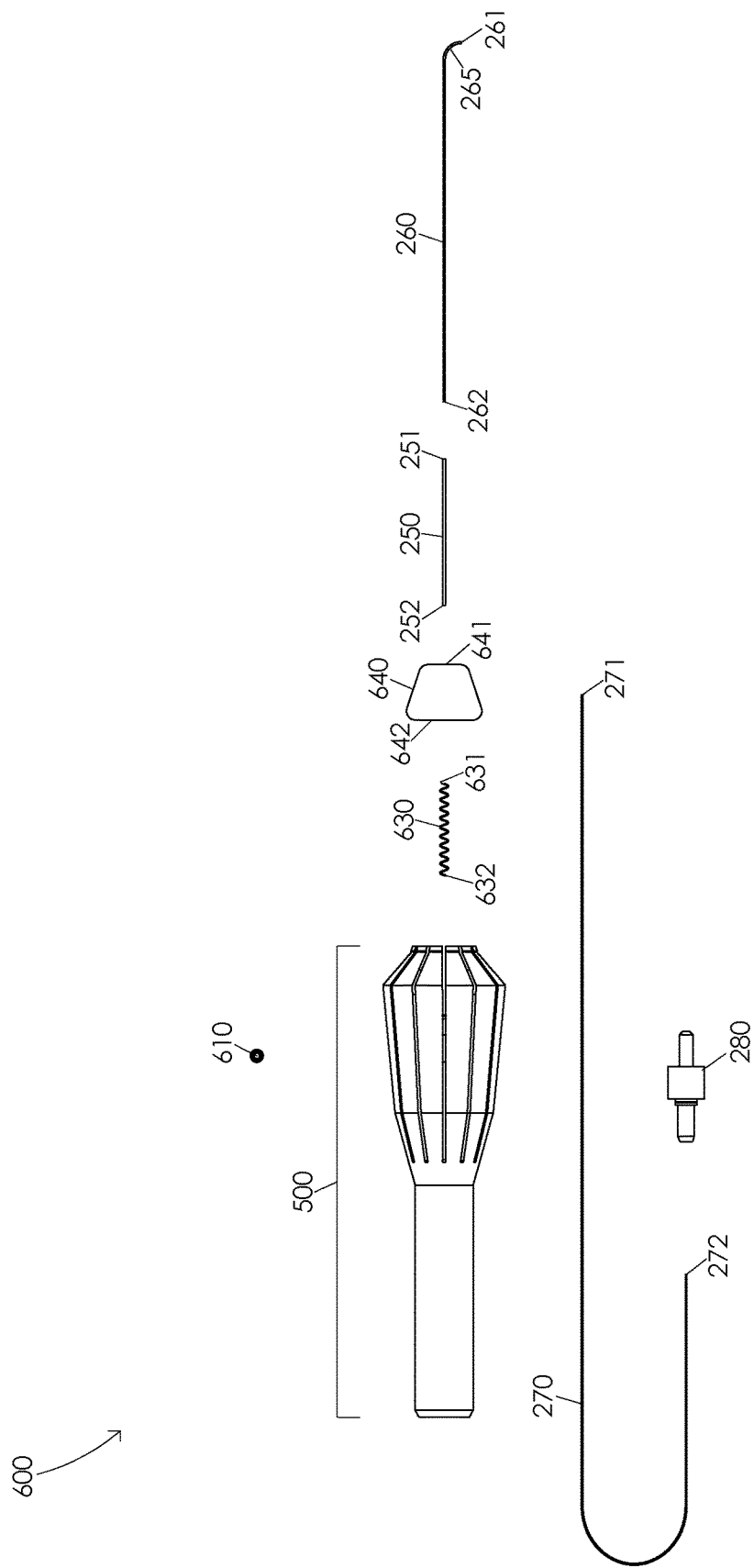
FIG. 6 illustrates an exploded view of a steerable laser probe assembly.

FIG. 6 illustrates an exploded view of a steerable laser probe assembly 600. In one or more embodiments, steerable laser probe assembly 600 may comprise a handle 500, a fixation mechanism 610, a pressure mechanism 630 having a pressure mechanism distal end 631 and a pressure mechanism proximal end 632, an actuation cone 640 having an actuation cone distal end 641 and an actuation cone proximal end 642, a housing sleeve 250 having a housing sleeve distal end 251 and a housing sleeve proximal end 252, a shape memory sleeve 260 having a shape memory sleeve distal end 261 and a shape memory sleeve proximal end 262, an optic fiber 270 having an optic fiber distal end 271 and an optic fiber proximal end 272, and a light source interface 280. Illustratively, housing sleeve proximal end 252 may be fixed to actuation cone distal end 641.

In one or more embodiments, pressure mechanism 630 may be disposed in pressure mechanism housing 580. Illustratively, actuation cone 640 may be at least partially disposed within actuation structure 510, e.g., wherein pressure mechanism distal end 631 abuts actuation cone proximal end 642. For example, actuation cone proximal end 642 may always be disposed within actuation structure 510. In one or more embodiments, a compression of actuation structure 510 may cause actuation cone 640 to be partially retracted into actuation structure 510. Illustratively, a decompression of actuation structure 510 may cause actuation cone 640 to be partially extended from actuation structure 510.

In one or more embodiments, pressure mechanism 630 may be configured to provide a force. Illustratively, pressure mechanism 630 may be configured to provide a force to resist a retraction of actuation cone 640 into actuation structure 510. For example, pressure mechanism 630 may be configured to provide a force to facilitate an extension of actuation cone 640 from actuation structure 510. In one or more embodiments, pressure mechanism 630 may comprise a spring. Illustratively, a compression of actuation structure 510 may cause a compression of pressure mechanism 630 and a decompression of actuation structure 510 may cause a decompression of pressure mechanism 630. Pressure mechanism 630 may be manufactured from any suitable material, e.g., polymers, metals, metal alloys, etc., or from any combination of suitable materials.

Illustratively, as actuation cone 640 is gradually retracted into actuation structure 510, e.g., due to a compression of actuation structure 510, housing sleeve 250 is also gradually retracted relative to handle 500. In one or more embodiments, as actuation cone 640 is gradually extended from actuation structure 510, e.g., due to a decompression of actuation structure 510, housing sleeve 250 is also gradually extended relative to handle 500. Illustratively, optic fiber 270 may be disposed within shape memory sleeve 260, e.g., such that optic fiber distal end 271 is adjacent to shape memory sleeve distal end 261. Optic fiber 270 may be fixed in a position within shape memory sleeve 260, e.g., with a biocompatible adhesive or any suitable fixation means. In one or more embodiments, optic fiber 270 may be disposed within inner bore 530 and optic fiber guide 560. Illustratively, optic fiber 270 and shape memory sleeve 260 may be disposed within shape memory sleeve guide 565, pressure mechanism housing 580, actuation cone 640, and housing sleeve 250. In one or more embodiments, optic fiber 270 and shape memory sleeve 260 may be disposed within pressure mechanism 630. Illustratively, optic fiber 270 and shape memory sleeve 260 may be held fixed relative to handle 500, e.g., by fixation mechanism 610, at fixation mechanism housing 570.

In one or more embodiments, a compression of actuation structure 510 may be configured to gradually expose optic fiber 270 and shape memory sleeve 260 from housing sleeve distal end 251. Illustratively, as actuation structure 510 is compressed, actuation cone 640 may be gradually retracted into actuation structure 510 and housing sleeve 250 may be gradually retracted relative optic fiber 270 and shape memory sleeve 260 to gradually expose optic fiber 270 and shape memory sleeve 260 from housing sleeve distal end 251. In one or more embodiments, as optic fiber 270 and shape memory sleeve 260 are gradually exposed by housing sleeve 250, shape memory sleeve 260 may gradually curve optic fiber 270 towards pre-bent angle 265.

In one or more embodiments, a decompression of actuation structure 510 may be configured to gradually extend housing sleeve 250 over optic fiber 270 and shape memory sleeve 260. Illustratively, as actuation structure 510 is decompressed, a portion of actuation cone 640 may be gradually extended from actuation structure 510 and housing sleeve 250 may be gradually extended relative to optic fiber 270 and shape memory sleeve 260. In one or more embodiments, as housing sleeve 250 is gradually extended over optic fiber 270 and shape memory sleeve 260, optic fiber 270 and shape memory sleeve 260 may be gradually straightened, e.g., as housing sleeve 250 gradually straightens pre-bent angle 265.

Figure 7A:
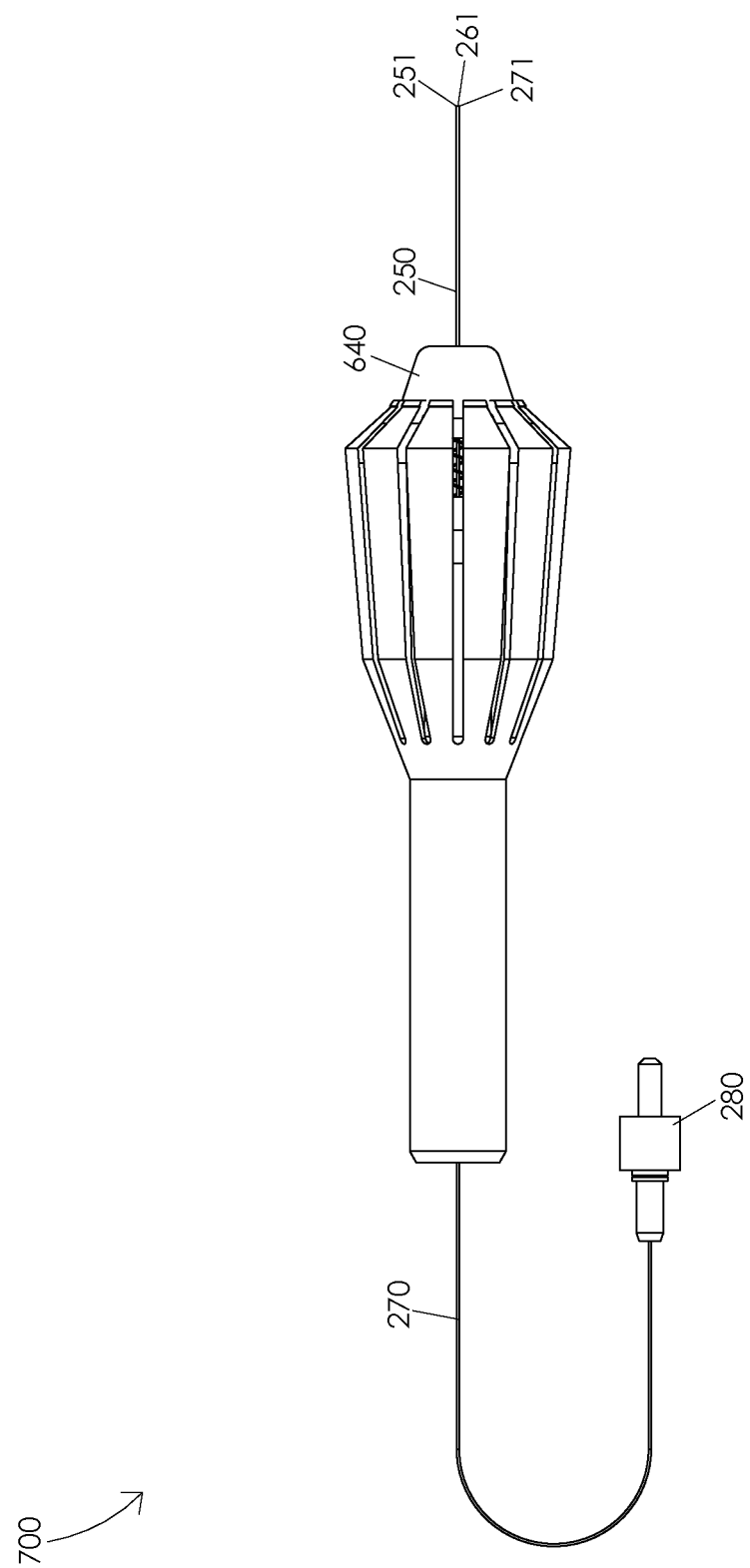
FIGS. 7A, 7B, and 7C illustrate a gradual curving of an optic fiber.
Figure 7B:
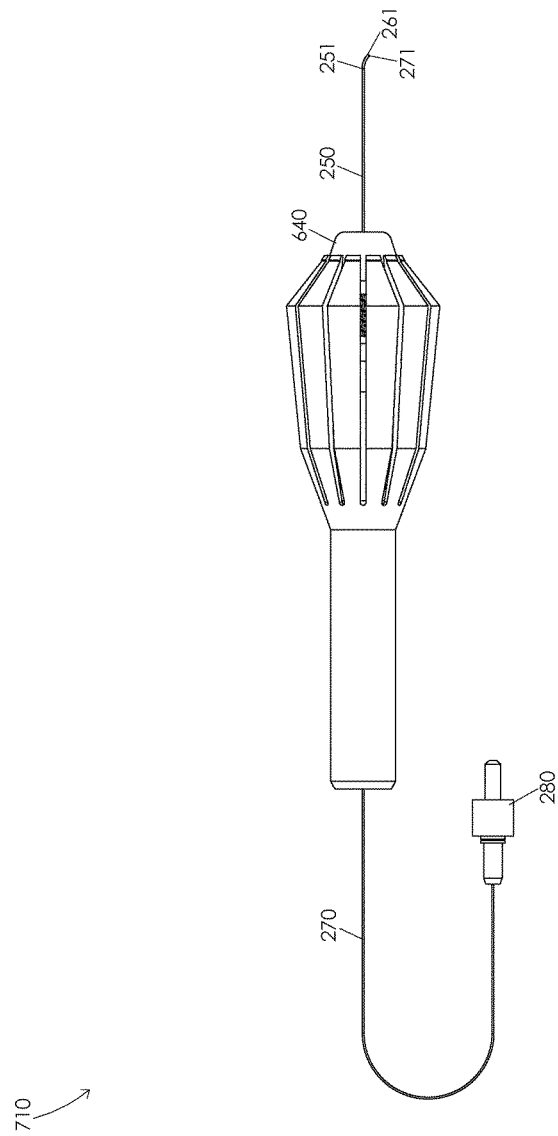
Figure 7C:
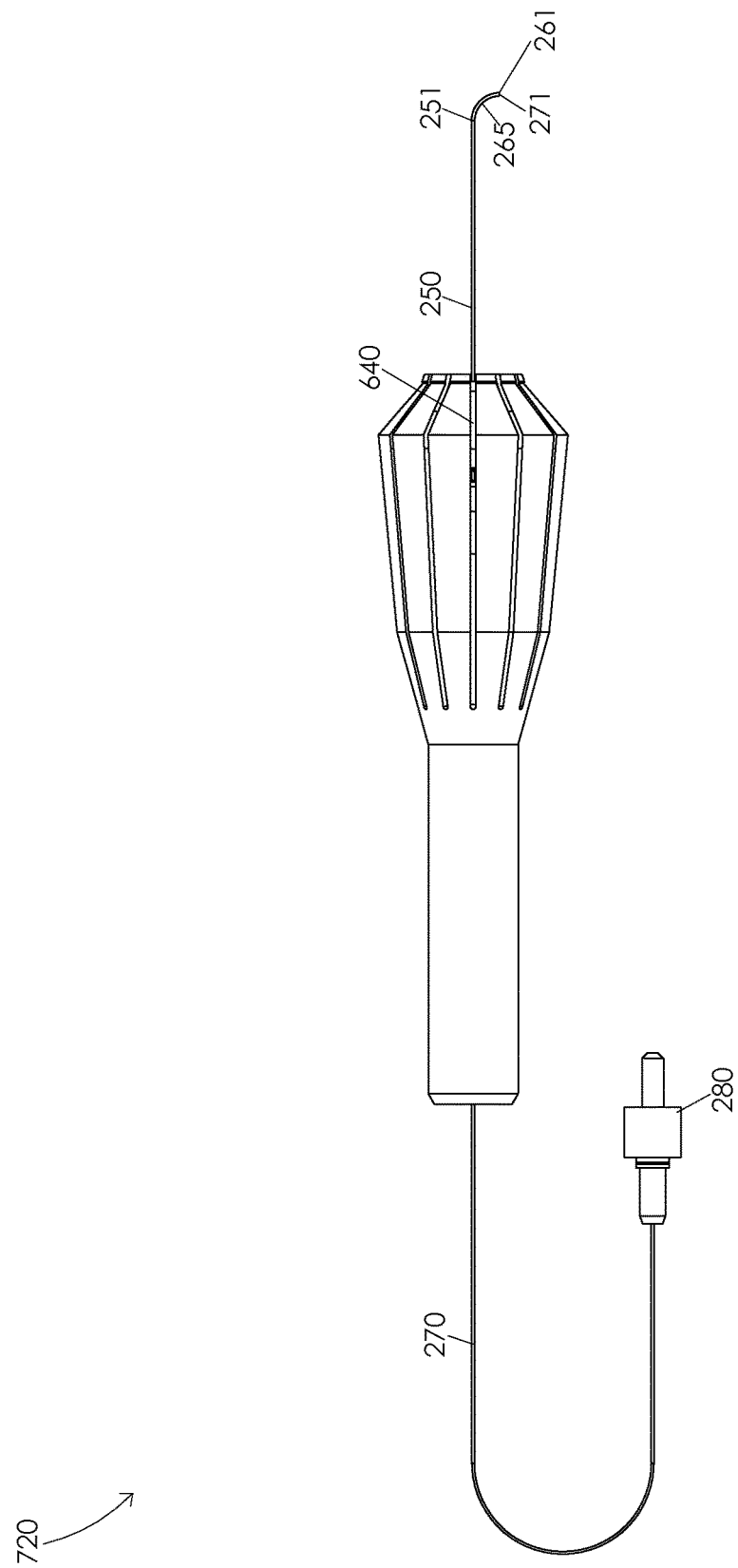

FIGS. 7A, 7B, and 7C illustrate a gradual curving of an optic fiber 270. FIG. 7A illustrates a straightened optic fiber 700. Illustratively, straightened optic fiber 700 is fully contained within housing sleeve 250. In one or more embodiments, optic fiber 270 and shape memory sleeve 260 may be fully contained within housing sleeve 250, e.g., when actuation structure 510 is fully decompressed. For example, when actuation structure 510 is fully decompressed, pressure mechanism 630 may extend actuation cone 640 from actuation structure 510. Illustratively, when optic fiber 270 and shape memory sleeve 260 are fully contained within housing sleeve 250, pre-bent angle 265 of shape memory sleeve 260 may be straightened by housing sleeve 250. For example, an angle between housing sleeve 250 and a line tangent to optic fiber distal end 271 may be, e.g., 180 degrees, when housing sleeve 250 contains a straightened optic fiber 700.

FIG. 7B illustrates a partially curved optic fiber 710. In one or more embodiments, a compression of a fully decompressed actuation structure 510 may be configured to gradually retract housing sleeve 250 relative to optic fiber 270 and shape memory sleeve 260 causing optic fiber 270 and shape memory sleeve 260 to be gradually exposed from housing sleeve distal end 251. For example, as actuation structure 510 is compressed, actuation cone 640 may be partially retracted into actuation structure 510. In one or more embodiments, pressure mechanism 630 may be configured to provide a resistive force to resist a retraction of actuation cone 640 into actuation structure 510. Illustratively, as optic fiber 270 and shape memory sleeve 260 are gradually exposed by a retraction of housing sleeve 250, shape memory sleeve 260 may cause optic fiber 270 to curve towards pre-bent angle 265. In one or more embodiments, a compression of actuation structure 510 may cause a straightened optic fiber 700 to gradually curve to a partially curved optic fiber 710.

Illustratively, a compression of actuation structure 510 may gradually expose optic fiber 270 and shape memory sleeve 260 from housing sleeve distal end 251 as housing sleeve 250 is gradually retracted. As housing sleeve 250 is gradually retracted shape memory sleeve 260 may cause optic fiber 270 to gradually curve towards pre-bent angle 265. For example, as an exposed length of optic fiber 270 and shape memory sleeve 260 is increased, e.g., by a retraction of housing sleeve 250, an angle between housing sleeve 250 and a line tangent to optic fiber distal end 271 may be decreased.

Illustratively, optic fiber 270 and shape memory sleeve 260 may be exposed from housing sleeve 250 at a first length with a first angle between housing sleeve 250 and a line tangent to optic fiber distal end 271. A retraction of housing sleeve 250, e.g., due to a compression of actuation structure 510, may expose optic fiber 270 and shape memory sleeve 260 from housing sleeve 250 at a second length with a second angle between housing sleeve 250 and a line tangent to optic fiber distal end 271. Illustratively, the second length may be greater than the first length and the second angle may be less than the first angle.

FIG. 7C illustrates a fully curved optic fiber 720. Illustratively, when housing sleeve 250 is fully retracted, e.g., by a full compression of actuation structure 510, housing sleeve 250 may expose a fully curved optic fiber 720. For example, as actuation structure 510 is fully compressed, actuation cone 640 may be fully retracted into actuation structure 510. In one or more embodiments, pressure mechanism 630 may be configured to provide a resistive force to resist a retraction of actuation cone 640 into actuation structure 510. In one or more embodiments, a compression of actuation structure 510 may cause a partially curved optic fiber 710 to gradually curve to a fully curved optic fiber 720. Illustratively, when housing sleeve 250 is retracted to expose a partially curved optic fiber 710, optic fiber 270 and shape memory sleeve 260 may be exposed from housing sleeve 250 at a partially extended length with a partially extended angle between housing sleeve 250 and a line tangent to optic fiber distal end 271. A retraction of housing sleeve 250, e.g., due to a full compression of actuation structure 510, may expose optic fiber 270 and shape memory sleeve 260 from housing sleeve 250 at fully extended length with a fully extended angle between housing sleeve 250 and a line tangent to optic fiber distal end 271, e.g., when housing sleeve 250 is retracted to expose a fully curved optic fiber 720. Illustratively, the fully extended length may be greater than the partially extended length and the fully extended angle may be less than the partially extended angle.

In one or more embodiments, one or more properties of a steerable laser probe may be adjusted to attain one or more desired steerable laser probe features. For example, a length that housing sleeve 250 extends from actuation cone distal end 641 may be adjusted to vary an amount of compression of actuation structure 510 configured to expose a particular length of optic fiber 270 and shape memory sleeve 260 from housing sleeve distal end 251. Illustratively, a position of fixation mechanism chamber 570 and fixation mechanism 610 or a length of optic fiber 270 and shape memory sleeve 260 extending distally from a position of fixation mechanism 610 may be adjusted to vary an amount of compression of actuation structure 510 configured to expose a particular length of optic fiber 270 and shape memory sleeve 260 from housing sleeve distal end 251. In one or more embodiments, a geometry of actuation structure 510 or a geometry of actuation cone 640 may be adjusted to vary an amount of compression of actuation structure 510 configured to expose a particular length of optic fiber 270 and shape memory sleeve 260 from housing sleeve distal end 251. For example, one or more properties of pressure mechanism 630 may be adjusted to vary an amount of force configured to compress actuation structure 510. Illustratively, a magnitude of pre-bent angle 265 may be adjusted to vary a magnitude of an angle between housing sleeve 250 and a line tangent to optic fiber distal end 271 when a particular length of optic fiber 270 and shape memory sleeve 260 is exposed from housing sleeve distal end 251.

Figure 8A:
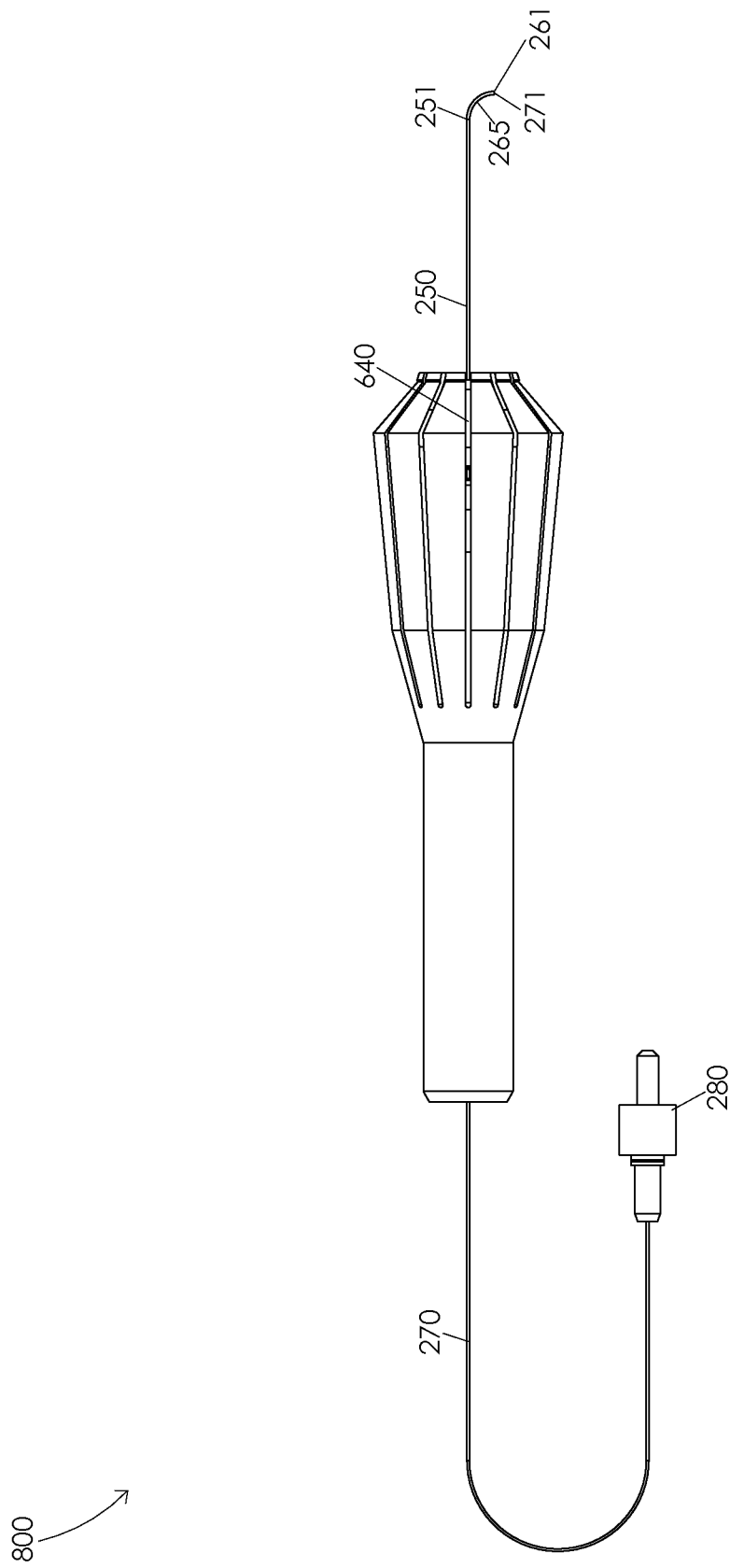
Figure 8C:
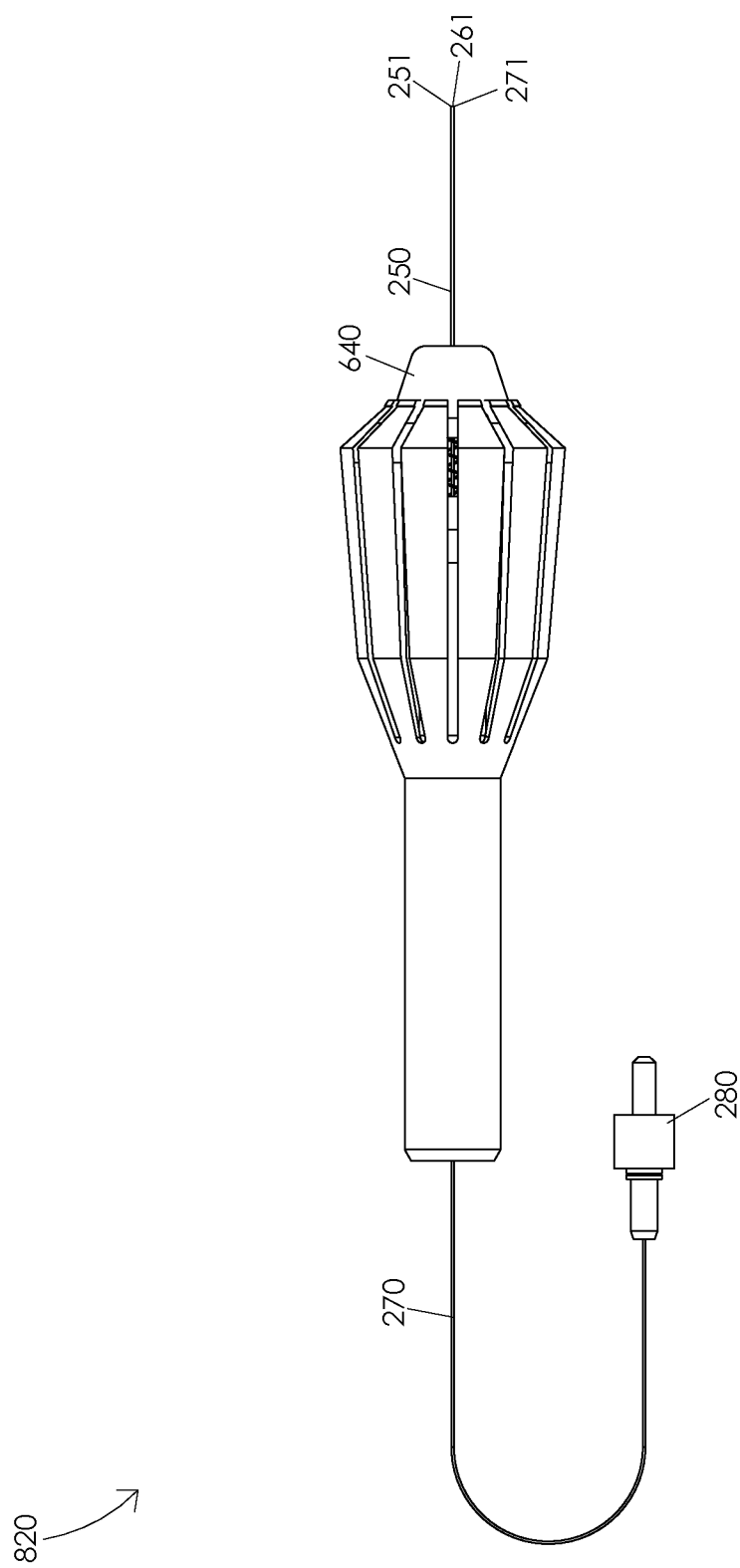

FIGS. 8A, 8B, and 8C illustrate a gradual straightening of an optic fiber 270. FIG. 8A illustrates a retracted housing sleeve 800. Illustratively, a refracted housing sleeve 800 may expose at least a portion of optic fiber 270 and shape memory sleeve 260 from housing sleeve distal end 251. In one or more embodiments, a full compression of actuation structure 510 may cause housing sleeve 250 to actuate relative to optic fiber 270 and shape memory sleeve 260 such that a fully curved optic fiber 720 is exposed from housing sleeve distal end 251. Illustratively, housing sleeve 250 may comprise a retracted housing sleeve 800, e.g., due to a full compression of actuation structure 510. For example, as actuation structure 510 is fully compressed, actuation cone 640 may be fully retracted into actuation structure 510.

FIG. 8B illustrates a partially extended housing sleeve 810. Illustratively, a partially extended housing sleeve 810 may hold a portion of pre-bent angle 265 in a straightened position within housing sleeve 250. In one or more embodiments, a decompression of actuation structure 510 may extend housing sleeve 250 over optic fiber 270 and shape memory sleeve 260 causing shape memory sleeve 260 to gradually straighten optic fiber 270 from a fully curved optic fiber 720 to a partially curved optic fiber 710. For example, as actuation structure 510 is decompressed, actuation cone 640 may be partially extended from actuation structure 510. In one or more embodiments, pressure mechanism 630 may be configured to provide a facilitating force to facilitate an extension of actuation cone 640 from actuation structure 510.

FIG. 8C illustrates a fully extended housing sleeve 820. Illustratively, a fully extended housing sleeve 820 may hold pre-bent angle 265 in a straightened position within housing sleeve 250. In one or more embodiments, a full decompression of actuation structure 510 may extend housing sleeve 250 over optic fiber 270 and shape memory sleeve 260 causing shape memory sleeve 260 to gradually straighten optic fiber 270 from a partially curved optic fiber 710 to a straightened optic fiber 700. For example, as actuation structure 510 is fully decompressed, actuation cone 640 may be fully extended from actuation structure 510. In one or more embodiments, pressure mechanism 630 may be configured to provide a facilitating force to facilitate an extension of actuation cone 640 from actuation structure 510.

Illustratively, a surgeon may aim optic fiber distal end 271 at any of a plurality of targets within an eye, e.g., to perform a photocoagulation procedure. In one or more embodiments, a surgeon may aim optic fiber distal end 271 at any target within a particular transverse plane of the inner eye by, e.g., rotating handle 500 to orient shape memory sleeve 260 in an orientation configured to cause a curvature of optic fiber 270 within the particular transverse plane of the inner eye and varying an amount of compression of actuation structure 510. Illustratively, a surgeon may aim optic fiber distal end 271 at any target within a particular sagittal plane of the inner eye by, e.g., rotating handle 500 to orient shape memory sleeve 260 in an orientation configured to cause a curvature of optic fiber 270 within the particular sagittal plane of the inner eye and varying an amount of compression of actuation structure 510. In one or more embodiments, a surgeon may aim optic fiber distal end 271 at any target within a particular frontal plane of the inner eye by, e.g., varying an amount of compression of actuation structure 510 to orient a line tangent to optic fiber distal end 271 wherein the line tangent to optic fiber distal end 271 is within the particular frontal plane of the inner eye and rotating handle 500. Illustratively, a surgeon may aim optic fiber distal end 271 at any target located outside of the particular transverse plane, the particular sagittal plane, and the particular frontal plane of the inner eye, e.g., by varying a rotational orientation of handle 500 and varying an amount of compression of actuation structure 510.

Figure 9A:
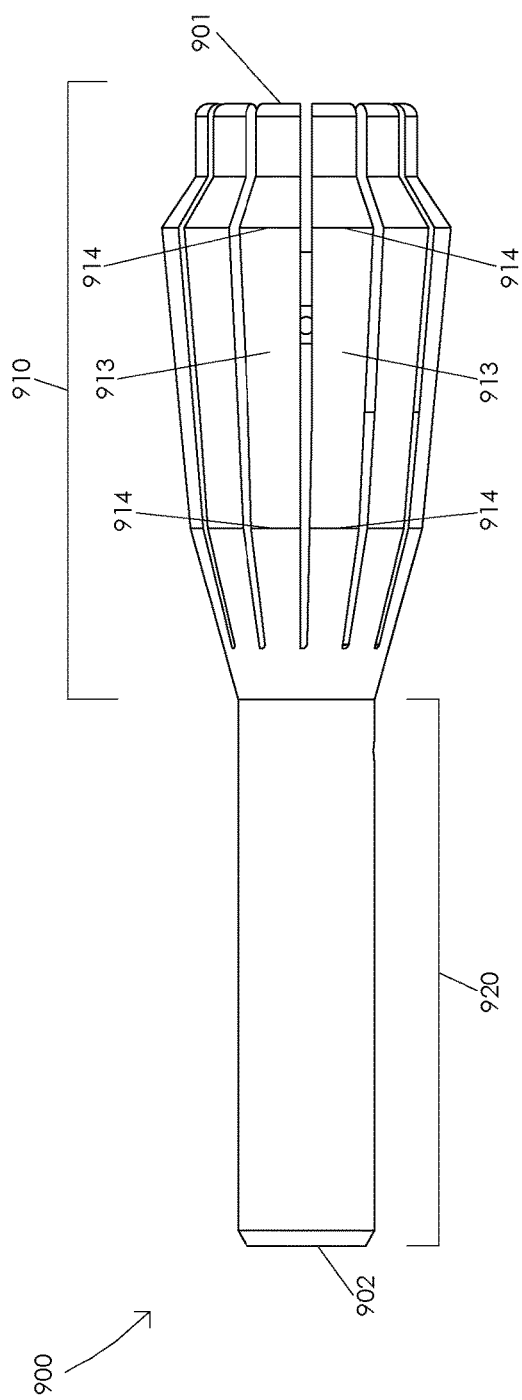
FIGS. 9A and 9B are schematic diagrams illustrating a handle.
Figure 9B:
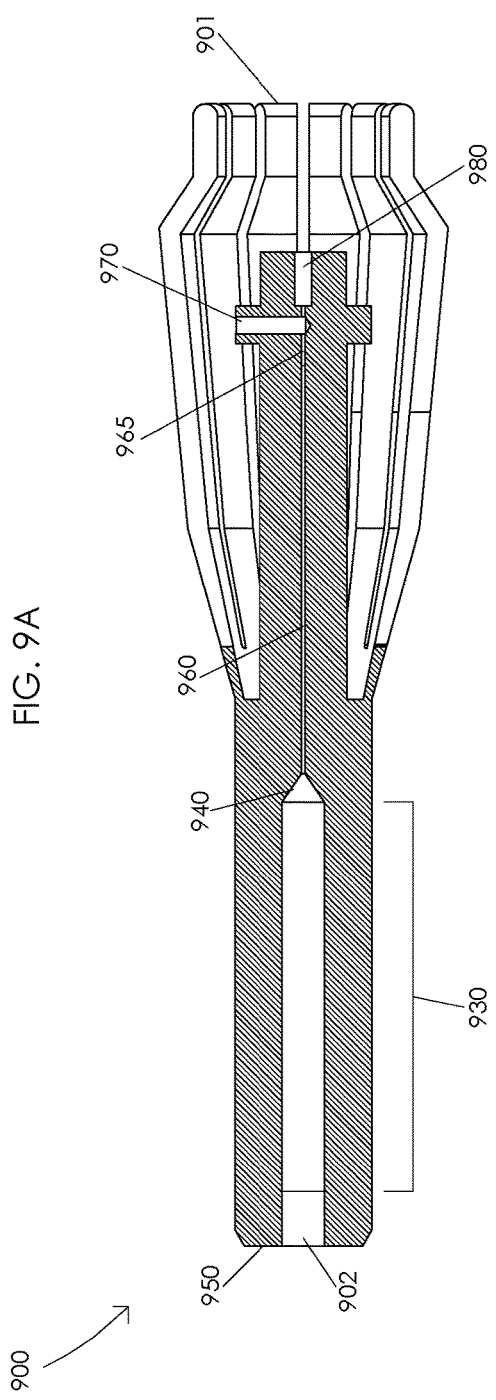

FIGS. 9A and 9B are schematic diagrams illustrating a handle 900. FIG. 9A illustrates a top view of handle 900. In one or more embodiments, handle 900 may comprise a handle distal end 901, a handle proximal end 902, an actuation structure 910, and a handle base 920. Illustratively, actuation structure 910 may comprise a plurality of actuation arms 913. In one or more embodiments, each actuation arm 913 may comprise at least one extension mechanism 914.

Illustratively, actuation structure 910 may be compressed by an application of a compressive force to actuation structure 910. In one or more embodiments, actuation structure 910 may be compressed by an application of one or more compressive forces located at one or more locations around an outer perimeter of actuation structure 910. Illustratively, the one or more locations may comprise any of a plurality of locations around the outer perimeter of actuation structure 910. For example, a surgeon may compress actuation structure 910 by squeezing actuation structure 910. Illustratively, the surgeon may compress actuation structure 910 by squeezing actuation structure 910 at any particular location of a plurality of locations around an outer perimeter of actuation structure 910. For example, a surgeon may rotate handle 900 and compress actuation structure 910 from any rotational position of a plurality of rotational positions of handle 900.

In one or more embodiments, actuation structure 910 may be compressed by an application of a compressive force to any one or more of the plurality of actuation arms 913. Illustratively, each actuation arm 913 may be configured to actuate independently. In one or more embodiments, each actuation arm 913 may be connected to one or more of the plurality of actuation arms 913 wherein an actuation of a particular actuation arm 913 may be configured to actuate every actuation arm 913 of the plurality of actuation arms 913. In one or more embodiments, a compression of actuation structure 910, e.g., due to an application of a compressive force to a particular actuation arm 913, may be configured to actuate the particular actuation arm 913. Illustratively, an actuation of the particular actuation arm 913 may be configured to actuate every actuation arm 913 of the plurality of actuation arms 913. In one or more embodiments, an application of a compressive force to a particular actuation arm 913 may be configured to extend at least one extension mechanism 914 of the particular actuation arm 913. Illustratively, a particular actuation arm 913 may extend a first length from handle base 920. An extension of an extension mechanism 914 of the particular actuation arm 913, e.g., due to an application of a compressive force to the particular actuation arm 913, may be configured to extend the particular actuation arm a second length from handle base 920. Illustratively, the second length from handle base 920 may be greater than the first length from handle base 920.

FIG. 9B illustrates a cross-sectional view of handle 900. In one or more embodiments, handle 900 may comprise an inner bore 930, an inner bore distal cone 940, an inner bore proximal taper 950, an optic fiber guide 960, a shape memory sleeve guide 965, a fixation mechanism chamber 970, and a piston tube proximal housing 980. Handle 900 may be manufactured from any suitable material, e.g., polymers, metals, metal alloys, etc., or from any combination of suitable materials.

Figure 10A:
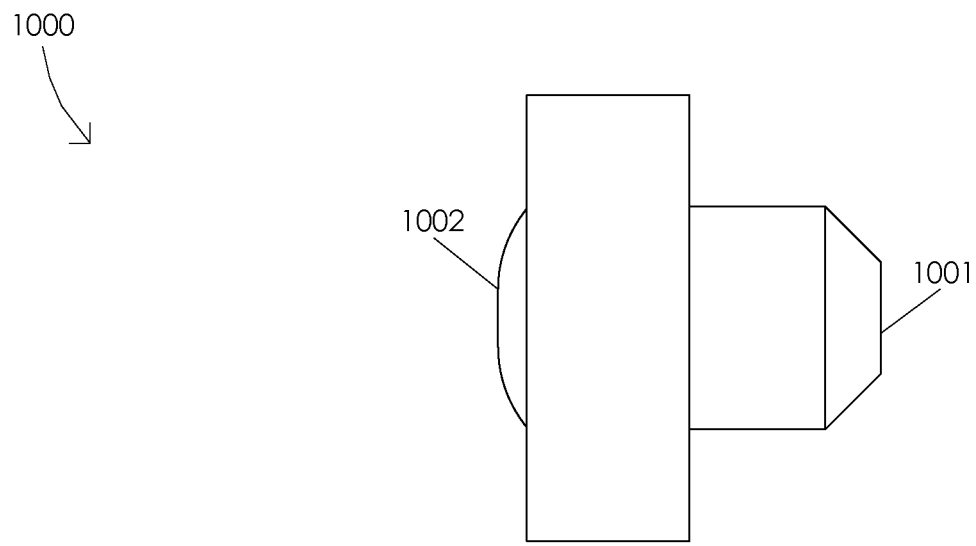
FIGS. 10A and 10B are schematic diagrams illustrating an actuation nosecone.
Figure 10B:
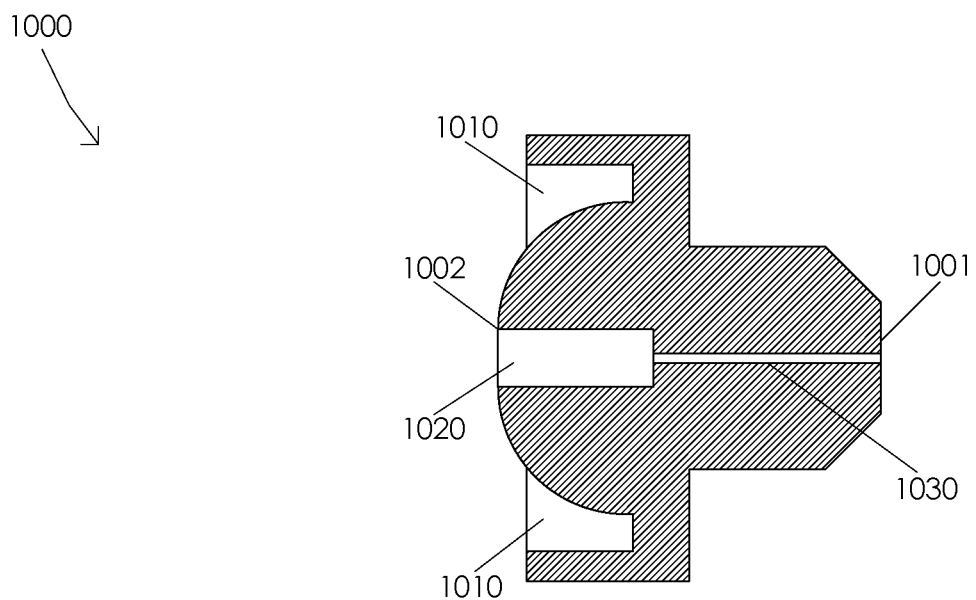

FIGS. 10A and 10B are schematic diagrams illustrating an actuation nosecone 1000. FIG. 10A is a schematic diagram illustrating a top view of actuation nosecone 1000. Illustratively, actuation nosecone 1000 comprises an actuation nosecone distal end 1001 and an actuation nosecone proximal end 1002. FIG. 10B is a schematic diagram illustrating a cross-sectional view of actuation nosecone 1000. In one or more embodiments, actuation nosecone 1000 may comprise an actuation structure interface 1010, a piston tube distal housing 1020, and a shape memory sleeve distal guide 1030.

Figure 11:
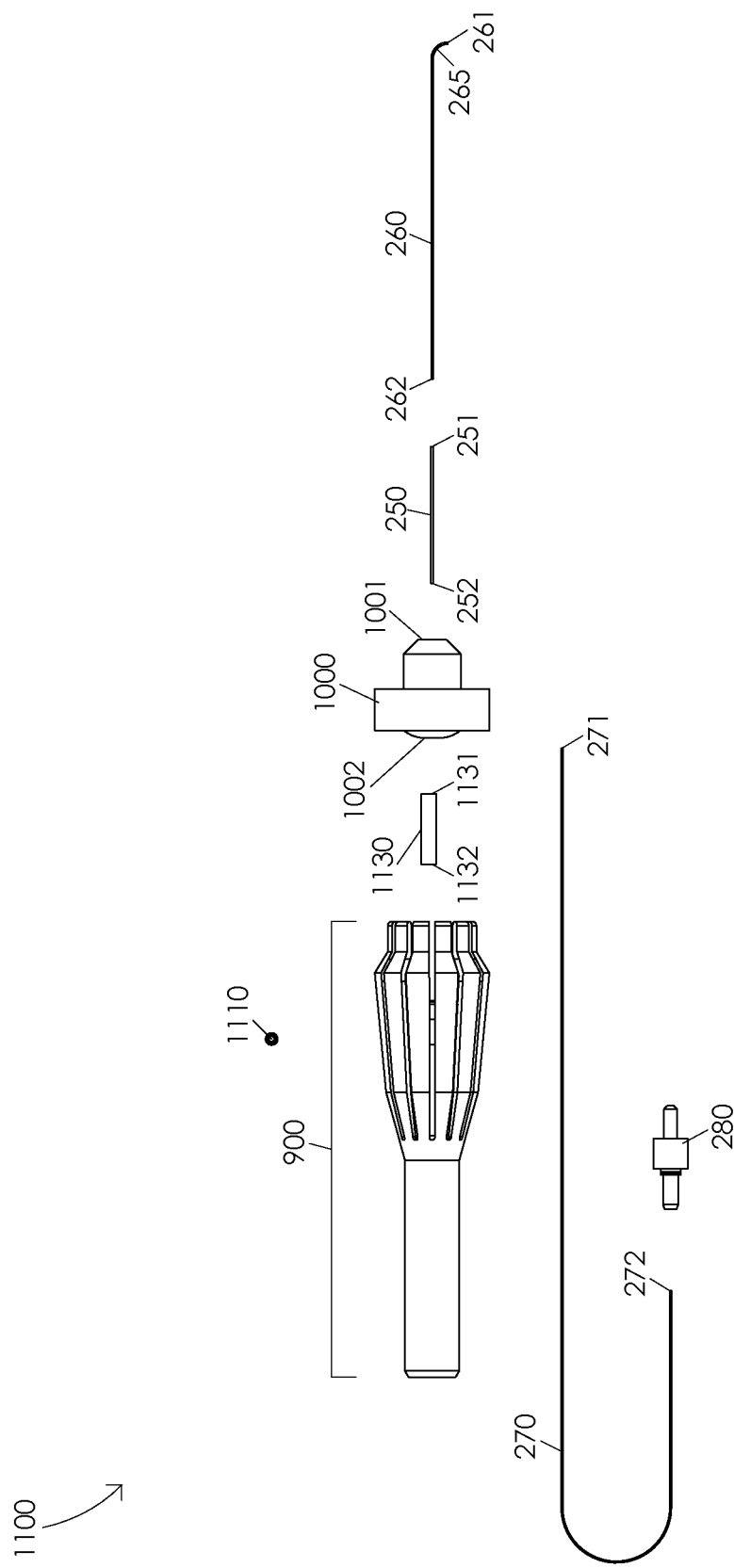
FIG. 11 illustrates an exploded view of a steerable laser probe assembly.

FIG. 11 illustrates an exploded view of a steerable laser probe assembly 1100. In one or more embodiments, steerable laser probe assembly 1100 may comprise a handle 900, a fixation mechanism 1110, a piston tube 1130 having a piston tube distal end 1131 and a piston tube proximal end 1132, an actuation nosecone 1000, a housing sleeve 250 having a housing sleeve distal end 251 and a housing sleeve proximal end 252, a shape memory sleeve 260 having a shape memory sleeve distal end 261 and a shape memory sleeve proximal end 262, an optic fiber 270 having an optic fiber distal end 271 and an optic fiber proximal end 272, and a light source interface 280. Illustratively, housing sleeve proximal end 252 may be fixed to actuation nosecone distal end 1001.

In one or more embodiments, piston tube 1130 may be disposed between piston tube distal housing 1020 and piston tube proximal housing 980. Illustratively, piston tube distal end 1131 may be fixed to actuation nosecone proximal end 1002. In one or more embodiments, handle distal end 901 may be configured to interface with actuation structure interface 1010 wherein a compression of actuation structure 910 may extend actuation nosecone 1000 relative to handle 900. Illustratively, handle distal end 901 may be configured to interface with actuation structure interface 1010 wherein a decompression of actuation structure 910 may retract actuation nosecone 1000 relative to handle 900.

Illustratively, optic fiber 270 may be disposed within shape memory sleeve 260, e.g., such that optic fiber distal end 271 is adjacent to shape memory sleeve distal end 261. Optic fiber 270 may be fixed in a position within shape memory sleeve 260, e.g., with a biocompatible adhesive or any suitable fixation means. In one or more embodiments, optic fiber 270 may be disposed within inner bore 930 and optic fiber guide 960. Illustratively, optic fiber 270 and shape memory sleeve 260 may be disposed within shape memory sleeve guide 965, piston tube proximal housing 980, piston tube 1130, piston tube distal housing 1020, shape memory sleeve distal guide 1030, and housing sleeve 250. Illustratively, optic fiber 270 and shape memory sleeve 260 may be held fixed relative to handle 900, e.g., by fixation mechanism 1110, at fixation mechanism housing 970.

In one or more embodiments, a decompression of actuation structure 910 may be configured to cause housing sleeve 250 to be refracted relative to optic fiber 270 and shape memory sleeve 260. Illustratively, a decompression of actuation structure 910 may be configured to retract actuation nosecone 1000 and housing sleeve 250 relative to handle 900. In one or more embodiments, a decompression of actuation structure 910 may be configured to cause housing sleeve 250 to be gradually refracted relative to optic fiber 270 and shape memory sleeve 260 wherein optic fiber 270 and shape memory sleeve 260 may be gradually exposed from housing sleeve distal end 251. In one or more embodiments, as optic fiber 270 and shape memory sleeve 260 are gradually exposed by housing sleeve 250, shape memory sleeve 260 may gradually curve optic fiber 270 towards pre-bent angle 265.

In one or more embodiments, a compression of actuation structure 910 may be configured to cause housing sleeve 250 to be extended relative to optic fiber 270 and shape memory sleeve 260. Illustratively, a compression of actuation structure 910 may be configured to extend actuation nosecone 1000 and housing sleeve 250 relative to handle 900. In one or more embodiments, a compression of actuation structure 910 may be configured to cause housing sleeve 250 to be gradually extended relative to optic fiber 270 and shape memory sleeve 260 wherein optic fiber 270 and shape memory sleeve 260 may be gradually covered by housing sleeve 250. In one or more embodiments, as housing sleeve 250 is gradually extended over optic fiber 270 and shape memory sleeve 260, optic fiber 270 and shape memory sleeve 260 may be gradually straightened, e.g., as housing sleeve 250 gradually straightens pre-bent angle 265.

Figure 12A:
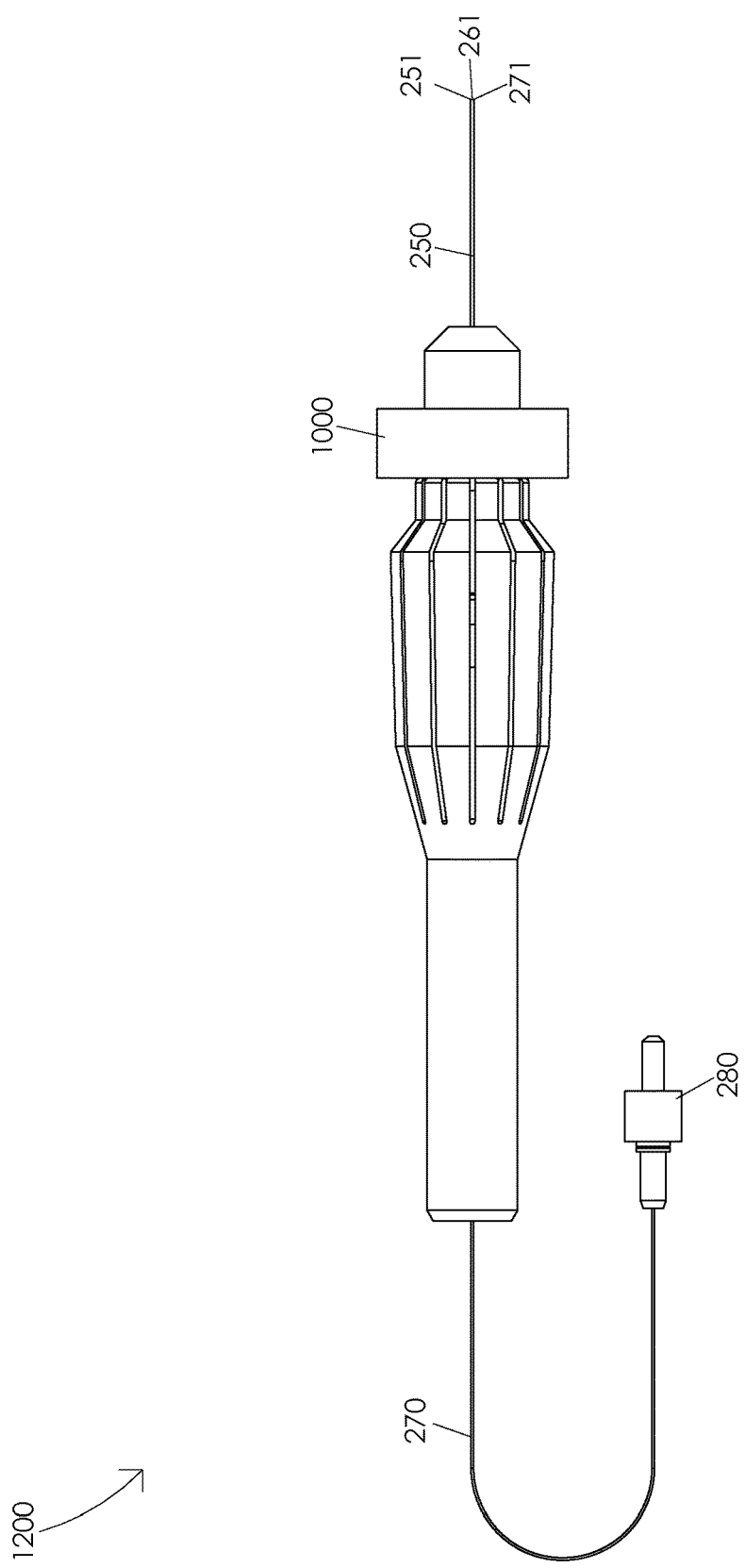
Figure 12B:
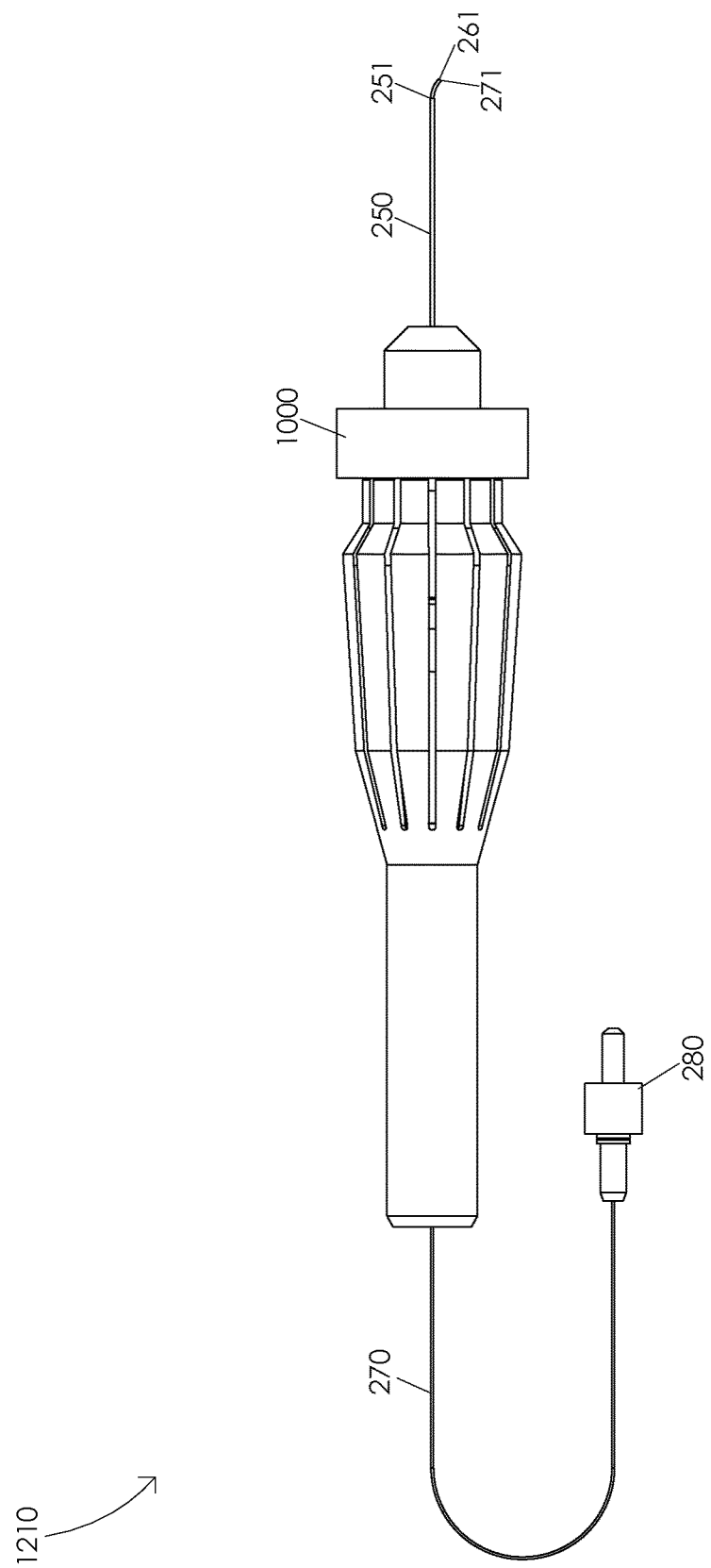

FIGS. 12A, 12B, and 12C illustrate a gradual curving of an optic fiber 270. FIG. 12A illustrates a straightened optic fiber 1200. Illustratively, straightened optic fiber 1200 is fully contained within housing sleeve 250. In one or more embodiments, optic fiber 270 and shape memory sleeve 260 may be fully contained within housing sleeve 250, e.g., when actuation structure 910 is fully compressed. For example, when actuation structure 910 is fully compressed, actuation nosecone 1000 may be fully extended relative to handle 900. Illustratively, when optic fiber 270 and shape memory sleeve 260 are fully contained within housing sleeve 250, pre-bent angle 265 of shape memory sleeve 260 may be straightened by housing sleeve 250. For example, an angle between housing sleeve 250 and a line tangent to optic fiber distal end 271 may be, e.g., 180 degrees, when housing sleeve 250 contains a straightened optic fiber 1200.

FIG. 12B illustrates a partially curved optic fiber 1210. In one or more embodiments, a decompression of a fully compressed actuation structure 910 may gradually retract housing sleeve 250 to expose optic fiber 270 and shape memory sleeve 260. For example, as actuation structure 910 is decompressed, actuation nosecone 1000 may be refracted relative to handle 900. Illustratively, as optic fiber 270 and shape memory sleeve 260 are gradually exposed by a refraction of housing sleeve 250, shape memory sleeve 260 may cause optic fiber 270 to curve towards pre-bent angle 265. In one or more embodiments, a decompression of actuation structure 910 may cause a straightened optic fiber 1200 to gradually curve to a partially curved optic fiber 1210. Illustratively, a decompression of actuation structure 910 may gradually expose optic fiber 270 and shape memory sleeve 260 causing optic fiber 270 to gradually curve towards pre-bent angle 265. For example, as an exposed length of optic fiber 270 and shape memory sleeve 260 is increased, e.g., by a retraction of housing sleeve 250, an angle between housing sleeve 250 and a line tangent to optic fiber distal end 271 may be decreased. Illustratively, optic fiber 270 and shape memory sleeve 260 may be exposed from housing sleeve distal end 251 at a first length with a first angle between housing sleeve 250 and a line tangent to optic fiber distal end 271. A retraction of housing sleeve 250, e.g., due to a decompression of actuation structure 910, may expose optic fiber 270 and shape memory sleeve 260 from housing sleeve distal end 251 at a second length with a second angle between housing sleeve 250 and a line tangent to optic fiber distal end 271. Illustratively, the second length may be greater than the first length and the second angle may be less than the first angle.

FIG. 12C illustrates a fully curved optic fiber 1220. Illustratively, when housing sleeve 250 is fully retracted, e.g., by a full decompression of actuation structure 910, housing sleeve 250 may expose a fully curved optic fiber 1220. For example, when actuation structure 910 is fully decompressed, actuation nosecone 1000 may be fully retracted relative to handle 900. In one or more embodiments, a decompression of actuation structure 910 may cause a partially curved optic fiber 1210 to gradually curve to a fully curved optic fiber 1220. Illustratively, when housing sleeve 250 is retracted to expose a partially curved optic fiber 1210, optic fiber 270 and shape memory sleeve 260 may be exposed from housing sleeve distal end 251 at a partially extended length with a partially extended angle between housing sleeve 250 and a line tangent to optic fiber distal end 271. A retraction of housing sleeve 250, e.g., due to a full decompression of actuation structure 910, may expose optic fiber 270 and shape memory sleeve 260 from housing sleeve distal end 251 at fully extended length with a fully extended angle between housing sleeve 250 and a line tangent to optic fiber distal end 271, e.g., when housing sleeve 250 is retracted to expose a fully curved optic fiber 1220. Illustratively, the fully extended length may be greater than the partially extended length and the fully extended angle may be less than the partially extended angle.

In one or more embodiments, one or more properties of a steerable laser probe may be adjusted to attain one or more desired steerable laser probe features. For example, a length that housing sleeve 250 extends from actuation nosecone distal end 1001 may be adjusted to vary an amount of decompression of actuation structure 910 configured to expose a particular length of optic fiber 270 and shape memory sleeve 260 from housing sleeve distal end 251. Illustratively, a position of fixation mechanism chamber 970 and fixation mechanism 1110 or a length of optic fiber 270 and shape memory sleeve 260 extending distally from a position of fixation mechanism 1110 may be adjusted to vary an amount of decompression of actuation structure 910 configured to expose a particular length of optic fiber 270 and shape memory sleeve 260 from housing sleeve distal end 251. In one or more embodiments, a geometry of actuation structure 910 or a geometry of actuation nosecone 1000 may be adjusted to vary an amount of decompression of actuation structure 910 configured to expose a particular length of optic fiber 270 and shape memory sleeve 260 from housing sleeve distal end 251. Illustratively, a magnitude of pre-bent angle 265 may be adjusted to vary a magnitude of an angle between housing sleeve 250 and a line tangent to optic fiber distal end 271 when a particular length of optic fiber 270 and shape memory sleeve 260 is exposed from housing sleeve distal end 251.

Figure 13A:
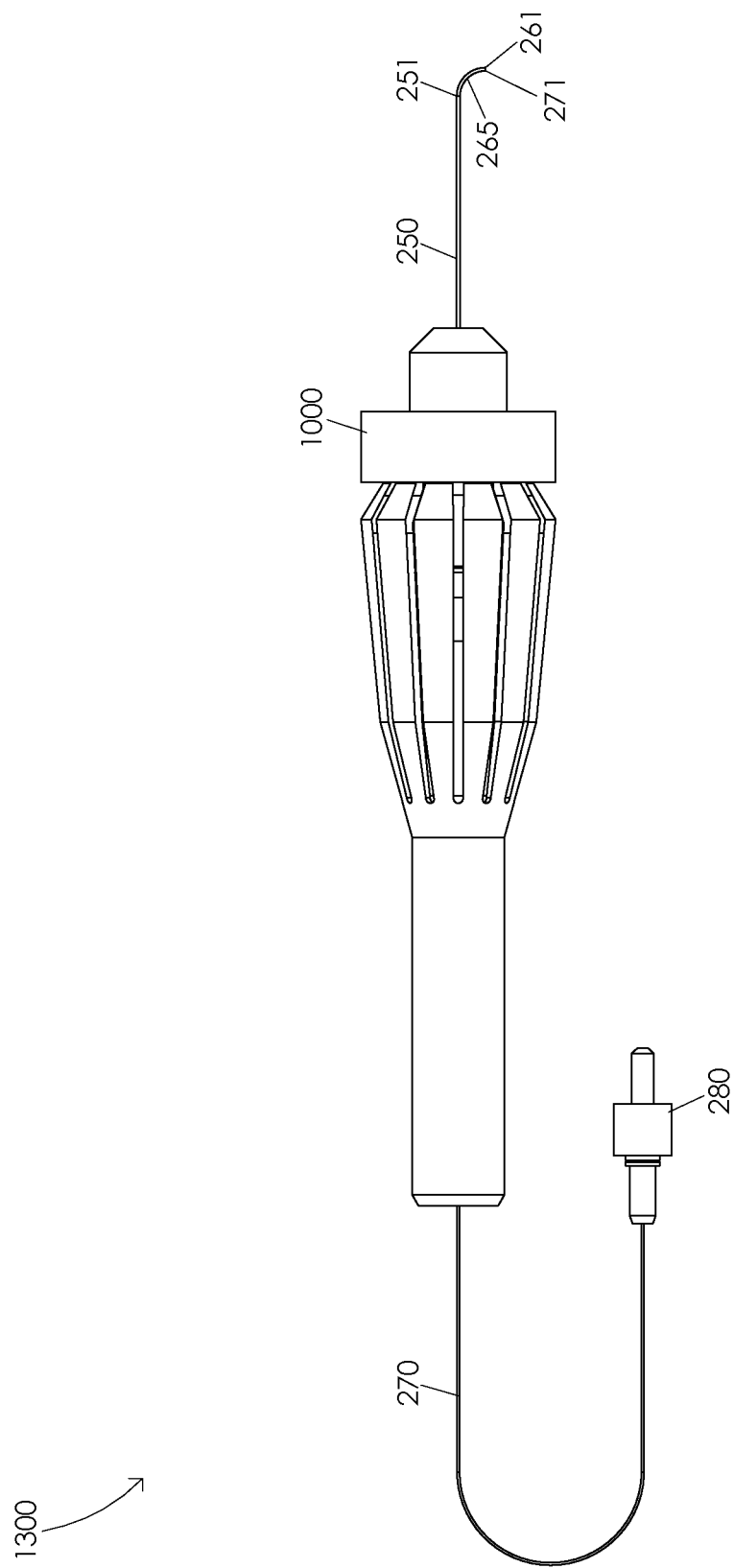
FIGS. 13A, 13B, and 13C illustrate a gradual straightening of an optic fiber.
Figure 13B:
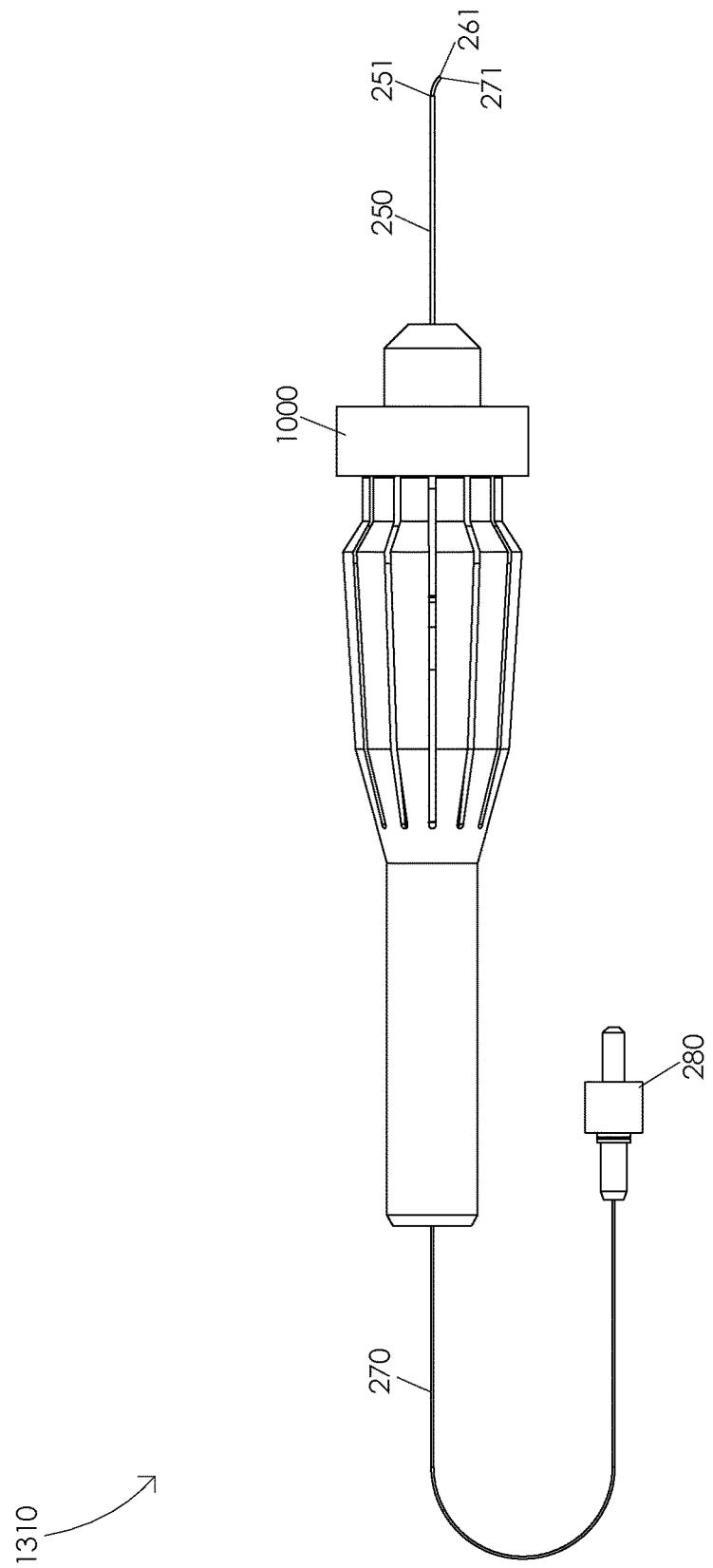
Figure 13C:
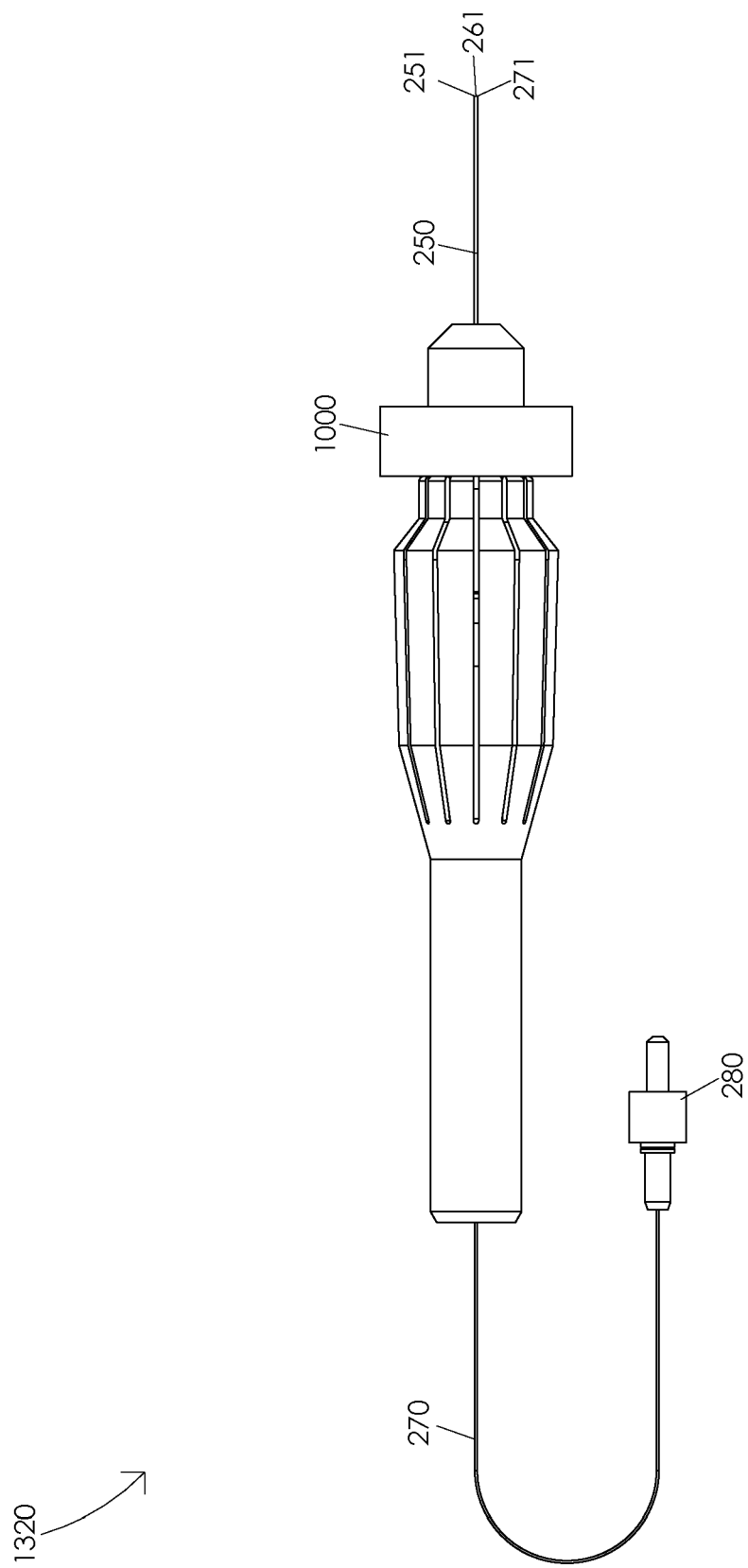

FIGS. 13A, 13B, and 13C illustrate a gradual straightening of an optic fiber 270. FIG. 13A illustrates a retracted housing sleeve 1300. Illustratively, a retracted housing sleeve 1300 may expose at least a portion of optic fiber 270 and shape memory sleeve 260 from housing sleeve distal end 251. In one or more embodiments, a full decompression of actuation structure 910 may be configured to cause housing sleeve 250 to be retracted relative to optic fiber 270 and shape memory sleeve 260 such that a fully curved optic fiber 1220 is exposed from housing sleeve distal end 251. Illustratively, housing sleeve 250 may comprise a retracted housing sleeve 1300, e.g., due to a full decompression of actuation structure 910. For example, when actuation structure 910 is fully decompressed, actuation nosecone 1000 may be fully retracted relative to handle 900.

FIG. 13B illustrates a partially extended housing sleeve 1310. Illustratively, a partially extended housing sleeve 1310 may hold a portion of pre-bent angle 265 in a straightened position within housing sleeve 250. In one or more embodiments, a compression of actuation structure 910 may extend housing sleeve 250 over optic fiber 270 and shape memory sleeve 260 causing shape memory sleeve 260 to gradually straighten optic fiber 270 from a fully curved optic fiber 1220 to a partially curved optic fiber 1210. For example, a compression of a fully decompressed actuation structure 910 may partially extend actuation nosecone 1000 relative to handle 900.

FIG. 13C illustrates a fully extended housing sleeve 1320. Illustratively, a fully extended housing sleeve 1320 may hold pre-bent angle 265 in a straightened position within housing sleeve 250. In one or more embodiments, a full compression of actuation structure 910 may extend housing sleeve 250 over optic fiber 270 and shape memory sleeve 260 causing shape memory sleeve 260 to gradually straighten optic fiber 270 from a partially curved optic fiber 1210 to a straightened optic fiber 1200. For example, when actuation structure 910 is fully compressed, actuation nosecone 1000 may be fully extended relative to handle 900.

Illustratively, a surgeon may aim optic fiber distal end 271 at any of a plurality of targets within an eye, e.g., to perform a photocoagulation procedure. In one or more embodiments, a surgeon may aim optic fiber distal end 271 at any target within a particular transverse plane of the inner eye by, e.g., rotating handle 900 to orient shape memory sleeve 260 in an orientation configured to cause a curvature of optic fiber 270 within the particular transverse plane of the inner eye and varying an amount of compression of actuation structure 910. Illustratively, a surgeon may aim optic fiber distal end 271 at any target within a particular sagittal plane of the inner eye by, e.g., rotating handle 900 to orient shape memory sleeve 260 in an orientation configured to cause a curvature of optic fiber 270 within the particular sagittal plane of the inner eye and varying an amount of compression of actuation structure 910. In one or more embodiments, a surgeon may aim optic fiber distal end 271 at any target within a particular frontal plane of the inner eye by, e.g., varying an amount of compression of actuation structure 910 to orient a line tangent to optic fiber distal end 271 wherein the line tangent to optic fiber distal end 271 is within the particular frontal plane of the inner eye and rotating handle 900. Illustratively, a surgeon may aim optic fiber distal end 271 at any target located outside of the particular transverse plane, the particular sagittal plane, and the particular frontal plane of the inner eye, e.g., by varying a rotational orientation of handle 900 and varying an amount of compression of actuation structure 910.

FIGS. 14A and 14B are schematic diagrams illustrating a handle 1400. FIG. 14A illustrates a top view of handle 1400. In one or more embodiments, handle 1400 may comprise a handle distal end 1401, a handle proximal end 1402, a handle base 1405, an actuation structure 1410, an actuation ring 1415, a platform base 1420, an actuation mechanism guide 1421, and a housing sleeve platform 1425. Illustratively, actuation structure 1410 may comprise an actuation structure distal end 1411 and an actuation structure proximal end 1412. In one or more embodiments, actuation structure 1410 may comprise a plurality of actuation arms 1413. Illustratively, each actuation arm 1413 may comprise at least one extension mechanism 1414.

Illustratively, actuation structure 1410 may be compressed by an application of a compressive force to actuation structure 1410. In one or more embodiments, actuation structure 1410 may be compressed by an application of one or more compressive forces located at one or more locations around an outer perimeter of actuation structure 1410. Illustratively, the one or more locations may comprise any of a plurality of locations around the outer perimeter of actuation structure 1410. For example, a surgeon may compress actuation structure 1410 by squeezing actuation structure 1410. Illustratively, the surgeon may compress actuation structure 1410 by squeezing actuation structure 1410 at any particular location of a plurality of locations around an outer perimeter of actuation structure 1410. For example, a surgeon may rotate handle 1400 and compress actuation structure 1410 from any rotational position of a plurality of rotational positions of handle 1400.

In one or more embodiments, actuation structure 1410 may be compressed by an application of a compressive force to any one or more of the plurality of actuation arms 1413. Illustratively, each actuation arm 1413 may be configured to actuate independently. In one or more embodiments, each actuation arm 1413 may be connected to one or more of the plurality of actuation arms 1413 wherein an actuation of a particular actuation arm 1413 may be configured to actuate every actuation arm 1413 of the plurality of actuation arms 1413. In one or more embodiments, a compression of actuation structure 1410, e.g., due to an application of a compressive force to a particular actuation arm 1413, may be configured to actuate the particular actuation arm 1413. Illustratively, an actuation of the particular actuation arm 1413 may be configured to actuate every actuation arm 1413 of the plurality of actuation arms 1413. In one or more embodiments, an application of a compressive force to a particular actuation arm 1413 may be configured to extend at least one extension mechanism 1414 of the particular actuation arm 1413. Illustratively, a particular actuation arm 1413 may extend a first length from handle base 1405. An extension of an extension mechanism 1414 of the particular actuation arm 1413, e.g., due to an application of a compressive force to the particular actuation arm 1413, may be configured to extend the particular actuation arm a second length from handle base 1405. Illustratively, the second length from handle base 1405 may be greater than the first length from handle base 1405.

FIG. 14B illustrates a cross-sectional view of handle 1400. In one or more embodiments, handle 1400 may comprise an inner bore 1430, an inner bore distal cone 1440, an inner bore proximal taper 1450, an optic fiber guide 1460, a shape memory sleeve guide 1465, an actuation mechanism housing 1470, an actuation guide 1480, and a shape memory sleeve distal guide 1490. Handle 1400 may be manufactured from any suitable material, e.g., polymers, metals, metal alloys, etc., or from any combination of suitable materials.

Figure 15:
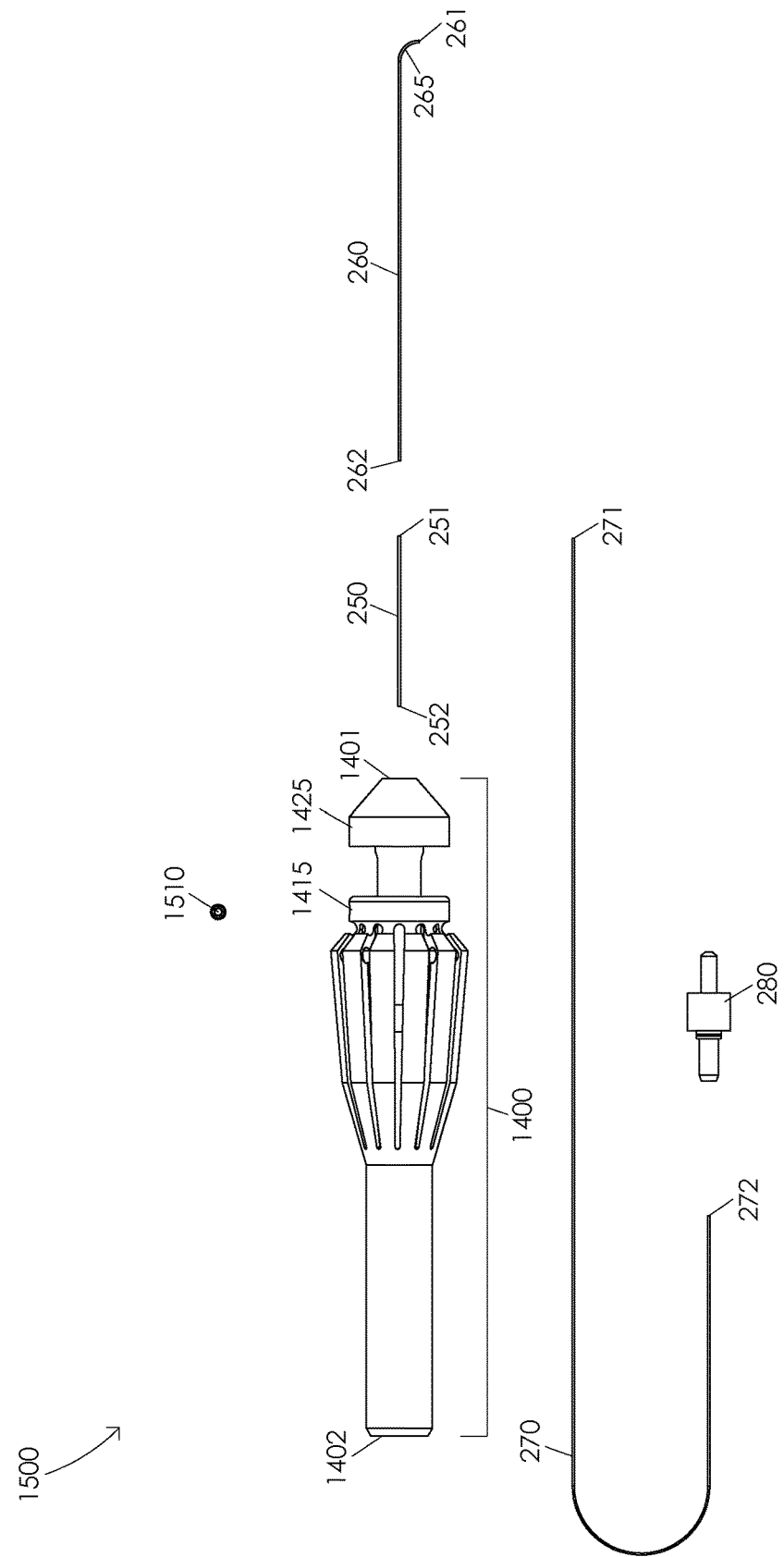
FIG. 15 illustrates an exploded view of a steerable laser probe assembly.

FIG. 15 illustrates an exploded view of a steerable laser probe assembly 1500. In one or more embodiments, steerable laser probe assembly 1500 may comprise a handle 1400, an actuation mechanism 1510, a housing sleeve 250 having a housing sleeve distal end 251 and a housing sleeve proximal end 252, a shape memory sleeve 260 having a shape memory sleeve distal end 261 and a shape memory sleeve proximal end 262, an optic fiber 270 having an optic fiber distal end 271 and an optic fiber proximal end 272, and a light source interface 280. Illustratively, housing sleeve proximal end 252 may be fixed to housing sleeve platform 1425 at handle distal end 1401.

In one or more embodiments, actuation ring 1415 may be fixed to actuation structure distal end 1411. Illustratively, a compression of action structure 1410 may be configured to extend actuation ring 1415, e.g., away from handle proximal end 1402 and towards handle distal end 1401. In one or more embodiments, a decompression of actuation structure 1410 may be configured to retract actuation ring 1415, e.g., away from handle distal end 1401 and towards handle proximal end 1402. Illustratively, actuation mechanism 1510 may be disposed within actuation mechanism housing 1470. In one or more embodiments, a compression of actuation structure 1410 may be configured to actuate actuation mechanism 1510 within actuation mechanism guide 1421, e.g., away from handle proximal end 1402 and towards handle distal end 1401. Illustratively, a decompression of actuation structure 1410 may be configured to actuate actuation mechanism 1510 within actuation mechanism guide 1421, e.g., away from handle distal end 1401 and towards handle proximal end 1402.

Illustratively, optic fiber 270 may be disposed within shape memory sleeve 260, e.g., such that optic fiber distal end 271 is adjacent to shape memory sleeve distal end 261. Optic fiber 270 may be fixed in a position within shape memory sleeve 260, e.g., with a biocompatible adhesive or any suitable fixation means. In one or more embodiments, optic fiber 270 may be disposed within inner bore 1430 and optic fiber guide 1460. Illustratively, optic fiber 270 and shape memory sleeve 260 may be disposed within shape memory sleeve guide 1465, actuation guide 1480, shape memory sleeve distal guide 1490, and housing sleeve 250. In one or more embodiments, optic fiber 270 and shape memory sleeve 260 may be disposed in actuation mechanism housing 1470. Illustratively, optic fiber 270 and shape memory sleeve 260 may be attached to actuation mechanism 1510 wherein an actuation of actuation mechanism 1510 may be configured to actuate optic fiber 270 and shape memory sleeve 260. For example, an actuation of actuation mechanism 1510 within actuation mechanism guide 1421 may be configured to actuate optic fiber 270 and shape memory sleeve 260 relative to housing sleeve 250.

Illustratively, platform base 1420, housing sleeve platform 1425, and housing sleeve 250 may be fixed in a position relative to handle base 1405. In one or more embodiments, an actuation of actuation mechanism 1510 within actuation mechanism guide 1421, i.e., away from handle proximal end 1402 and towards handle distal end 1401, may be configured to extend optic fiber 270 and shape memory sleeve 260 out of housing sleeve 250. Illustratively, an actuation of actuation mechanism 1510 within actuation mechanism guide 1421, i.e., away from handle distal end 1401 and towards handle proximal end 1402, may be configured to retract optic fiber 270 and shape memory sleeve 260 into housing sleeve 250.

In one or more embodiments, a compression of actuation structure 1410 may be configured to actuate optic fiber 270 and shape memory sleeve 260 relative to housing sleeve 250 wherein optic fiber 270 and shape memory sleeve 260 may be gradually extended from housing sleeve distal end 251. Illustratively, as optic fiber 270 and shape memory sleeve 260 are gradually extended from housing sleeve 250, e.g., due to a compression of actuation structure 1410, shape memory sleeve 260 may gradually curve optic fiber 270 towards pre-bent angle 265. In one or more embodiments, a decompression of actuation structure 1410 may be configured actuate optic fiber 270 and shape memory sleeve 260 relative to housing sleeve 250 wherein optic fiber 270 and shape memory sleeve 260 are gradually retracted into housing sleeve distal end 251. Illustratively, as optic fiber 270 and shape memory sleeve 260 are gradually retracted into housing sleeve 250, e.g., due to a decompression of actuation structure 1410, shape memory sleeve 260 may gradually straighten optic fiber 270 as housing sleeve 250 straightens pre-bent angle 265. In one or more embodiments, an interior portion of housing sleeve 250 may be coated with a lubrication material configured to facilitate actuation of shape memory sleeve 260 and optic fiber 270 relative to housing sleeve 250. Illustratively, the lubrication material may comprise any suitable material, e.g., Teflon.

Figure 16A:
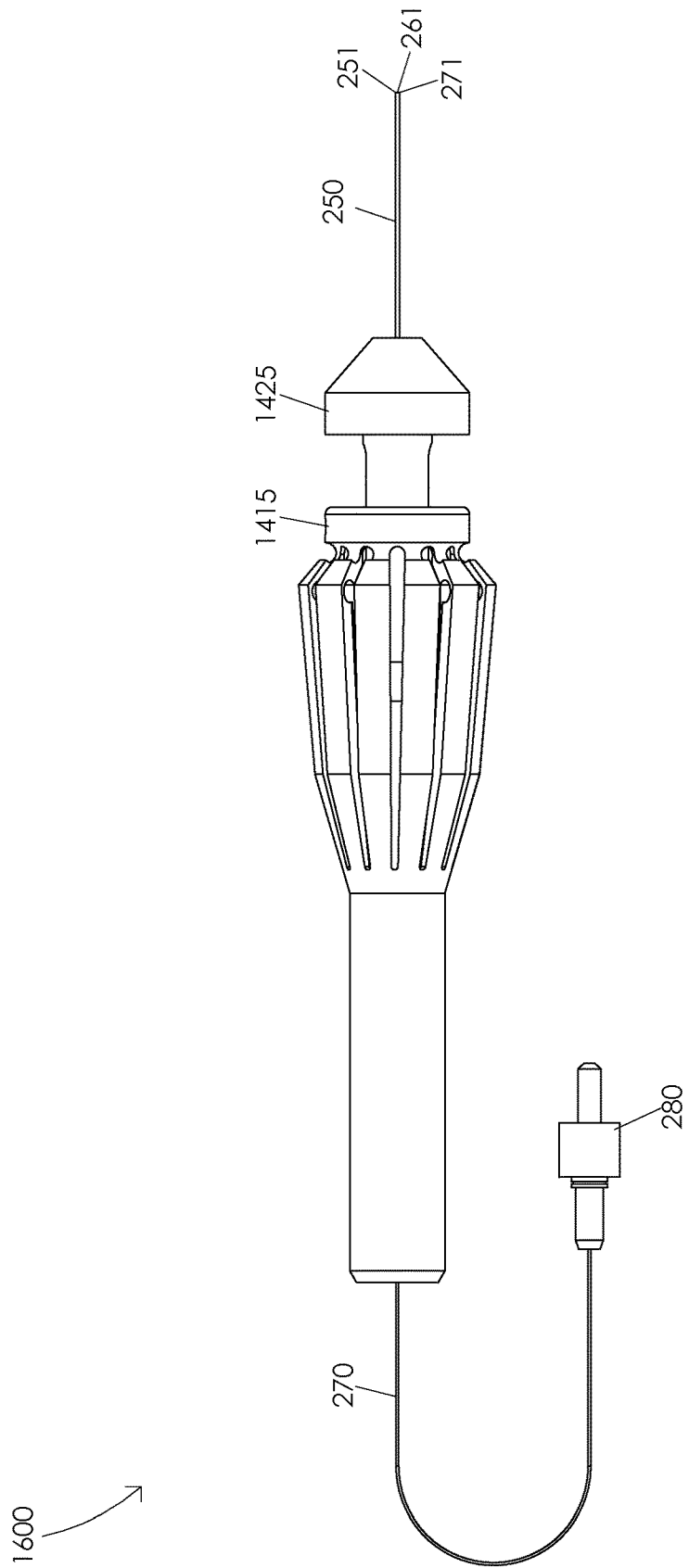
FIGS. 16A, 16B, and 16C illustrate a gradual curving of an optic fiber.
Figure 16B:
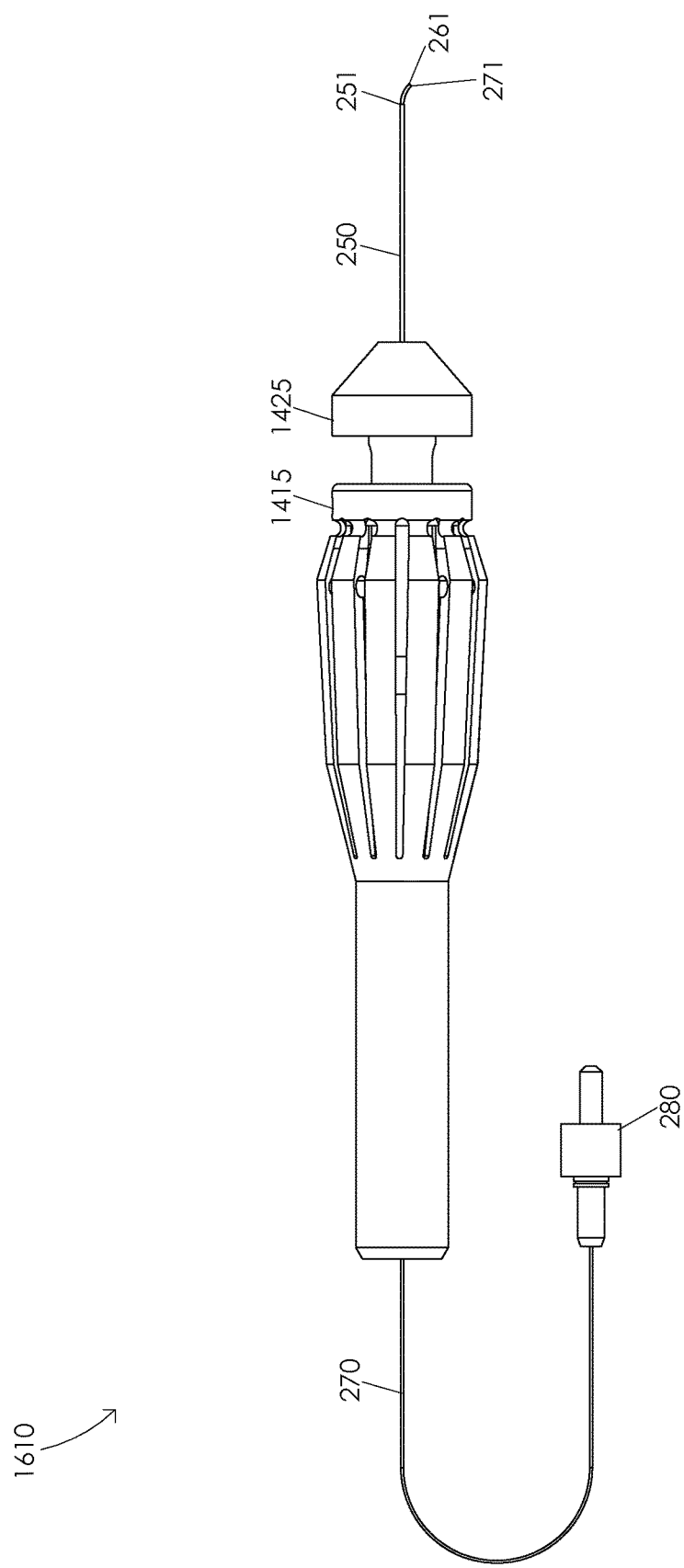
Figure 16C:
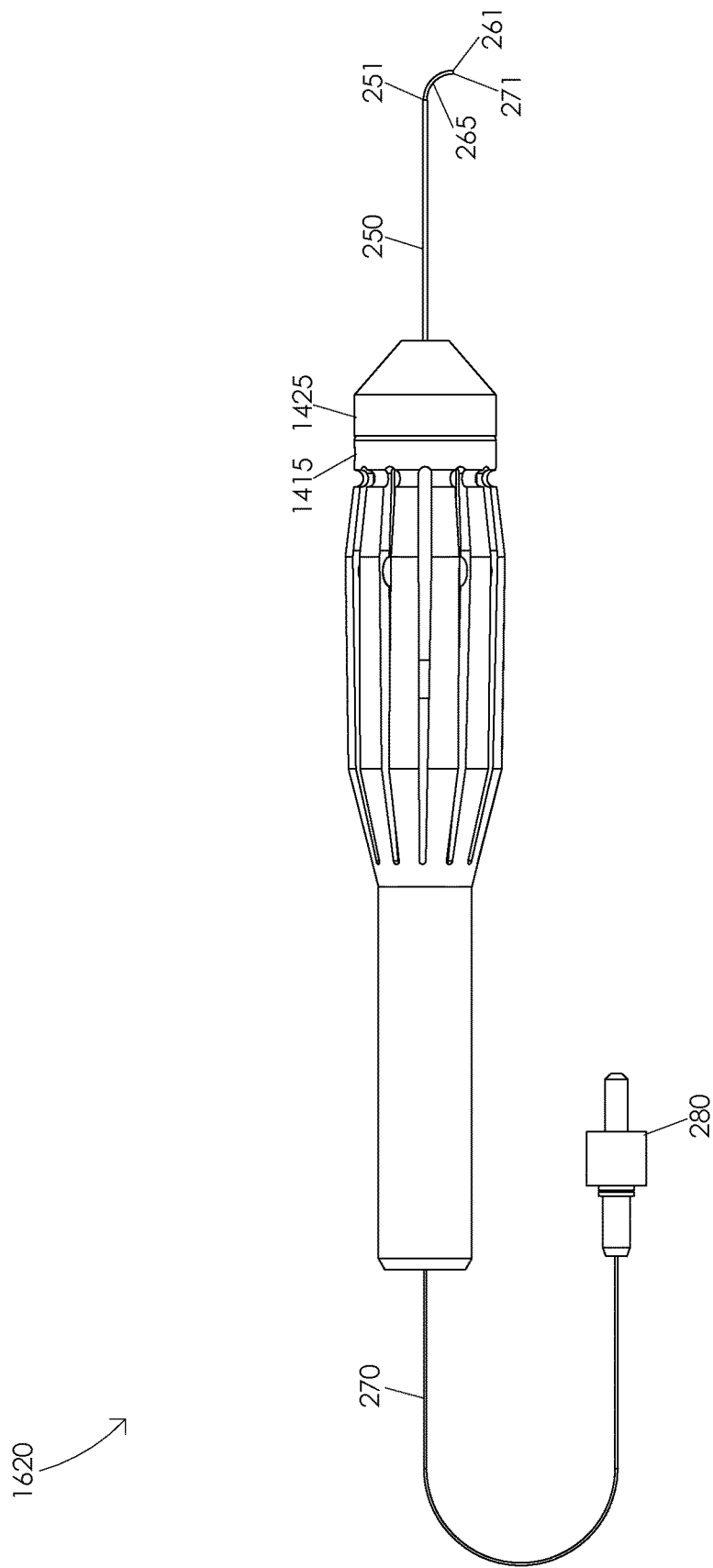

FIGS. 16A, 16B, and 16C illustrate a gradual curving of an optic fiber 270. FIG. 16A illustrates a straightened optic fiber 1600. Illustratively, straightened optic fiber 1600 is fully contained within housing sleeve 250. In one or more embodiments, optic fiber 270 and shape memory sleeve 260 may be fully contained within housing sleeve 250, e.g., when actuation structure 1410 is fully decompressed. For example, when actuation structure 1410 is fully decompressed, actuation mechanism 1510 may be fully retracted within actuation mechanism guide 1421 and actuation ring 1415 may be fully retracted relative to housing sleeve platform 1425. Illustratively, when optic fiber 270 and shape memory sleeve 260 are fully contained within housing sleeve 250, pre-bent angle 265 of shape memory sleeve 260 may be straightened by housing sleeve 250. For example, an angle between housing sleeve 250 and a line tangent to optic fiber distal end 271 may be, e.g., 180 degrees, when housing sleeve 250 contains a straightened optic fiber 1600.

FIG. 16B illustrates a partially curved optic fiber 1610. In one or more embodiments, a compression of a fully decompressed actuation structure 1410 may be configured to gradually extend optic fiber 270 and shape memory sleeve 260 from housing sleeve distal end 251. For example, as actuation structure 1410 is compressed, actuation ring 1415 and actuation mechanism 1510 may be gradually extended relative to handle base 1405. Illustratively, as optic fiber 270 and shape memory sleeve 260 are gradually extended from housing sleeve distal end 251, e.g., by an extension of actuation ring 1415 and actuation mechanism 1510 relative to handle base 1405, shape memory sleeve 260 may cause optic fiber 270 to gradually curve towards pre-bent angle 265. In one or more embodiments, a compression of actuation structure 1410 may be configured to cause a straightened optic fiber 1600 to gradually curve to a partially curved optic fiber 1610. Illustratively, a compression of actuation structure 1410 may gradually extend optic fiber 270 and shape memory sleeve 260 from housing sleeve distal end 251 as actuation ring 1415 and actuation mechanism 1510 are extended relative to handle base 1405. For example, as an extended length of optic fiber 270 and shape memory sleeve 260 is increased, e.g., by a compression of actuation structure 1410, an angle between housing sleeve 250 and a line tangent to optic fiber distal end 271 may be decreased. Illustratively, optic fiber 270 and shape memory sleeve 260 may be extended from housing sleeve distal end 251 at a first length with a first angle between housing sleeve 250 and a line tangent to optic fiber distal end 271. A compression of actuation structure 1410 may be configured to extend optic fiber 270 and shape memory sleeve 260 from housing sleeve distal end 251 at a second length with a second angle between housing sleeve 250 and a line tangent to optic fiber distal end 271. Illustratively, the second length may be greater than the first length and the second angle may be less than the first angle.

FIG. 16C illustrates a fully curved optic fiber 1620. Illustratively, a full compression of actuation structure 1410 may be configured to extend a fully curved optic fiber 1620 from housing sleeve distal end 251. For example, as actuation structure 1410 is fully compressed, actuation ring 1415 and actuation mechanism 1510 may be fully extended relative to handle base 1405. In one or more embodiments, a compression of actuation structure 1410 may be configured to cause a partially curved optic fiber 1610 to gradually curve to a fully curved optic fiber 1620. Illustratively, optic fiber 270 and shape memory sleeve 260 may be extended from housing sleeve distal end 251 at a partially extended length with a partially extended angle between housing sleeve 250 and a line tangent to optic fiber distal end 271. A full compression of actuation structure 1410 may be configured to extend optic fiber 270 and shape memory sleeve 260 from housing sleeve distal end 251 at fully extended length with a fully extended angle between housing sleeve 250 and a line tangent to optic fiber distal end 271. Illustratively, the fully extended length may be greater than the partially extended length and the fully extended angle may be less than the partially extended angle.

In one or more embodiments, one or more properties of a steerable laser probe may be adjusted to attain one or more desired steerable laser probe features. For example, a length that housing sleeve 250 extends from handle distal end 1401 may be adjusted to vary an amount of compression of actuation structure 1410 configured to extend a particular length of optic fiber 270 and shape memory sleeve 260 from housing sleeve distal end 251. Illustratively, a position of actuation mechanism housing 1470 and actuation mechanism 1510 or a length of optic fiber 270 and shape memory sleeve 260 extending distally from a position of actuation mechanism 1510 may be adjusted to vary an amount of compression of actuation structure 1410 configured to extend a particular length of optic fiber 270 and shape memory sleeve 260 from housing sleeve distal end 251. For example, one or more dimensions of platform base 1420 may be adjusted to vary an amount of compression of actuation structure 1410 configured to extend a particular length of optic fiber 270 and shape memory sleeve 260 from housing sleeve distal end 251. In one or more embodiments, a geometry of actuation structure 1410 or a geometry of actuation ring 1415 may be adjusted to vary an amount of compression of actuation structure 1410 configured to extend a particular length of optic fiber 270 and shape memory sleeve 260 from housing sleeve distal end 251. Illustratively, a magnitude of pre-bent angle 265 may be adjusted to vary a magnitude of an angle between housing sleeve 250 and a line tangent to optic fiber distal end 271 when a particular length of optic fiber 270 and shape memory sleeve 260 is extended from housing sleeve distal end 251.

Figure 17A:
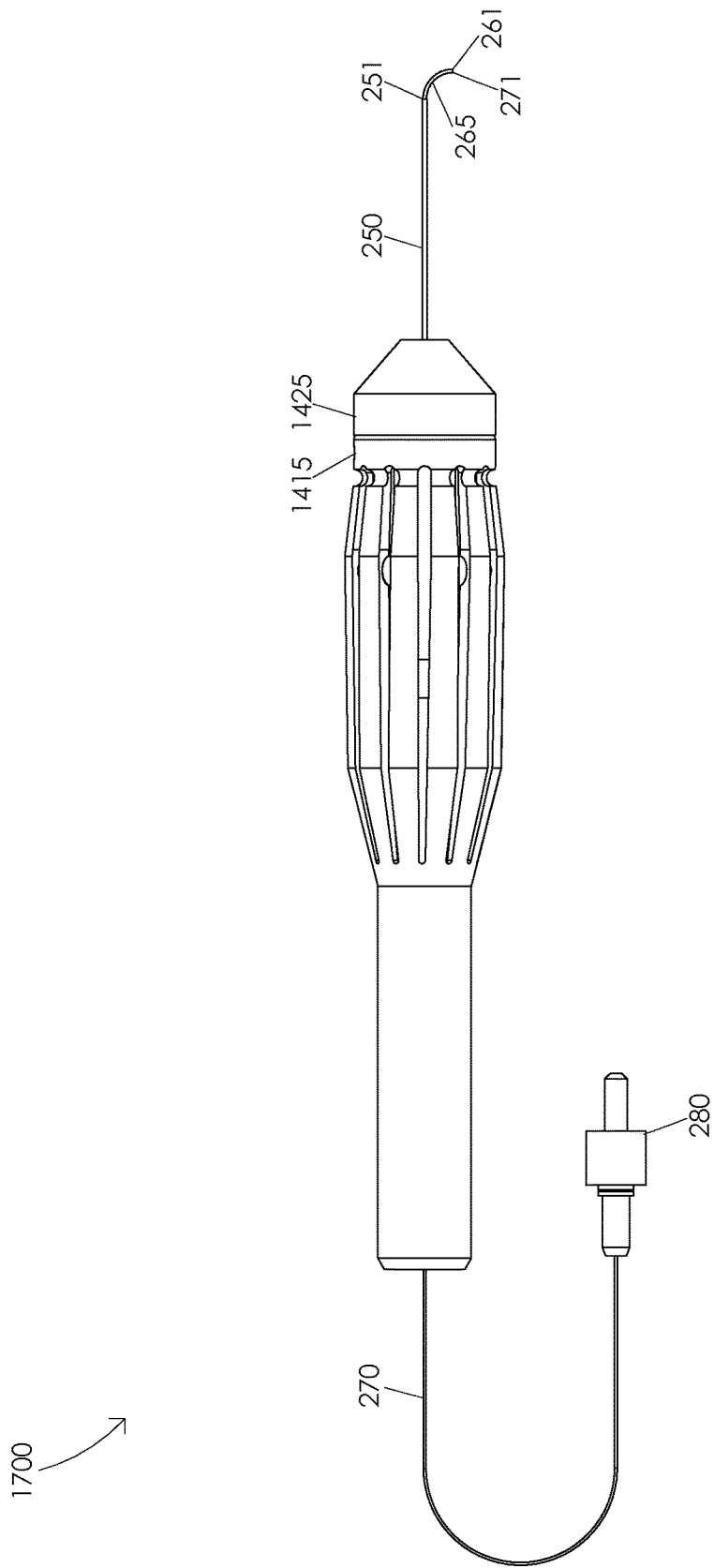
FIGS. 17A, 17B, and 17C illustrate a gradual straightening of an optic fiber.
Figure 17B:
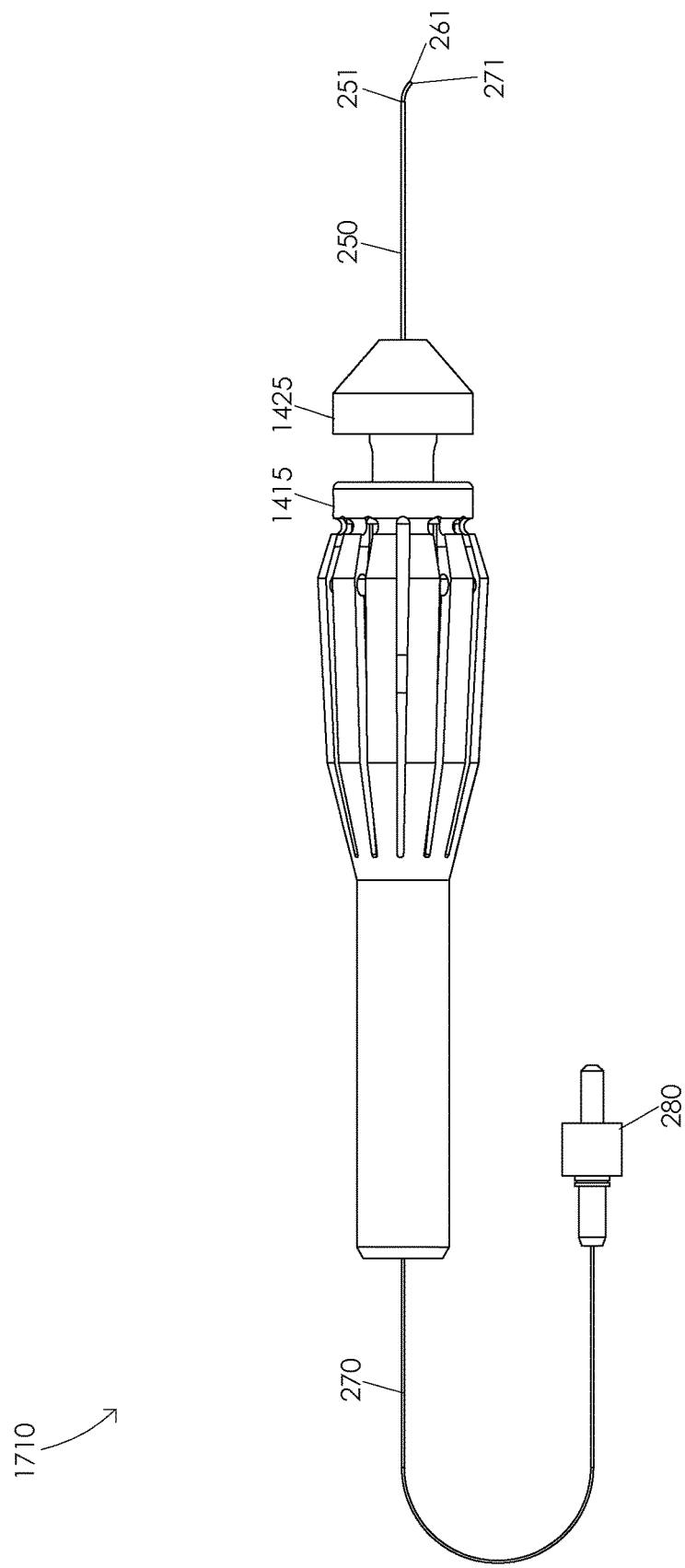
Figure 17C:
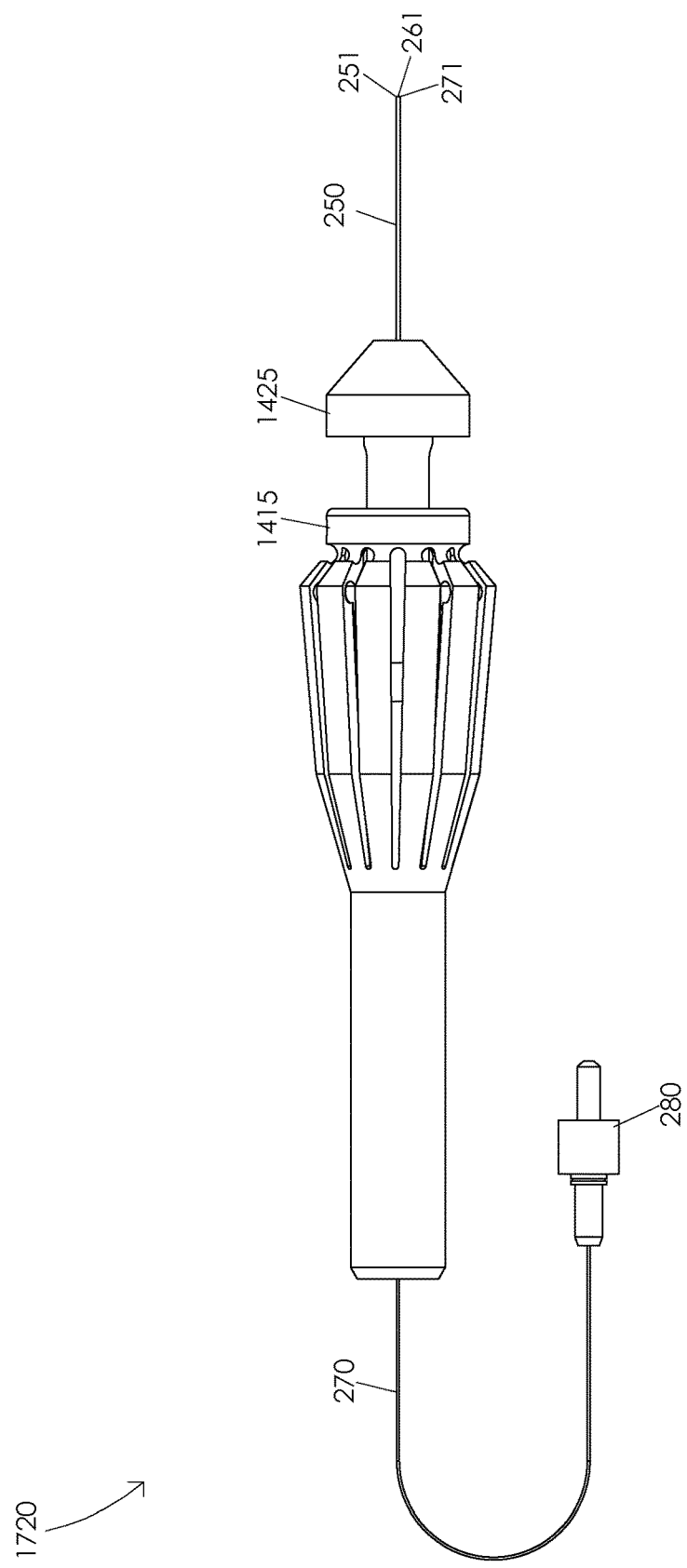

FIGS. 17A, 17B, and 17C illustrate a gradual straightening of an optic fiber 270. FIG. 17A illustrates an extended optic fiber 1700. In one or more embodiments, a full compression of actuation structure 1410 may be configured to extend optic fiber 270 and shape memory sleeve 260 from housing sleeve distal end 251 such that optic fiber 270 comprises an extended optic fiber 1700. Illustratively, shape memory sleeve 260 may be configured to curve an extended optic fiber 1700 at pre-bent angle 265. For example, when extended optic fiber 1700 extends from housing sleeve distal end 251, actuation ring 1415 and actuation mechanism 1510 may be fully extended relative to handle base 1405.

FIG. 17B illustrates a partially refracted optic fiber 1710. Illustratively, a partially refracted optic fiber 1710 may be partially contained within housing sleeve 250 wherein housing sleeve 250 may be configured to straighten a portion of pre-bent angle 265. In one or more embodiments, a decompression of actuation structure 1410 may be configured to retract optic fiber 270 and shape memory sleeve 260 into housing sleeve 250 causing shape memory sleeve 260 to gradually straighten optic fiber 270 from a fully curved optic fiber 1620 to a partially curved optic fiber 1610. For example, a decompression of actuation structure 1410 may be configured to partially retract actuation ring 1415 and actuation mechanism 1510 relative to handle distal end 1401.

FIG. 17C illustrates a fully retracted optic fiber 1720. Illustratively, a fully retracted optic fiber 1720 may be fully contained within housing sleeve 250 wherein housing sleeve 250 may be configured to straighten pre-bent angle 265. In one or more embodiments, a full decompression of actuation structure 1410 may be configured to retract optic fiber 270 and shape memory sleeve 260 into housing sleeve 250 causing shape memory sleeve 260 to gradually straighten optic fiber 270 from a partially curved optic fiber 1610 to a straightened optic fiber 1600. For example, a full decompression of actuation structure 1410 may be configured to fully retract actuation ring 1415 and actuation mechanism 1510 relative to handle distal end 1401.

Illustratively, a surgeon may aim optic fiber distal end 271 at any of a plurality of targets within an eye, e.g., to perform a photocoagulation procedure. In one or more embodiments, a surgeon may aim optic fiber distal end 271 at any target within a particular transverse plane of the inner eye by, e.g., rotating handle 1400 to orient shape memory sleeve 260 in an orientation configured to cause a curvature of optic fiber 270 within the particular transverse plane of the inner eye and varying an amount of compression of actuation structure 1410. Illustratively, a surgeon may aim optic fiber distal end 271 at any target within a particular sagittal plane of the inner eye by, e.g., rotating handle 1400 to orient shape memory sleeve 260 in an orientation configured to cause a curvature of optic fiber 270 within the particular sagittal plane of the inner eye and varying an amount of compression of actuation structure 1410. In one or more embodiments, a surgeon may aim optic fiber distal end 271 at any target within a particular frontal plane of the inner eye by, e.g., varying an amount of compression of actuation structure 1410 to orient a line tangent to optic fiber distal end 271 wherein the line tangent to optic fiber distal end 271 is within the particular frontal plane of the inner eye and rotating handle 1400. Illustratively, a surgeon may aim optic fiber distal end 271 at any target located outside of the particular transverse plane, the particular sagittal plane, and the particular frontal plane of the inner eye, e.g., by varying a rotational orientation of handle 1400 and varying an amount of compression of actuation structure 1410.

FIGS. 18A and 18B are schematic diagrams illustrating a handle 1800. FIG. 18A illustrates a top view of handle 1800. In one or more embodiments, handle 1800 may comprise a handle distal end 1801, a handle proximal end 1802, a handle base 1805, an actuation structure 1810, an actuation platform 1820, and a housing sleeve platform 1825. Illustratively, actuation platform 1820 may comprise an actuation platform distal end 1821 and an actuation platform proximal end 1822. In one or more embodiments, actuation structure 1810 may comprise a plurality of actuation arms 1813. Illustratively, each actuation arm 1813 may comprise at least one extension mechanism 1814. In one or more embodiments, each actuation arm 1813 may comprise an inverted actuation joint 1815.

Illustratively, actuation structure 1810 may be compressed by an application of a compressive force to actuation structure 1810. In one or more embodiments, actuation structure 1810 may be compressed by an application of one or more compressive forces located at one or more locations around an outer perimeter of actuation structure 1810. Illustratively, the one or more locations may comprise any of a plurality of locations around the outer perimeter of actuation structure 1810. For example, a surgeon may compress actuation structure 1810 by squeezing actuation structure 1810. Illustratively, the surgeon may compress actuation structure 1810 by squeezing actuation structure 1810 at any particular location of a plurality of locations around an outer perimeter of actuation structure 1810. For example, a surgeon may rotate handle 1800 and compress actuation structure 1810 from any rotational position of a plurality of rotational positions of handle 1800.

In one or more embodiments, actuation structure 1810 may be compressed by an application of a compressive force to any one or more of the plurality of actuation arms 1813. Illustratively, each actuation arm 1813 may be configured to actuate independently. In one or more embodiments, each actuation arm 1813 may be connected to one or more of the plurality of actuation arms 1813 wherein an actuation of a particular actuation arm 1813 may be configured to actuate every actuation arm 1813 of the plurality of actuation arms 1813. In one or more embodiments, a compression of actuation structure 1810, e.g., due to an application of a compressive force to a particular actuation arm 1813, may be configured to actuate the particular actuation arm 1813. Illustratively, an actuation of the particular actuation arm 1813 may be configured to actuate every actuation arm 1813 of the plurality of actuation arms 1813. In one or more embodiments, an application of a compressive force to a particular actuation arm 1813 may be configured to extend at least one extension mechanism 1814 of the particular actuation arm 1813.

Illustratively, an application of a compressive force to a particular actuation arm 1813 may be configured to retract actuation platform 1820 relative to handle base 1805. In one or more embodiments, as a particular actuation arm 1813 is compressed, e.g., due to an application of a compressive force to the particular actuation arm 1813, an inverted actuation joint 1815 of the particular actuation arm 1813 may be configured to gradually retract actuation platform 1820 relative to handle base 1805. For example, when a compressive force is applied to a particular actuation arm 1813, e.g., and the particular actuation arm 1813 is extended by at least one extension mechanism 1815 of the particular actuation arm 1813, an inverted actuation joint 1815 of the particular actuation arm 1813 may be configured to retract actuation platform 1820 relative to handle base 1805.

FIG. 18B illustrates a cross-sectional view of handle 1800. In one or more embodiments, handle 1800 may comprise an inner bore 1830, an inner bore proximal taper 1850, an actuation mechanism housing 1870, an inner bore distal chamber 1880, and a shape memory sleeve guide 1890. Handle 1800 may be manufactured from any suitable material, e.g., polymers, metals, metal alloys, etc., or from any combination of suitable materials.

Figure 19:
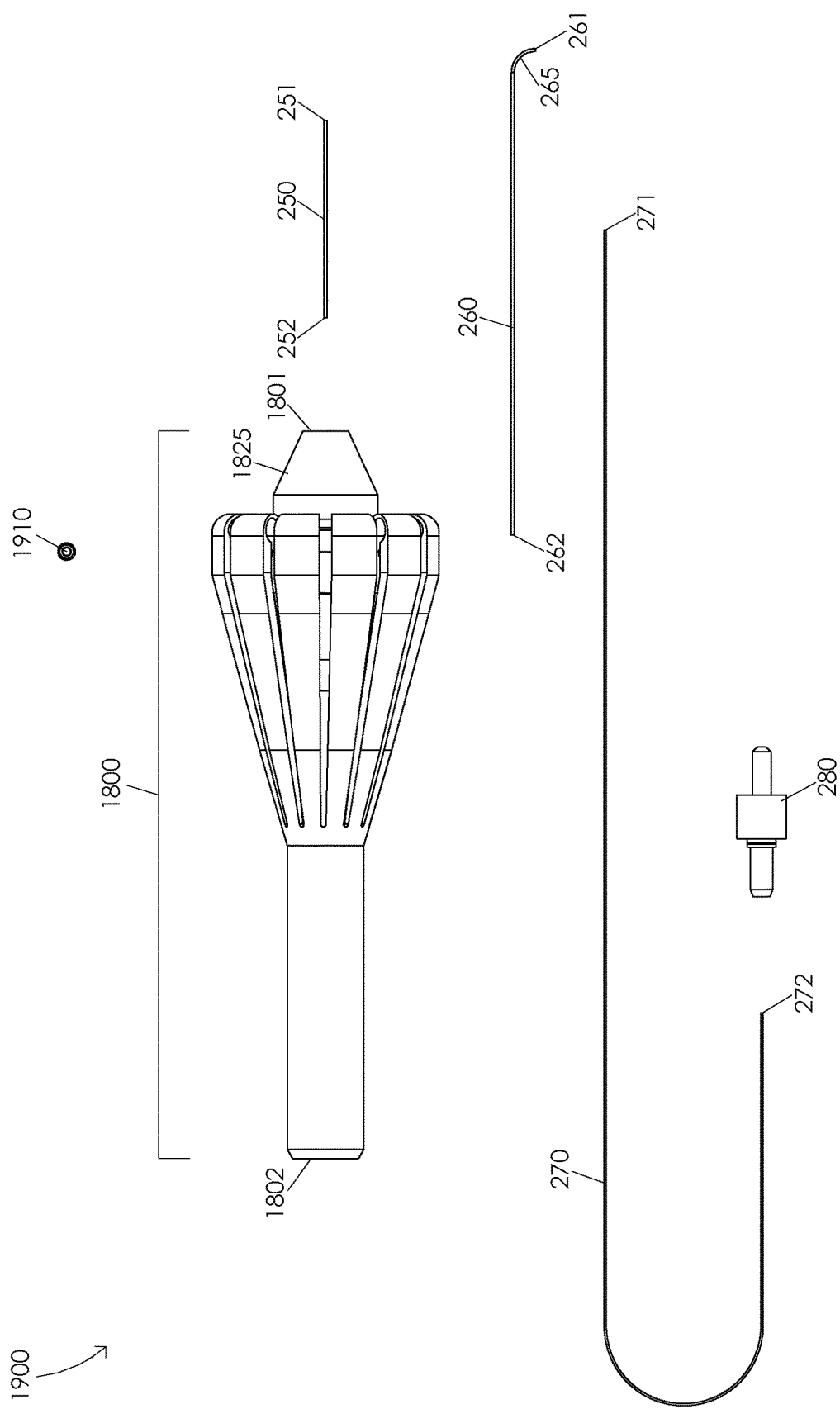
FIG. 19 illustrates an exploded view of a steerable laser probe assembly.

FIG. 19 illustrates an exploded view of a steerable laser probe assembly 1900. In one or more embodiments, steerable laser probe assembly 1900 may comprise a handle 1800, an actuation mechanism 1910, a housing sleeve 250 having a housing sleeve distal end 251 and a housing sleeve proximal end 252, a shape memory sleeve 260 having a shape memory sleeve distal end 261 and a shape memory sleeve proximal end 262, an optic fiber 270 having an optic fiber distal end 271 and an optic fiber proximal end 272, and a light source interface 280. Illustratively, housing sleeve proximal end 252 may be fixed to housing sleeve platform 1825 at handle distal end 1801.

Illustratively, a compression of action structure 1810 may be configured to retract actuation platform 1820, e.g., towards handle proximal end 1802 and away from handle distal end 1801. In one or more embodiments, a decompression of actuation structure 1810 may be configured to extend actuation platform 1820, e.g., towards handle distal end 1801 and away from handle proximal end 1802. Illustratively, actuation mechanism 1910 may be disposed within actuation mechanism housing 1870. In one or more embodiments, a compression of actuation structure 1810 may be configured to actuate actuation mechanism 1910 and actuation platform 1820, e.g., towards handle proximal end 1802 and away from handle distal end 1801. Illustratively, a decompression of actuation structure 1810 may be configured to actuate actuation mechanism 1910 and actuation platform 1820, e.g., towards handle distal end 1801 and away from handle proximal end 1802.

Illustratively, optic fiber 270 may be disposed within shape memory sleeve 260, e.g., such that optic fiber distal end 271 is adjacent to shape memory sleeve distal end 261. Optic fiber 270 may be fixed in a position within shape memory sleeve 260, e.g., with a biocompatible adhesive or any suitable fixation means. In one or more embodiments, optic fiber 270 may be disposed within inner bore 1830 and inner bore distal chamber 1880. Illustratively, optic fiber 270 and shape memory sleeve 260 may be disposed within shape memory sleeve guide 1890 and housing sleeve 250. In one or more embodiments, optic fiber 270 and shape memory sleeve 260 may be disposed in actuation mechanism housing 1870. Illustratively, optic fiber 270 and shape memory sleeve 260 may be attached to actuation mechanism 1910 wherein an actuation of actuation mechanism 1910 may be configured to actuate optic fiber 270 and shape memory sleeve 260. For example, an actuation of actuation mechanism 1910 and actuation platform 1820 may be configured to actuate optic fiber 270 and shape memory sleeve 260 relative to housing sleeve 250.

Illustratively, housing sleeve platform 1825 and housing sleeve 250 may be fixed in a position relative to handle base 1805. In one or more embodiments, an actuation of actuation mechanism 1910 and actuation platform 1820, i.e., away from handle proximal end 1802 and towards handle distal end 1801, may be configured to extend optic fiber 270 and shape memory sleeve 260 out of housing sleeve 250. Illustratively, an actuation of actuation mechanism 1910 and actuation platform 1820, i.e., away from handle distal end 1801 and towards handle proximal end 1802, may be configured to retract optic fiber 270 and shape memory sleeve 260 into housing sleeve 250.

In one or more embodiments, a decompression of actuation structure 1810 may be configured to actuate optic fiber 270 and shape memory sleeve 260 relative to housing sleeve 250 wherein optic fiber 270 and shape memory sleeve 260 may be gradually extended from housing sleeve distal end 251. Illustratively, as optic fiber 270 and shape memory sleeve 260 are gradually extended from housing sleeve 250, e.g., due to a decompression of actuation structure 1810, shape memory sleeve 260 may gradually curve optic fiber 270 towards pre-bent angle 265. In one or more embodiments, a compression of actuation structure 1810 may be configured actuate optic fiber 270 and shape memory sleeve 260 relative to housing sleeve 250 wherein optic fiber 270 and shape memory sleeve 260 are gradually retracted into housing sleeve distal end 251. Illustratively, as optic fiber 270 and shape memory sleeve 260 are gradually retracted into housing sleeve 250, e.g., due to a compression of actuation structure 1810, shape memory sleeve 260 may gradually straighten optic fiber 270 as housing sleeve 250 straightens pre-bent angle 265. In one or more embodiments, an interior portion of housing sleeve 250 may be coated with a lubrication material configured to facilitate actuation of shape memory sleeve 260 and optic fiber 270 relative to housing sleeve 250. Illustratively, the lubrication material may comprise any suitable material, e.g., Teflon.

Figure 20A:
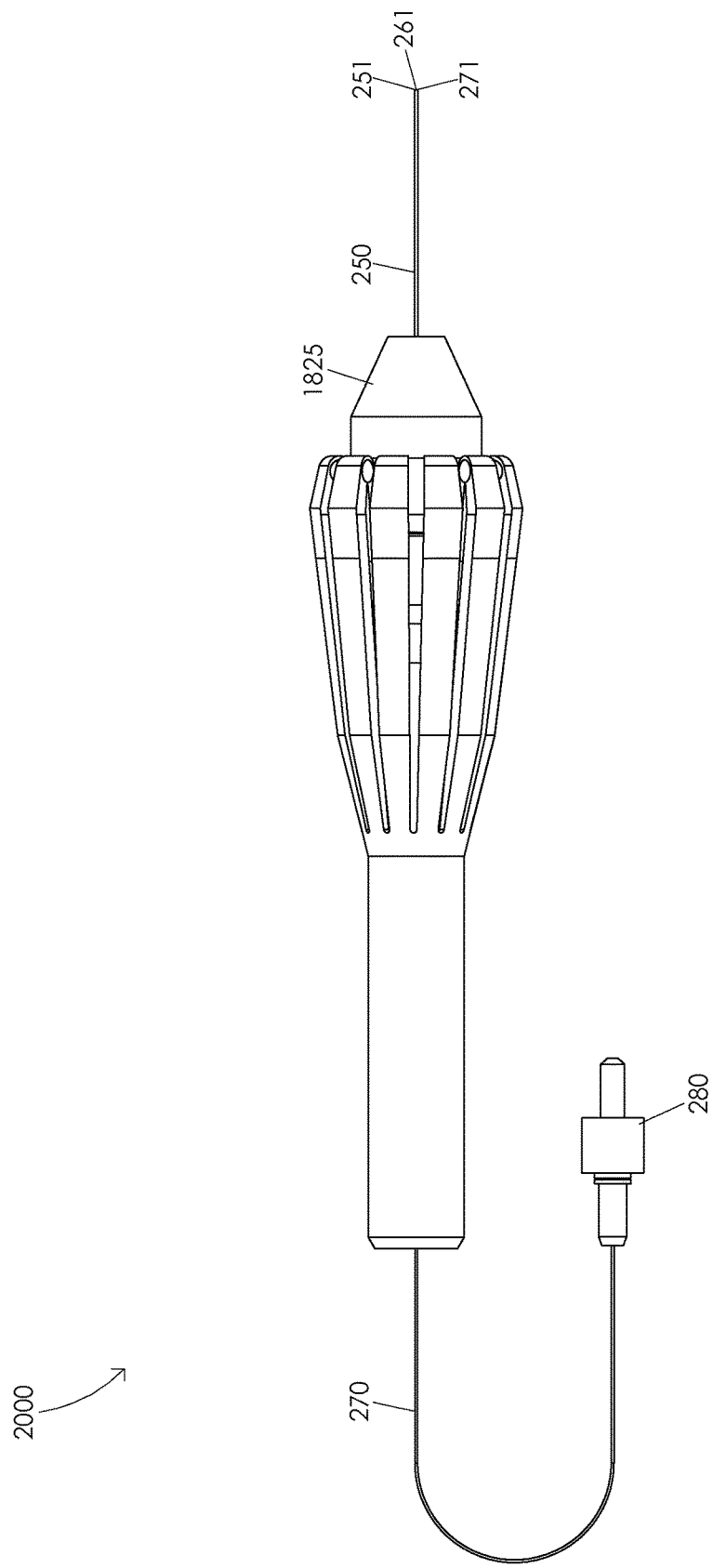
FIGS. 20A, 20B, and 20C illustrate a gradual curving of an optic fiber.
Figure 20B:
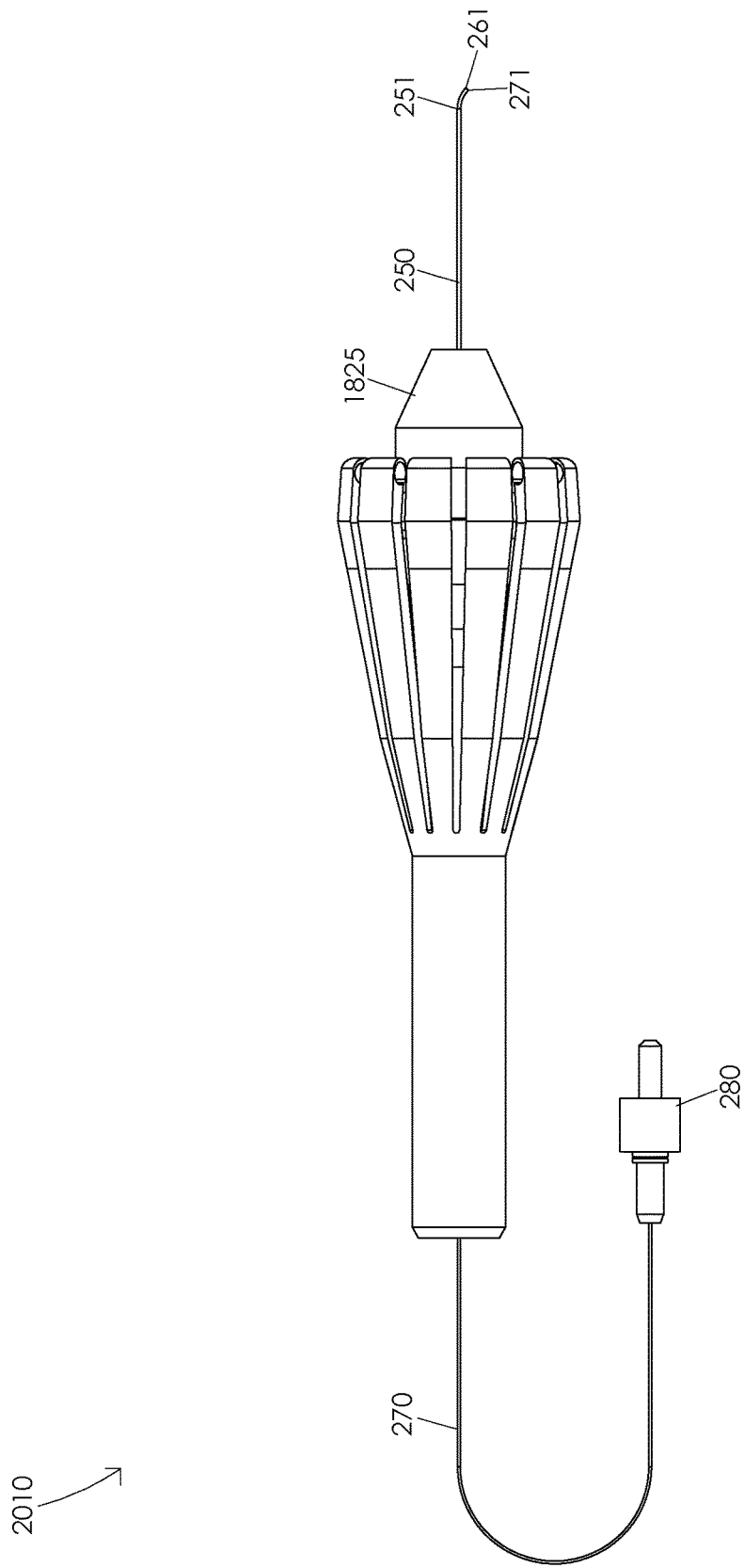
Figure 20C:
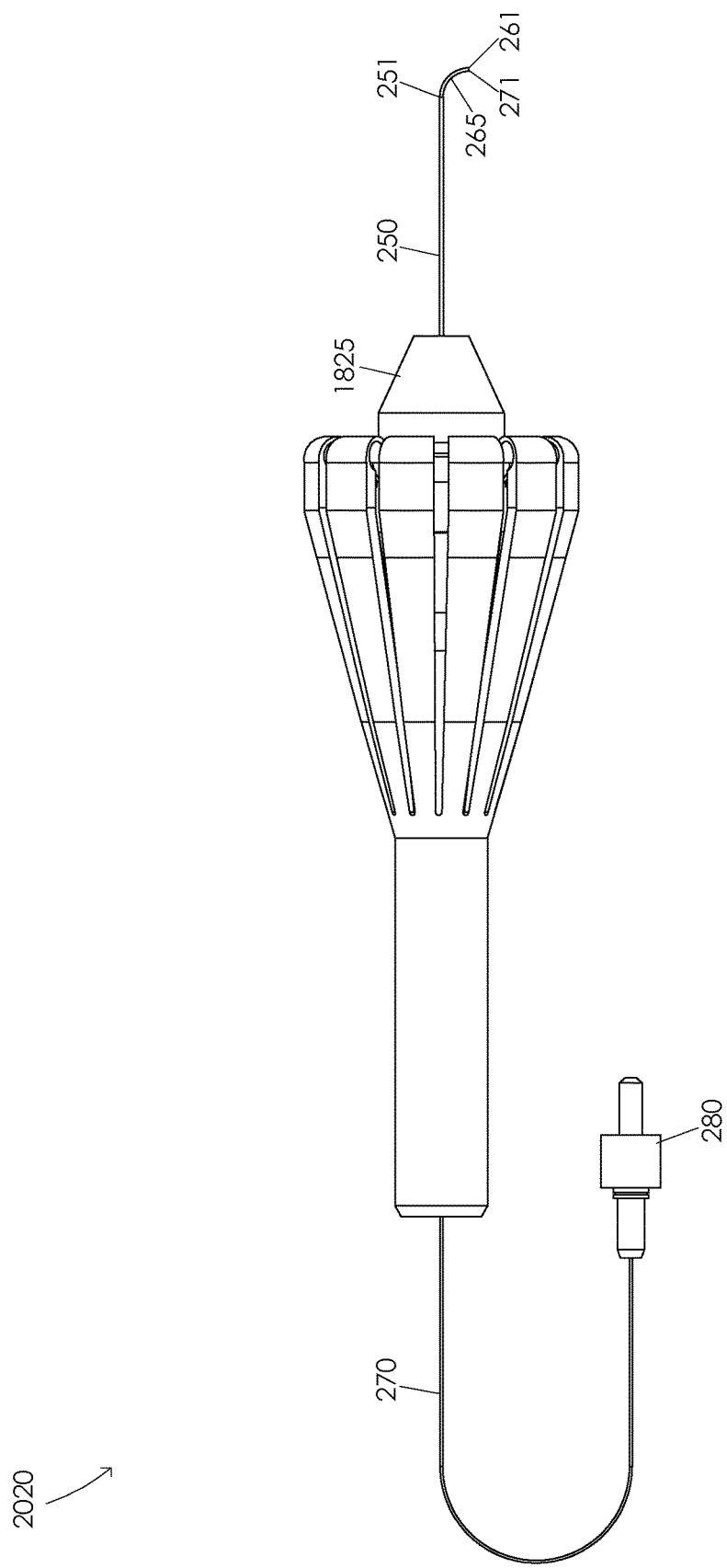

FIGS. 20A, 20B, and 20C illustrate a gradual curving of an optic fiber 270. FIG. 20A illustrates a straightened optic fiber 2000. Illustratively, straightened optic fiber 2000 is fully contained within housing sleeve 250. In one or more embodiments, optic fiber 270 and shape memory sleeve 260 may be fully contained within housing sleeve 250, e.g., when actuation structure 1810 is fully compressed. For example, when actuation structure 1810 is fully compressed, actuation mechanism 1910 and actuation platform 182 may be fully retracted relative to housing sleeve platform 1825. Illustratively, when optic fiber 270 and shape memory sleeve 260 are fully contained within housing sleeve 250, pre-bent angle 265 of shape memory sleeve 260 may be straightened by housing sleeve 250. For example, an angle between housing sleeve 250 and a line tangent to optic fiber distal end 271 may be, e.g., 180 degrees, when housing sleeve 250 contains a straightened optic fiber 2000.

FIG. 20B illustrates a partially curved optic fiber 2010. In one or more embodiments, a decompression of a fully compressed actuation structure 1810 may be configured to gradually extend optic fiber 270 and shape memory sleeve 260 from housing sleeve distal end 251. For example, as actuation structure 1810 is decompressed, actuation mechanism 1910 and actuation platform 1820 may be gradually extended relative to handle base 1805. Illustratively, as optic fiber 270 and shape memory sleeve 260 are gradually extended from housing sleeve distal end 251, e.g., by an extension of actuation mechanism 1910 and actuation platform 1820 relative to handle base 1805, shape memory sleeve 260 may cause optic fiber 270 to gradually curve towards pre-bent angle 265. In one or more embodiments, a decompression of actuation structure 1810 may be configured to cause a straightened optic fiber 2000 to gradually curve to a partially curved optic fiber 2010. Illustratively, a decompression of actuation structure 1810 may gradually extend optic fiber 270 and shape memory sleeve 260 from housing sleeve distal end 251 as actuation mechanism 1910 and actuation platform 1820 are extended relative to handle base 1805. For example, as an extended length of optic fiber 270 and shape memory sleeve 260 is increased, e.g., by a decompression of actuation structure 1810, an angle between housing sleeve 250 and a line tangent to optic fiber distal end 271 may be decreased. Illustratively, optic fiber 270 and shape memory sleeve 260 may be extended from housing sleeve distal end 251 at a first length with a first angle between housing sleeve 250 and a line tangent to optic fiber distal end 271. A decompression of actuation structure 1810 may be configured to extend optic fiber 270 and shape memory sleeve 260 from housing sleeve distal end 251 at a second length with a second angle between housing sleeve 250 and a line tangent to optic fiber distal end 271. Illustratively, the second length may be greater than the first length and the second angle may be less than the first angle.

FIG. 20C illustrates a fully curved optic fiber 2020. Illustratively, a full decompression of actuation structure 1810 may be configured to extend a fully curved optic fiber 2020 from housing sleeve distal end 251. For example, as actuation structure 1810 is fully decompressed, actuation mechanism 1910 and actuation platform 1820 may be fully extended relative to handle base 1805. In one or more embodiments, a decompression of actuation structure 1810 may be configured to cause a partially curved optic fiber 2010 to gradually curve to a fully curved optic fiber 2020. Illustratively, optic fiber 270 and shape memory sleeve 260 may be extended from housing sleeve distal end 251 at a partially extended length with a partially extended angle between housing sleeve 250 and a line tangent to optic fiber distal end 271. A full decompression of actuation structure 1810 may be configured to extend optic fiber 270 and shape memory sleeve 260 from housing sleeve distal end 251 at fully extended length with a fully extended angle between housing sleeve 250 and a line tangent to optic fiber distal end 271. Illustratively, the fully extended length may be greater than the partially extended length and the fully extended angle may be less than the partially extended angle.

In one or more embodiments, one or more properties of a steerable laser probe may be adjusted to attain one or more desired steerable laser probe features. For example, a length that housing sleeve 250 extends from handle distal end 1801 may be adjusted to vary an amount of decompression of actuation structure 1810 configured to extend a particular length of optic fiber 270 and shape memory sleeve 260 from housing sleeve distal end 251. Illustratively, a position of actuation mechanism housing 1870 and actuation mechanism 1910 or a length of optic fiber 270 and shape memory sleeve 260 extending distally from a position of actuation mechanism 1910 may be adjusted to vary an amount of decompression of actuation structure 1810 configured to extend a particular length of optic fiber 270 and shape memory sleeve 260 from housing sleeve distal end 251. For example, one or more dimensions of actuation platform 1820 may be adjusted to vary an amount of decompression of actuation structure 1810 configured to extend a particular length of optic fiber 270 and shape memory sleeve 260 from housing sleeve distal end 251. In one or more embodiments, a geometry of actuation structure 1810 may be adjusted to vary an amount of decompression of actuation structure 1810 configured to extend a particular length of optic fiber 270 and shape memory sleeve 260 from housing sleeve distal end 251. Illustratively, a magnitude of pre-bent angle 265 may be adjusted to vary a magnitude of an angle between housing sleeve 250 and a line tangent to optic fiber distal end 271 when a particular length of optic fiber 270 and shape memory sleeve 260 is extended from housing sleeve distal end 251.

Figure 21A:
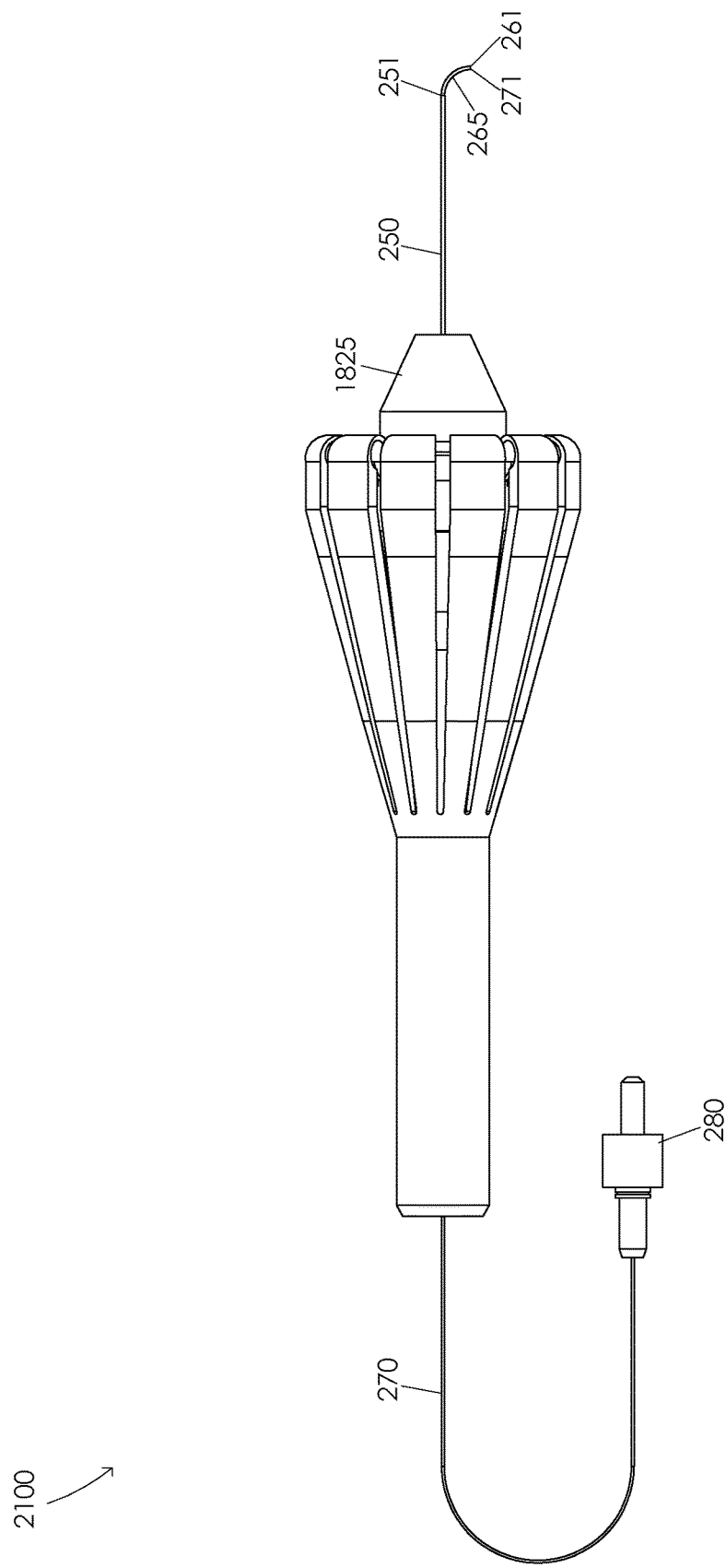
FIGS. 21A, 21B, and 21C illustrate a gradual straightening of an optic fiber.
Figure 21B:
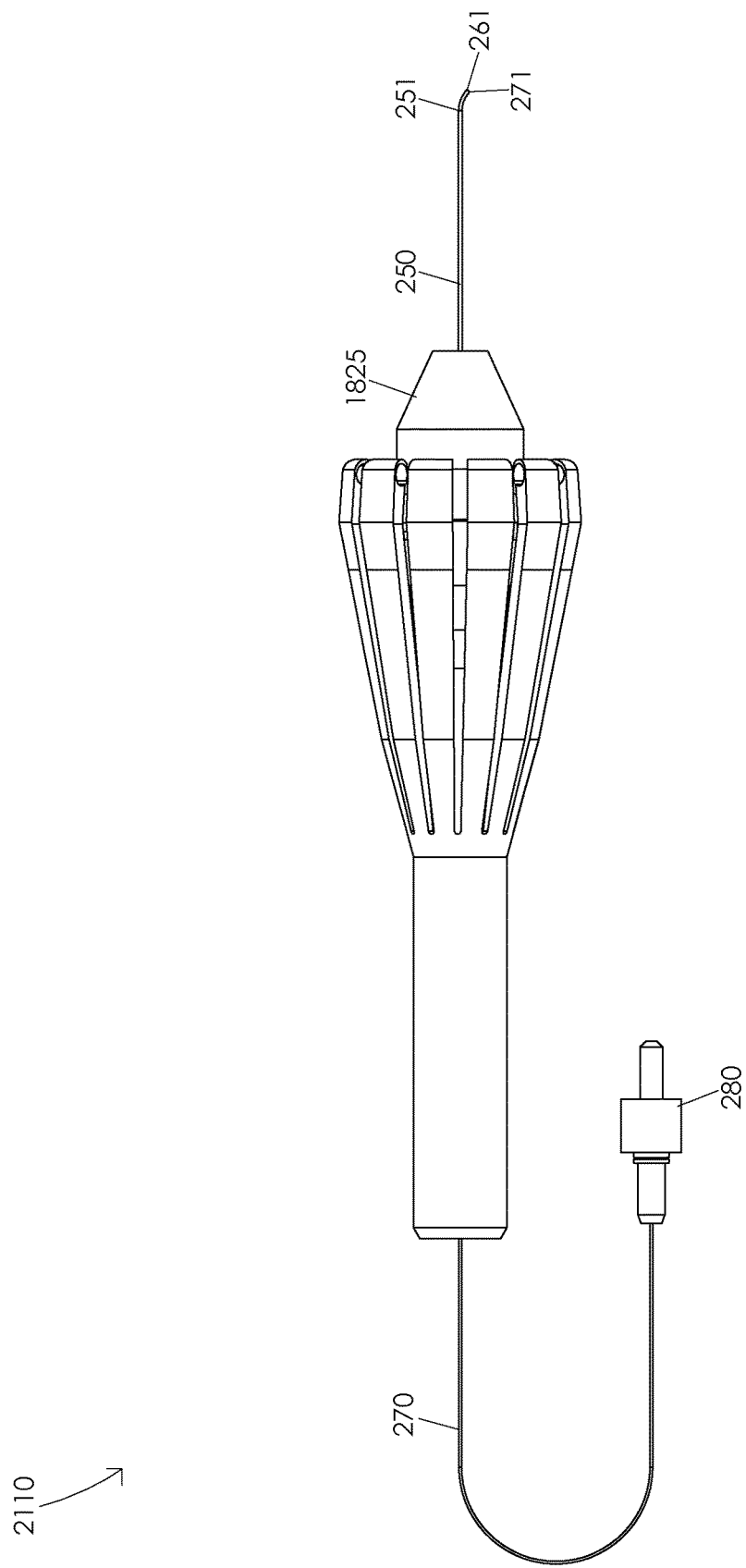
Figure 21C:
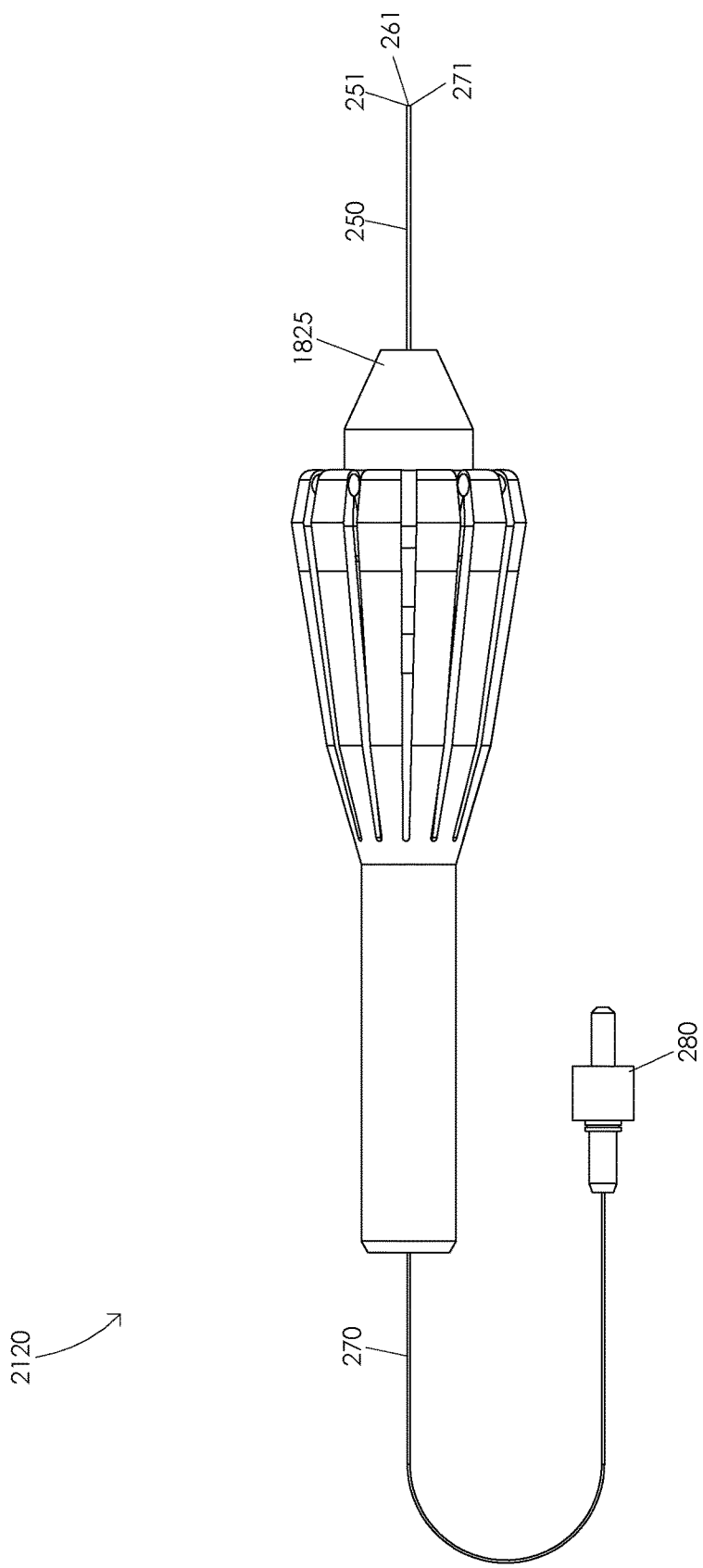

FIGS. 21A, 21B, and 21C illustrate a gradual straightening of an optic fiber 270. FIG. 21A illustrates an extended optic fiber 2100. In one or more embodiments, a full decompression of actuation structure 1810 may be configured to extend optic fiber 270 and shape memory sleeve 260 from housing sleeve distal end 251 such that optic fiber 270 comprises an extended optic fiber 2100. Illustratively, shape memory sleeve 260 may be configured to curve an extended optic fiber 2100 at pre-bent angle 265. For example, when extended optic fiber 2100 extends from housing sleeve distal end 251, actuation mechanism 1910 and actuation platform 1820 may be fully extended relative to handle base 1805.

FIG. 21B illustrates a partially retracted optic fiber 2110. Illustratively, a partially refracted optic fiber 2110 may be partially contained within housing sleeve 250 wherein housing sleeve 250 may be configured to straighten a portion of pre-bent angle 265. In one or more embodiments, a compression of actuation structure 1810 may be configured to retract optic fiber 270 and shape memory sleeve 260 into housing sleeve 250 causing shape memory sleeve 260 to gradually straighten optic fiber 270 from a fully curved optic fiber 2020 to a partially curved optic fiber 2010. For example, a compression of actuation structure 1810 may be configured to partially retract actuation mechanism 1910 and actuation platform 1820 relative to handle distal end 1801.

FIG. 21C illustrates a fully retracted optic fiber 2120. Illustratively, a fully retracted optic fiber 2120 may be fully contained within housing sleeve 250 wherein housing sleeve 250 may be configured to straighten pre-bent angle 265. In one or more embodiments, a full compression of actuation structure 1810 may be configured to retract optic fiber 270 and shape memory sleeve 260 into housing sleeve 250 causing shape memory sleeve 260 to gradually straighten optic fiber 270 from a partially curved optic fiber 2010 to a straightened optic fiber 2000. For example, a full compression of actuation structure 1810 may be configured to fully retract actuation mechanism 1910 and actuation platform 1820 relative to handle distal end 1801.

Illustratively, a surgeon may aim optic fiber distal end 271 at any of a plurality of targets within an eye, e.g., to perform a photocoagulation procedure. In one or more embodiments, a surgeon may aim optic fiber distal end 271 at any target within a particular transverse plane of the inner eye by, e.g., rotating handle 1800 to orient shape memory sleeve 260 in an orientation configured to cause a curvature of optic fiber 270 within the particular transverse plane of the inner eye and varying an amount of compression of actuation structure 1810. Illustratively, a surgeon may aim optic fiber distal end 271 at any target within a particular sagittal plane of the inner eye by, e.g., rotating handle 1800 to orient shape memory sleeve 260 in an orientation configured to cause a curvature of optic fiber 270 within the particular sagittal plane of the inner eye and varying an amount of compression of actuation structure 1810. In one or more embodiments, a surgeon may aim optic fiber distal end 271 at any target within a particular frontal plane of the inner eye by, e.g., varying an amount of compression of actuation structure 1810 to orient a line tangent to optic fiber distal end 271 wherein the line tangent to optic fiber distal end 271 is within the particular frontal plane of the inner eye and rotating handle 1800. Illustratively, a surgeon may aim optic fiber distal end 271 at any target located outside of the particular transverse plane, the particular sagittal plane, and the particular frontal plane of the inner eye, e.g., by varying a rotational orientation of handle 1800 and varying an amount of compression of actuation structure 1810.

The foregoing description has been directed to particular embodiments of this invention. It will be apparent; however, that other variations and modifications may be made to the described embodiments, with the attainment of some or all of their advantages. Specifically, it should be noted that the principles of the present invention may be implemented in any probe system. Furthermore, while this description has been written in terms of a surgical instrument handle for selectively actuating a shape memory sleeve and an optic fiber relative to a housing sleeve and for selectively actuating a housing sleeve relative to a shape memory sleeve and an optic fiber, the teachings of the present invention are equally suitable to systems where the functionality of actuation may be employed. Therefore, it is the object of the appended claims to cover all such variations and modifications as come within the true spirit and scope of the invention.

What is claimed is:

1. A method for photocoagulating tissue within an inner eye comprising:
   applying a force to an actuation structure of a handle wherein the handle has a handle distal end and a handle proximal end, and wherein the actuation structure has a plurality of actuation arms;
   compressing the actuation structure, wherein compressing the actuation structure causes:
      retraction of an actuation cone into the actuation structure wherein the actuation cone has an actuation cone distal end and an actuation cone proximal end;
      retraction of a housing sleeve relative to both an optic fiber and shape memory sleeve wherein the housing sleeve has a housing sleeve distal end and a housing sleeve proximal end;
      curving of the shape memory sleeve wherein the shape memory sleeve has a shape memory sleeve distal end and a shape memory sleeve proximal end; and
      curving of the optic fiber wherein the optic fiber has an optic fiber distal end and an optic fiber proximal end;
   aiming the optic fiber distal end at a first photocoagulation target tissue within an inner eye wherein the first photocoagulation target tissue is within a particular transverse plane of the inner eye;
   cauterizing the first photocoagulation target tissue;
   rotating the handle; and
   aiming the optic fiber distal end at a second photocoagulation target tissue within the inner eye wherein the second photocoagulation target tissue is within a particular frontal plane of the inner eye.

2. The method of claim 1 further comprising: straightening the optic fiber.

3. The method of claim 1 further comprising:
   aiming the optic fiber distal end at a third photocoagulation target tissue within the inner eye wherein the third photocoagulation target tissue is within a particular sagittal plane of the inner eye.

4. The method of claim 1 further comprising: exposing the optic fiber from the housing sleeve distal end.

5. The method of claim 1 wherein the shape memory sleeve is manufactured from nitinol.

6. The method of claim 1 further comprising:
   exposing the shape memory sleeve from the housing sleeve distal end.

7. The method of claim 1 further comprising:
   providing a force to resist a retraction of the actuation cone into the actuation structure.

8. The method of claim 1 further comprising:
   decompressing the actuation structure.

9. The method of claim 8 further comprising:
   extending the actuation cone from the actuation structure.

10. The method of claim 8 further comprising:
    straightening the optic fiber.

11. The method of claim 8 further comprising: extending the housing sleeve relative to the optic fiber.

12. The method of claim 8 further comprising: extending the housing sleeve over the optic fiber.

13. The method of claim 8 further comprising: straightening the shape memory sleeve.

14. The method of claim 13 further comprising: extending the housing sleeve relative to the shape memory sleeve.

15. The method of claim 13 further comprising: extending the housing sleeve over the shape memory sleeve.

16. The method of claim 1 wherein the optic fiber is disposed in the shape memory sleeve.

17. The method of claim 1 wherein the optic fiber is disposed in an inner bore of the handle.

* * * * *